United States Patent
Baudin et al.

(10) Patent No.: US 7,279,200 B2
(45) Date of Patent: *Oct. 9, 2007

(54) PROCESS FOR PRODUCING COATINGS USING SURFACE-ACTIVE PHOTOINITIATORS

(75) Inventors: Gisèle Baudin, Allschwil (CH); Tunja Jung, Rheinfelden-Herten (DE)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 505 days.

This patent is subject to a terminal disclaimer.

(21) Appl. No.: 10/343,620

(22) PCT Filed: Aug. 7, 2001

(86) PCT No.: PCT/EP01/09123

§ 371 (c)(1),
(2), (4) Date: Feb. 3, 2003

(87) PCT Pub. No.: WO02/14439

PCT Pub. Date: Feb. 21, 2002

(65) Prior Publication Data

US 2003/0213931 A1 Nov. 20, 2003

(30) Foreign Application Priority Data

Aug. 14, 2000 (EP) .................................. 00810720

(51) Int. Cl.
*B05D 3/06* (2006.01)
*G03C 1/00* (2006.01)

(52) U.S. Cl. ................. 427/557; 430/270.1; 430/281.1

(58) Field of Classification Search ............. 427/385.5, 427/457, 487, 493, 508, 514, 515, 520, 521, 427/553, 557, 558, 180, 258, 372.2, 387, 427/388.1, 389.7, 407.1, 407.2, 409; 522/8, 522/37; 560/9, 51, 53; 549/465; 430/270.1, 430/281.1, 325

See application file for complete search history.

(56) References Cited

U.S. PATENT DOCUMENTS 6,048,660 A * 4/2000 Leppard et al. .......... 430/270.1
6,906,113 B2 * 6/2005 Baudin et al. ................ 522/37

FOREIGN PATENT DOCUMENTS

GB 1534320 11/1978
WO 98/33761 8/1998

OTHER PUBLICATIONS

Huyser et al., "The Photochemical Reactions of Alkyl Phenylglyoxalates in Alcohols," J. Org. Chem. 1964, 29, 276-278.*
Hu et al., "Alkyl phenylglyoxylates as radical photoinitiators creating negative photoimages," J. Mater. Chem., 1997, 7(9), 1737-1740.*
Hu et al., "Photochemical Reactions of Halo-/Aryl Sulfide-Substituted Alkyl Phenylglyoxylate, an Assessment of the Lifetime of the Intermediate 1,4-Biradical," J. Org. Chem. 1997, 62, 7827-7831.*
Hu et al., "Fluorescence Probe Techniques (FPT) for Measuring the Relative Efficiencies of Free-Radical Photoinitiators," Macromolecules 1998, 31, 4107-4113.*

* cited by examiner

*Primary Examiner*—William Phillip Fletcher, III
(74) *Attorney, Agent, or Firm*—Joseph C. Suhadolnik

(57) ABSTRACT

A process for producing stable, scratch-resistant coatings comprising the preparation of a photocurable formulation containing certain siloxane photoinitiators as surface-active initiators, application of the formulation to a substrate and the curing of the formulation by exposure to electromagnetic radiation with wavelengths from 200 nm into the IR region and prior, simultaneous or subsequent exposure to heat.

15 Claims, No Drawings

PROCESS FOR PRODUCING COATINGS USING SURFACE-ACTIVE PHOTOINITIATORS

The invention relates to a process for producing stable, scratch-resistant coatings using siloxane photoinitiators as surface-active initiators, and to novel surface-active photoinitiators.

For improving the miscibility (compatibility) of photoinitiators with silicone substrates to be crosslinked photochemically, WO 97/49768, U.S. Pat. Nos. 5,776,658, 4,391,963 and EP-A 088842, for example, propose photoinitiators, for example of the hydroxyketone, aminoketone, benzoin ether, benzophenone or thioxanthone type, which have been modified with silyl radicals, including in particular polymeric silyl radicals. Additionally, the patents U.S. Pat. Nos. 4,536,265, 4,534,838 and EP-A 162572 describe a wide variety of photoinitiator structures provided with organopolysiloxane radicals. These compounds are, for example, derived from dialkoxyacetophenones and have increased solubility in silicone substrates. U.S. Pat. No. 4,507,187 discloses diketo photoinitiators containing silyl groups as photoinitiators of good solubility in silicone polymers, and also the polymers obtained with these initiators. U.S. Pat. No. 4,477,326 describes self-polymerizing siloxane polymers containing photoinitiators as groups which trigger the polymerization reaction. Polymeric photoinitiators with siloxane radicals are specified in U.S. Pat. No. 4,587,276.

A. Kolar, H. F. Gruber and G. Greber report in J. M. S. Pure Appl. Chem. A31 (3) (1994), 305-318 on reactive, silyl-derivatized a-hydroxy ketone photoinitiators. The literature references mentioned deal in particular with the solution of the problem of improving the miscibility of the photoinitiators with the substrate that is to be polymerized, i.e. of making the distribution of the initiator within the substrate as homogeneous as possible. WO 98/00456 proposes certain coating compositions and also a curing method by which improved coating surface properties are achieved. Phenylglyoxalate esters, having long alkyl ester groups are described, for example, in U.S. Pat. No. 4,024,297.

Within the coatings industry a search is on for new, energy-saving, emissions-minimizing curing mechanisms and applications for preparing stable, scratch-resistant coatings. A particular requirement is to improve the surface of coatings, particularly with regard to hardness, resistance and gloss properties.

It has now been found that the desired properties may be achieved when certain photoinitiators are used in the coatings that are to be cured. For this purpose, the photoinitiator is not distributed as homogeneously as possible in the formulation to be cured but instead accumulates specifically at the surface of the coating to be cured; in other words, there is a specific orientation of the initiator towards the surface of the formulation. To achieve this it is necessary to use specially equipped photoinitiators.

The invention provides a process for producing coatings having stable scratch-resistant surfaces, in which (1) a photocurable formulation comprising
   (A) an ethylenically unsaturated polymerizable compound; and
   (B) a photoinitiator;

is prepared;
(2) this formulation is applied to a substrate; and
(3) the formulation is cured either
   only by exposure to electromagnetic radiation with a wavelength ranging from 200 nm into the IR region, or
   by exposure to electromagnetic radiation with a wavelength ranging from 200 nm into the IR region and prior, simultaneous and/or subsequent exposure to heat;

wherein
the formulation comprises as photoinitiator (B) at least one surface-active photoinitiator of the formula I which accumulates at the surface of the formulation

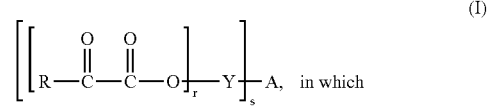

R is a radical of the formula II

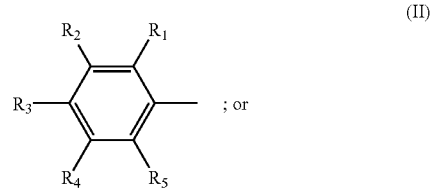

R is naphthyl, anthracyl, phenanthryl or a heterocyclic radical, the radicals naphthyl, anthracyl, phenanthryl and/or the heterocycle being unsubstituted or substituted by $C_1$-$C_8$alkyl, phenyl, $OR_6$, $SR_7$ and/or $NR_8R_9$, where the substituents $OR_6$, $SR_7$, $NR_8R_9$ may form 5- or 6-membered rings via the radicals $R_6$, $R_7$, $R_8$ and/or $R_9$ with further substituents on the naphthyl, anthracyl or phenanthryl ring or on the heterocycle or with one of the carbon atoms of the naphthyl, anthracyl or phenanthryl ring or with one of the carbon atoms of the heterocycle; and $R_1$, $R_2$, $R_3$, $R_4$ and $R_5$ independently of one another are hydrogen; unsubstituted $C_1$-$C_{12}$alkyl or $C_1$-$C_{12}$alkyl substituted by OH, $C_1$-$C_4$alkoxy, phenyl, naphthyl, halogen, CN and/or —O(CO)$R_{10}$; or are $C_2$-$C_{12}$alkyl interrupted by one or more non-successive oxygen atoms; or are $OR_6$; $SR_7$; $NR_8R_9$; halogen; unsubstituted or $C_1$-$C_4$alkyl- and/or $C_1$-$C_4$alkoxy-substituted phenyl, where the substituents $OR_6$, $SR_7$, $NR_8R_9$ may form 5- or 6-membered rings via the radicals $R_6$, $R_7$, $R_8$ and/or $R_9$ with further substituents on the phenyl ring or one of the carbon atoms of the phenyl ring;

$R_6$ and $R_7$ independently of one another are hydrogen; unsubstituted $C_1$-$C_{12}$alkyl or $C_1$-$C_{12}$alkyl substituted by OH, $C_1$-$C_4$alkoxy, phenyl, phenoxy and/or —O(CO)$R_{10}$; or are $C_2$-$C_{12}$alkyl interrupted by one or more non-successive oxygen atoms; or are unsubstituted phenyl, $C_3$-$C_6$alkenyl, cyclopentyl, cyclohexyl or naphthyl; or are $C_1$-$C_4$alkoxy-, phenyl- and/or $C_1$-$C_4$alkyl-substituted phenyl, $C_3$-$C_6$alkenyl, cyclopentyl, cyclohexyl or naphthyl;

$R_8$ and $R_9$ independently of one another are hydrogen; unsubstituted $C_1$-$C_{12}$alkyl or $C_1$-$C_{12}$alkyl substituted by OH, $C_1$-$C_4$alkoxy and/or phenyl; or are $C_2$-$C_{12}$alkyl interrupted by one or more non-successive oxygen atoms; or are phenyl, —(CO)$R_{10}$ or $SO_2R_{11}$; or $R_8$ and $R_9$, together with the nitrogen atom to which they are attached, form a 5-, 6- or 7-membered ring which is uninterrupted or interrupted by —O— or —$NR_{12}$—;

$R_{10}$ is $C_1$-$C_8$alkyl; unsubstituted phenyl; or phenyl substituted by $C_1$-$C_4$alkyl and/or $C_1$-$C_4$alkoxy;

$R_{11}$ is $C_1$-$C_{12}$alkyl, unsubstituted phenyl or phenyl substituted by $C_1$-$C_4$alkyl;

$R_{12}$ is hydrogen; unsubstituted $C_1$-$C_8$alkyl; $C_1$-$C_8$alkyl substituted by OH or $C_1$-$C_4$alkoxy; unsubstituted phenyl; phenyl substituted by OH, $C_1$-$C_4$alkyl and/or $C_1$-$C_4$alkoxy; and A, if s is 1, is either a surface-active radical $A_0$, where $A_0$ is unsubstituted $C_6$-$C_{30}$alkyl, $C_6$-$C_{30}$alkenyl, $C_6$-$C_{30}$alkynyl, $C_6$-$C_{30}$aralkyl; OH—, $C_1$-$C_4$alkoxy-, phenyl-, naphthyl-, halogen-, CN—, $SR_7$—, $NR_8R_9$— and/or —O(CO)$R_{10}$-substituted $C_6$-$C_{30}$alkyl, $C_6$-$C_{30}$alkenyl, $C_6$-$C_{30}$alkynyl, $C_6$-$C_{30}$aralkyl; and the radical $A_0$ is uninterrupted or interrupted by one or more —O—, —S— or —$NR_{12}$—;

or is a surface-active radical of the formula III

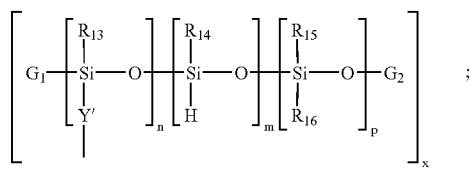
(III)

in which the units IIIa, IIIb and/or IIIc

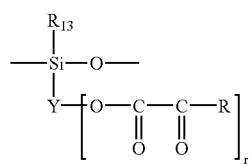
(IIIa)

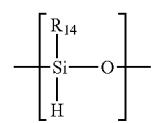
(IIIb)

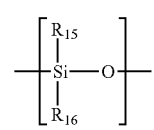
(IIIc)

are distributed randomly or in blocks; and $G_1$ is $C_1$-$C_{18}$alkyl or a radical of the formula

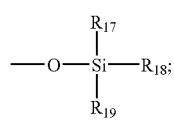

$G_2$ is $C_1$-$C_{18}$alkyl or a radical of the formula

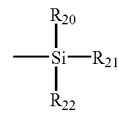

with the proviso that, if $G_2$=alkyl, the radical $G_2$ is attached directly to the silicon atom without an oxygen bridge; or $G_1$ and $G_2$ together are a single bond;

$R_{13}$, $R_{14}$, $R_{15}$, $R_{17}$, $R_{18}$, $R_{19}$, $R_{20}$, $R_{21}$ and $R_{22}$ independently of one another are $C_1$-$C_{18}$alkyl, phenyl, $C_2$-$C_6$hydroxyalkyl, $C_2$-$C_6$aminoalkyl or $C_5$-$C_8$cycloalkyl;

$R_{16}$ is unsubstituted $C_1$-$C_{18}$alkyl; $C_1$-$C_{18}$alkyl substituted by hydroxyl, $C_1$-$C_{12}$alkoxy, halogen, $C_3$-$C_8$cycloalkyl and/or $N(R_8)(R_9)$; unsubstituted phenyl; phenyl substituted by $C_1$-$C_{12}$alkyl, $C_1$-$C_{12}$alkoxy, halogen, hydroxyl and/or $N(R_8)(R_9)$; pr $C_5$-$C_8$cycloalkyl;

or

A, if s is more than 1, corresponds to a radical of the formula III in which n is the number s; or A, if s is 2, is a radical $A_1$; where $A_1$ is unsubstituted $C_6$-$C_{30}$alkylene, $C_6$-$C_{30}$alkenylene, $C_6$-$C_{30}$alkynylene, $C_6$-$C_{30}$aralkylene; OH—, $C_1$-$C_4$alkoxy-, phenyl-, naphthyl-, halogen-, CN—, $SR_7$—, $NR_8R_9$— and/or —O(CO)$R_{10}$-substituted $C_6$-$C_{30}$alkylene, $C_6$-$C_{30}$alkenylene, $C_6$-$C_{30}$alkynylene, $C_6$-$C_{30}$aralkylene; and these radicals are uninterrupted or interrupted by one or more —O—, —S— or —$NR_{12}$—;

r is 1 or 2; and, if r is 2, the compound of the formula I contains two radicals R which may be identical or different; with the proviso that if A is $A_0$ or $A_1$ r is 1;

s is a number from 1 to 1000; with the proviso that if A is $A_0$ or $A_1$ s is 1 or 2;

n is a number from 1 to 1000, or, where the siloxane starting material is a mixture of oligomeric siloxanes, n may also be less than 1 but greater than 0;

m is a number from 0 to 100;

p is a number 0-10 000;

x is 1, 2 or 3;

Y, if r=1 and x=1, is a divalent group $C_1$-$C_{10}$alkylene, $C_2$-$C_{10}$alkenylene, $C_2$-$C_{10}$alkynylene, —$(CH_2)_a$—O—, —$[(CH_2)_a$—O—$(CH_2)_b]_c$—, —$[(CH_2)_a$—O$]_d(CH_2)_b$—, —$(CH_2)_a$—O—$(CH_2)_b$—O—, —$(CH_2)_a$—$NR_8$—$(CH_2)_b$—, —$(CH_2)_a$—O—$(CH_2)_b$—$NR_8$—$(CH_2)_c$—, —$(C_2$-$C_{10}$alkenylene)—O—$(CH_2)_a$—, —$(C_2$-$C_{10}$alkynylene)—O—$(CH_2)_a$—, Y, if r=1 and x>1, is —$CR_{23}$—$[(CH_2)_b]_2$, —C—$[(CH_2)_b]_3$; $(CH_2)_a$—CH—$[(CH_2)_b]_2$; $(CH_2)_a$—C—$[(CH_2)_b]_3$; —$CR_{23}$—$[(CH_2)_a$—O—$(CH_2)_b]_2$; —C—$[(CH_2)_a$—O—$(CH_2)_b]_3$; $(CH_2)_a$—$CR_{23}$—$[(CH_2)_a$—O—$(CH_2)_b]_2$; $(CH_2)_a$—C—$[(CH_2)_a$—O—$(CH_2)_b]_3$ where $R_{23}$ is hydrogen or $C_1$-$C_4$alkyl, Y, if r=2,
is a trivalent group of the formulae:

Y-1

Y-2

Y-3

Y-4

Y-5

Y-6

Y-7

Y-8

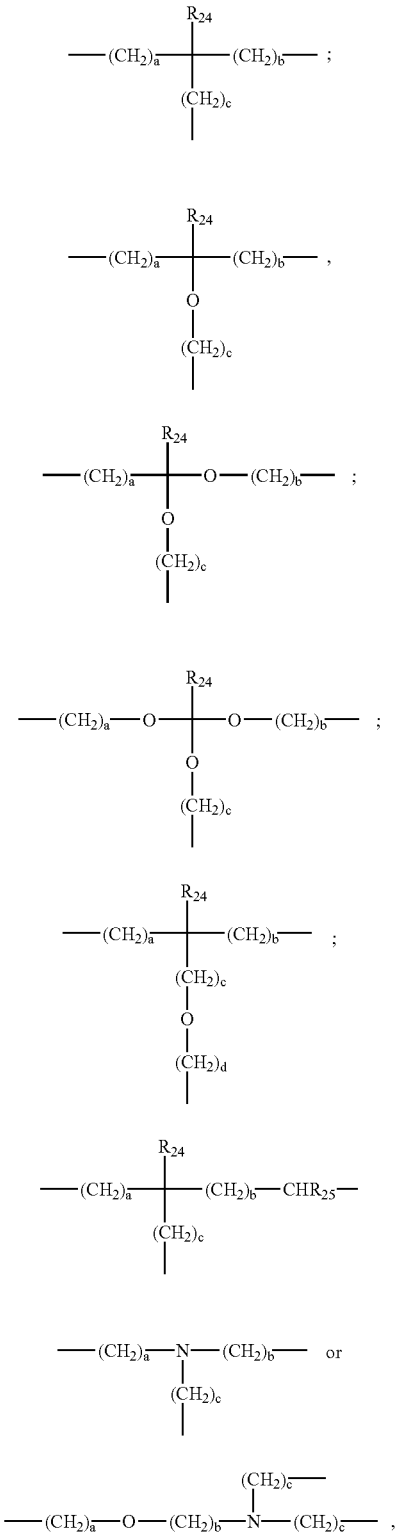

$R_{24}$ is hydrogen or $C_1$-$C_4$alkyl,
$R_{25}$ is $C_1$-$C_4$alkyl;

and at the site of a bond to the photoinitiator radical

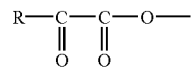

there must
always be at least one methylene group; and
Y, if A is $A_0$ or $A_1$, is a single bond;
a is a number from 1 to 10;
b, c and d independently of one another are a number from 0 to 10; with the proviso that they are, however, at least 1 if the methylene group in question is between two oxygen atoms or one oxygen and one nitrogen atom, and
q is a number from 1 to 10.

$C_1$-$C_{18}$Alkyl is linear or branched and is for example $C_1$-$C_{12}$-, $C_1$-$C_8$-, $C_1$-$C_6$- or $C_1$-$C_4$alkyl. Examples are methyl, ethyl, propyl, isopropyl, n-butyl, sec-butyl, iso-butyl, tert-butyl, pentyl, hexyl, heptyl, 2,4,4-trimethyl-pentyl, 2-ethylhexyl, octyl, nonyl, decyl, undecyl, dodecyl, tetradecyl, pentadecyl, hexadecyl, heptadecyl or octadecyl.

$C_1$-$C_{12}$Alkyl, $C_1$-$C_8$alkyl and $C_1$-$C_4$alkyl have the same definitions as indicated above but with the corresponding number of carbon atoms.

$C_6$-$C_{30}$Alkyl is likewise linear and branched and is for example $C_6$-$C_{24}$-, $C_6$-$C_{12}$-, $C_{10}$-$C_{30}$-, $C_{10}$-$C_{24}$-, $C_{12}$-$C_{30}$alkyl. Examples are hexyl, heptyl, 2,4,4-trimethylpentyl, 2-ethylhexyl, octyl, nonyl, decyl, undecyl, dodecyl, tetradecyl, pentadecyl, hexadecyl, heptadecyl, octadecyl, nonadecyl, icosyl, henicosyl, docosyl, tricosyl, tetracosyl, pentacosyl, hexacosyl, heptacosyl, octacosyl or triacontyl.

$C_2$-$C_{12}$Alkyl interrupted by one or more oxygen atoms is for example interrupted 1-9, 1-7 or 1 or 2 times by —O—. Where the radicals are interrupted by two or more —O—, the oxygen atoms are each separate from one another by at least one methylene group. This results, for example, in structural units such as —$CH_2$—O—$CH_3$, —$CH_2CH_2$—O—$CH_2CH_3$, —[$CH_2CH_2$O]$_y$—$CH_3$, where y=1-9, —($CH_2CH_2$O)$_7CH_2CH_3$, —$CH_2$—$CH(CH_3)$—O—$CH_2$—$CH_2CH_3$ or —$CH_2$—$CH(CH_3)$—O—$CH_2CH_3$.

$C_2$-$C_6$Hydroxyalkyl is $C_2$-$C_6$alkyl substituted by OH. The alkyl radical is linear or branched and may have the definitions indicated above (with the corresponding number of carbon atoms).

$C_2$-$C_6$Aminoalkyl is $C_2$-$C_6$alkyl substituted by $NH_2$. The alkyl radical is linear or branched and may have the definitions indicated above (with the corresponding number of carbon atoms).

$C_1$-$C_{12}$Alkoxy stands for linear or branched radicals and is for example $C_1$-$C_{10}$-, $C_1$-$C_8$-, $C_1$-$C_6$- or $C_1$-$C_4$alkoxy. Examples are methoxy, ethoxy, propoxy, isopropoxy, n-butyloxy, sec-butyloxy, iso-butyloxy, tert-butyloxy, pentyloxy, hexyloxy, heptyloxy, 2,4,4-trimethylpentyloxy, 2-ethylhexyloxy, octyloxy, nonyloxy, decyloxy or dodecyloxy, especially methoxy, ethoxy, propoxy, isopropoxy, n-butyloxy, sec-butyloxy, iso-butyloxy, tert-butyloxy, preferably methoxy. $C_1$-$C_4$Alkoxy is likewise linear or branched and has, for example, the definitions indicated above with the corresponding number of carbon atoms.

$C_3$-$C_8$-Cycloalkyl is linear or branched alkyl containing at least one ring, for example cyclopropyl, cyclopentyl, methyl-cyclopentyl, cyclohexyl, methyl- or dimethyl-cyclohexyl, or cyclooctyl, especially cyclopentyl and cyclohexyl.

$C_5$-$C_8$Cycloalkyl has the definitions indicated above with the corresponding number of carbon atoms.

$C_3$-$C_6$Alkenyl may be mono- or polyunsaturated and may be linear or branched and is for example $C_3$-$C_4$alkenyl. Examples are allyl, methallyl, 1,1-dimethylallyl, 1-butenyl, 2-butenyl, 1,3-pentadienyl or 1-hexenyl, especially allyl.

$C_6$-$C_{30}$Alkenyl is likewise linear or branched and mono- or polyunsaturated and is for example $C_6$-$C_{24}$-, $C_6$-$C_{12}$-, $C_{10}$-$C_{30}$-, $C_{10}$-$C_{24}$-, $C_{12}$-$C_{30}$alkenyl. Examples are hexenyl, heptenyl, 2,4,4-trimethyl-pentenyl, 2-ethylhexenyl, octenyl, nonenyl, decenyl, undecenyl, dodecenyl, tetradecenyl, pentadecenyl, hexadecenyl, heptadecenyl, octadecenyl, nonadecenyl, icosenyl, henicosenyl, docosenyl, tricosenyl, tetracosenyl, pentacosenyl, hexacosenyl, heptacosenyl, octacosenyl or triacontenyl.

$C_6$-$C_{30}$Alkynyl is linear or branched and mono- or polyunsaturated and is for example $C_6$-$C_{24}$-, $C_6$-$C_{12}$-, $C_{10}$-$C_{30}$-, $C_{10}$-$C_{24}$-, $C_{12}$-$C_{30}$alkinyl. Examples are hexynyl, heptynyl, 2,4,4-trimethyl-pentynyl, 2-ethylhexynyl, octynyl, nonynyl, decynyl, undecynyl, dodecynyl, tetradecynyl, pentadecynyl, hexadecynyl, heptadecynyl, octadecynyl, nonadecynyl, icosynyl, henicosynyl, docosynyl, tricosynyl, tetracosynyl, pentacosynyl, hexacosynyl, heptacosynyl, octacosynyl or triacontynyl.

$C_6$-$C_{30}$Aralkyl is alkyl substituted by an aromatic radical. Examples are phenyl-$C_1$-$C_{24}$alkyl, naphthyl-$C_1$-$C_{20}$alkyl, anthryl-$C_1$-$C_{16}$alkyl, phenanthryl-$C_1$-$C_{16}$alkyl, the corresponding alkyl radical $C_1$-$C_{24}$, $C_1$-$C_{20}$, $C_1$-$C_{16}$ in each case being substituted by the respective corresponding aromatic radical phenyl, naphthyl, anthryl or phenanthryl. The alkyl radicals are linear or branched and may have the definition indicated above. Examples are benzyl, phenylethyl, α-methylbenzyl, phenylpentyl, phenylhexyl oder α,α-dimethylbenzyl, especially benzyl, naphthylmethyl, naphthylethyl, naphthylpropyl or naphthyl-1-methylethyl, in particular naphthylmethyl. The alkyl unit may be in either 1 position or 2 position on the naphthyl ring system.

Halogen is fluorine, chlorine, bromine and iodine, especially chlorine and bromine, preferably chlorine.

Substituted phenyl is substituted from one to five times, for example once, twice or three times, especially once or twice, on the phenyl ring.

A heterocyclic radical in this context includes not only aliphatic but also aromatic rings containing one or more, especially one or two, heteroatoms. Fused ring systems are included. Examples of suitable heteroatoms include particularly O, N or S. Examples are furyl, thienyl, pyrrolyl, oxinyl, dioxinyl or pyridyl. 5- or 6-membered rings are preferred. As a heterocyclic radical R is for example pyrrolyl, pyrrolidinyl, oxazolyl, pyridinyl, 1,3-diazinyl, 1,2-diazinyl, piperidinyl, morpholinyl, thianthrenyl, furanyl, pyranyl, xanthenyl, imidazolyl thiazoylyl, pyrimidinyl, indazolinyl, indolyl, indazolyl, purinyl, isoquinolyl, quinolyl, xanthyl, thioxanthyl, acridinyl etc.

Where $OR_6$-, $SR_7$- or $NR_8R_9$-substituted naphthyl, anthracyl, phenanthryl or heterocyclic rings form 5- or 6-membered rings via the radicals $R_6$, $R_7$, $R_8$ and/or $R_9$ with further substituents on the naphthyl, anthracyl or phenanthryl ring or on the heterocycle or with one of the carbon atoms of the naphthyl, anthracyl or phenanthryl ring or with one of the carbon atoms of the heterocycle, this embraces for example the following structures

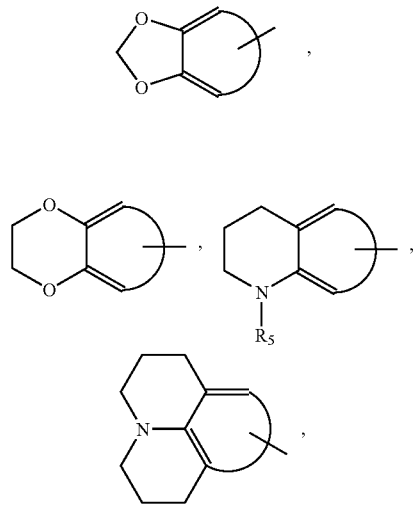

in which the arc and the two double bonds are the aromatic ring system in question.

Where $R_1$, $R_2$, $R_3$, $R_4$ or $R_5$ as $OR_6$, $SR_7$ or $NR_8R_9$ form a 5- or 6-membered ring with further substituents on the phenyl ring or with a carbon atom of the phenyl ring, this includes for example the following systems:

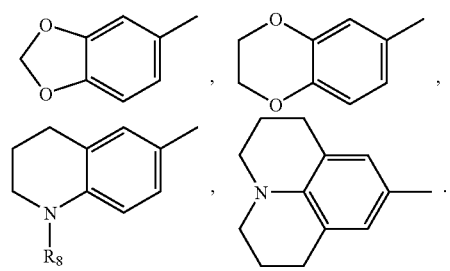

Where $R_8$ and $R_9$, together with the nitrogen atom to which they are attached, form a 5- or 6-membered ring which may also be interrupted by —O— or —$NR_{12}$—, the rings in question are, for example, saturated or unsaturated rings, examples being aziridine, piperazine, pyrrole, pyrrolidine, oxazole, pyridine, 1,3-diazine, 1,2-diazine, piperidine or morpholine; in particular, morpholinyl, piperidinyl or piperazinyl rings are formed.

The units of the formulae IIIa, IIIb and/or IIIc are arranged randomly or in blocks; i.e. the sequence of these units in the depiction of the formula III is arbitrary. For example, blocks of units of the formula IIIa, IIIb, IIIc may follow one another, but it is also possible for the individual units to be linked in a randomly distributed fashion, depending on the siloxane used for the preparation.

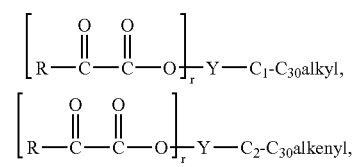

-continued $$\left[R-\overset{O}{\overset{\|}{C}}-\overset{O}{\overset{\|}{C}}-O\right]_r-Y-C_2-C_{30}\text{alkynyl} \quad \text{each represent}$$

$$\left[R-\overset{O}{\overset{\|}{C}}-\overset{O}{\overset{\|}{C}}-O\right]_r-Y\text{-substituted}$$

$C_1$-$C_{30}$alkyl, $C_2$-$C_{30}$alkenyl or $C_2$-$C_{30}$alkynyl. The definitions of the alkyl, alkenyl and alkynyl radicals have been given above.

$C_1$-$C_{10}$Alkylene Y is linear or branched alkylene, for example $C_1$-$C_8$-, $C_1$-$C_6$-, $C_1$-$C_4$-, $C_2$-$C_8$-, $C_2$-$C_4$alkylene, such as methylene, ethylene, propylene, isopropylene, n-butylene, sec-butylene, iso-butylene, tert-butylene, pentylene, hexylene, heptylene, octylene, nonylene or decylene. In particular, Y is $C_1$-$C_8$alkylene, for example ethylene, octylene, $$-\overset{H}{\underset{C_7H_{15}}{C}}- \ , \quad -\overset{}{\underset{CH_3}{CH}}-CH_2- \ , \quad -\overset{}{\underset{CH_3}{CH}}-(CH_2)_2- \ ,$$

$$-\overset{}{\underset{CH_3}{CH}}-(CH_2)_3- \ , \quad -C(CH_3)_2-CH_2- \quad \text{or}$$

$$-CH_2-\overset{C_2H_5}{\underset{CH_3}{\overset{|}{C}}}-CH_2- \ .$$

$C_2$-$C_{10}$Alkenylene is mono- or polyunsaturated, linear or branched and is for example $C_2$-$C_8$-, $C_3$-$C_6$-, $C_2$-$C_4$alkenylene, for example ethenylene, 1-propenylene, 1-butenylene, 3-butenylene, 2-butenylene, 1,3-pentadienylene, 5-hexenylene or 7-octenylene.

$C_2$-$C_{10}$Alkynylene is mono- or polyunsaturated, linear or branched and is for example $C_2$-$C_8$-, $C_3$-$C_6$-, $C_2$-$C_4$alkynylene. Examples are hexynylene, heptynylene, 2,4,4-trimethylpentynylene, 2-ethylhexynylene, octynylene, nonynylene or decynylene.

The term "from 200 nm into the IR region" denotes from 200 nm to 2500 nm, in particular from 200 nm to 1000 nm.

The term "and/or" is intended to denote that it is possible for not only one of the defined alternatives (substituents) to be present but also two or more different alternatives (substituents) of those defined together, i.e. mixes of different alternatives (substituents).

The term "at least" is intended to define one or more than one, for example one or two or three, preferably one or two.

Unless expressly described otherwise, in the description and the claims the word "comprising" is to be understood to include a defined subject or a defined group of subjects but without ruling out any other substances not mentioned exclusively.

If r is 2 and Y is a trivalent group, there must always be at least one methylene group at the attachment to the photoinitiator radical $$R-\overset{O}{\overset{\|}{C}}-\overset{O}{\overset{\|}{C}}-O-\ ,$$

i.e., if the linkage at a site is via $(CH_2)_b$ or $(CH_2)_c$ groups, b and/or c are at least 1.

"a" is preferably a number from 1 to 10, especially 1-3;

"b" and "c" are preferably a number from 0 to 10, especially 1-3;

"n" is preferably from 1 to 100; especially 1-20;

"p" is for example from 1 to 1000, from 1 to 100, from 1 to 50 or from 1 to 25; and "m" is from 0 to 100, for example from 0 to 50 or from 0 to 25, especially 0.

Where the siloxane starting material is a mixture of oligomeric siloxanes, "n" can also be less than 1 but greater than 0. In this case it is for example a number between 0.1 and 1000; 0.5 and 1000; 0.8 and 1000 etc.

"r" is preferably 1. Where "r" is 2, the two groups $$R-\overset{O}{\overset{\|}{C}}-\overset{O}{\overset{\|}{C}}-O-$$

may be identical or different, i.e. contain identical or different radicals R. In this case the radicals R are preferably identical.

R in particular is a radical of the formula II or is naphthyl, and is preferably a radical of the formula II.

$R_1$, $R_2$, $R_3$, $R_4$ and $R_5$ are especially hydrogen, $C_1$-$C_4$alkyl or $C_1$-$C_4$alkoxy. Preferably all of $R_1$—$R_5$ are hydrogen.

$R_6$ and $R_7$ are especially hydrogen, $C_1$-$C_4$alkyl; unsubstituted or $C_1$-$C_4$alkyl- and/or $C_1$-$C_4$alkoxy-substituted phenyl, or —O-interrupted $C_2$-$C_8$alkyl, preferably $C_1$-$C_4$alkyl or hydrogen.

$R_8$ and $R_9$ are especially $C_1$-$C_4$alkyl, preferably methyl, or together with the nitrogen atom to which they are attached form a morpholinyl radical.

$R_{10}$ is especially $C_1$-$C_4$alkyl or phenyl.

$R_{11}$ is preferably $C_1$-$C_4$alkyl or phenyl.

$R_{12}$ is preferably hydrogen, $C_1$-$C_4$alkyl or OH-substituted $C_1$-$C_4$alkyl.

$R_{13}$, $R_{14}$ and $R_{15}$ are preferably $C_1$-$C_4$alkyl, especially methyl.

$R_{16}$ is especially $C_1$-$C_4$alkyl, for example methyl.

Y is preferably $C_3$-$C_6$alkylene, —$(CH_2)_a$—O— or —$(CH_2)_a$—O—$(CH_2)_b$—, especially $C_3$-$C_6$alkylene or —$(CH_2)_a$—O—$(CH_2)_b$—, a being particularly 2 and b being particularly 3.

A is especially a radical of the formula III, preferably a radical of the formula III, in which x is 1.

"x" is especially 1 or 2.

$A_0$ is in particular a $C_6$-$C_{30}$alkyl radical which is unsubstituted or substituted by halogen. $A_0$ is preferably $C_{12}$-$C_{30}$alkyl unsubstituted or substituted by halogen, preferably fluorine.

Where $C_6$-$C_{30}$alkyl, $C_6$-$C_{30}$alkenyl, $C_6$-$C_{30}$alkynyl or $C_6$-$C_{30}$aralkyl are substituted by they are preferably substituted by fluorine. Preference is given to perfluorinated alkyl radicals or $CF_3$-substituted alkyl radicals, especially perfluorinated alkyl radicals. Examples are octadecyl, octaicosyl and perfluorodecyl ($C_{10}F_{21}$).

$A_1$ is preferably a $C_6$-$C_{30}$alkylene radical which is unsubstituted or substituted by halogen. $A_1$ is preferably $C_{12}$-$C_{30}$alkylene unsubstituted or substituted by halogen, preferably fluorine.

Where $C_6$-$C_{30}$alkylene, $C_6$-$C_{30}$alkenylene, $C_6$-$C_{30}$alkynylene or $C_6$-$C_{30}$aralkylene are substituted by halogen, they are preferably substituted by fluorine. Preference is given to perfluorinated alkyl radicals or $CF_3$-substituted alkyl radicals, especially perfluorinated alkyl radicals. Examples are dodecylene, hexadecylene and perfluorobutylene ($C_4F_8$).

The compounds of the formula I are prepared by customary methods known to the person skilled in the art.

For instance, compounds of the formula I in which A is a radical of the formula III may be obtained in a variety of ways; for example, they may be prepared by reacting a photoinitiator with (at least one) alkenyl radical (IV) or (IVa) and a siloxane (V) in the presence of an appropriate catalyst:

Moreover, it is appropriate to carry out the reaction, for example, in a suitable aprotic organic solvent, such as tetrahydrofuran (THF), dioxane, hexane, heptane, cyclohexane, toluene, xylene, benzene or chlorobenzene. It is also possible, however, to operate without solvents.

The reaction mixture is normally stirred while the reaction is carried out. It is also appropriate to carry out the reaction under inert conditions, for example under an argon or nitrogen atmosphere.

Examples of catalysts appropriate for carrying out the reaction are noble metal catalysts, such as platinum or rhodium catalysts. Examples of platinum catalysts are $H_2PtCl_6$ or $PtCl_2(C_6H_5-CH=CH_2)_2$. These catalysts may also, for example, have been applied to suitable support materials, such as alumina, such as $Pt/Al_2O_3$ (for example, available from Heraeus). Carbon, for example, may also be used as a support material (Pt/C—which catalyst need not be

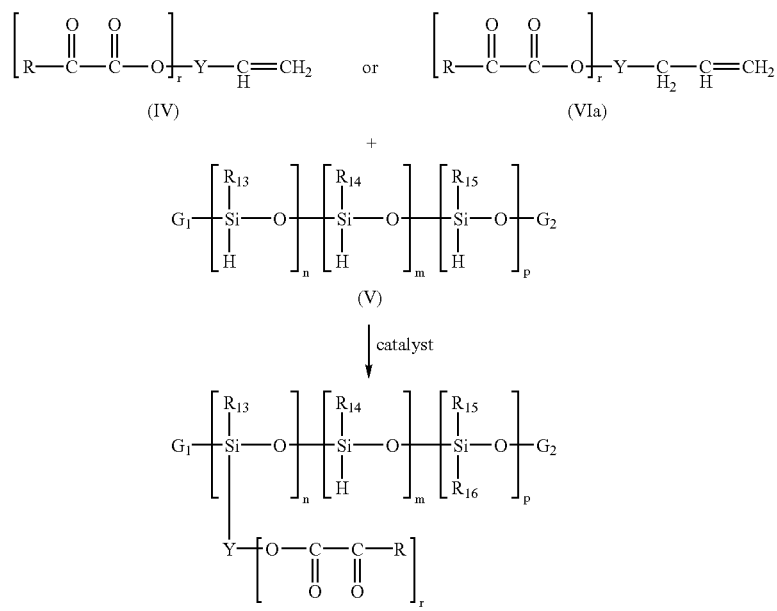

in which Y, R, $R_{13}$, $R_{14}$, $R_{15}$, $R_{16}$, Y, $G_1$, $G_2$, n, m, p and r are as defined above.

In order to prepare compounds of the formula I where r=2, appropriately modified photoinitiators are used, i.e. those having, for example, 2 alkylene units.

Such reactions are described, for example, in U.S. Pat. No. 4,507,187. Conditions for such reactions are known to the person skilled in the art. The molar ratios between the alkenyl-modified compound (IV) and the siloxane compound (V) are guided in each case by the desired product and are generally not critical. For instance, the amount of (IV) to be used is chosen according to the amount of free Si—H groups in (V) and the respective desired degree of substitution of these groups. Where all the groups are to be consumed by reaction, it is appropriate, for example, to add (IV) in excess. It is, however, also possible to use an excess of component (V).

The reaction temperatures are appropriately held within a range of 20-150° C., preferably 60-110° C.

anhydrous—available, for example, from Johnson Matthey). Examples of suitable catalysts are platinum, palladium, rhodium, nickel, cobalt or other metals, especially as powders or in the form of complexes. Examples are platinum sponge, platinum black, chloroplatinic acid, the reaction product of chloroplatinic acid and alcohol, and a complex of chloroplatinic acid and vinylsiloxane.

Catalysts of this kind are available commercially, e.g. platinum carbonyl-cyclovinylmethylsiloxane complex, platinum-divinyltetramethyldisiloxane complex, platinum-octyl aldehyde/octanol complex, or may be obtained by methods customary in the art and known to the person skilled in the art.

The concentration of the catalyst is appropriately for example 1-1 000 ppm, e.g. 150-400 ppm.

Another way of preparing the surface-active photoinitiators is to react a photoinitiator containing a corresponding silyl group with an alkenyl-modified siloxane:

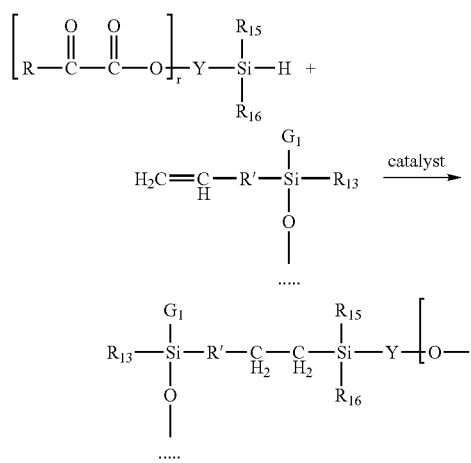

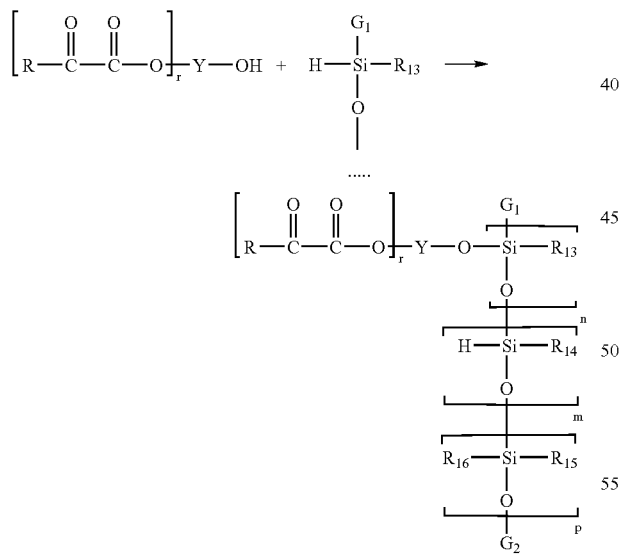

R, $R_{13}$, $R_{15}$, $R_{16}$, Y, $G_1$ and r have the definitions stated above; R' is an alkylene radical; " . . . " means that the radical of the siloxane molecule moiety defined in formula III adjoins this site (in accordance with formula III in this reaction m must be 0 in the starting material). The reaction conditions for this method correspond to those described above. In the literature such reactions are set out, for example, in U.S. Pat. No. 4,391,963 and JMS Pure Applied Chem. A31(3) (1994), 305.

The surface-active photoinitiators may also be obtained, for example, by reacting an OH-containing initiator and a siloxane:

R, Y, r, $G_1$, $G_2$, $R_{13}$, $R_{14}$, $R_{15}$, $R_{16}$, n, m and p have the definitions stated above; " . . . " means that the radical of the siloxane molecule moiety defined in formula III adjoins this site.

Suitable catalysts for this reaction are, for example, tin octoate, dibutyltin dilaurate, zinc octanoate, tin octanoate and zinc hexanoate. Examples of such reactions (albeit with the examples containing a sensitizer unit instead of the photoinitiator unit) can be taken from U.S. Pat. No. 4,921,589.

L. Lecamp et al. in JMS Pure Appl. Chem. A 34(11) (1997), 2335-2353 describe a method of preparing siloxane initiators in which an initiator comprising an $Si(OR)_{1-3}$ group and a siloxane having an Si—$(OH)_{1-2}$ group are reacted. Dibutyltin dilaurate, for example, is used as catalyst:

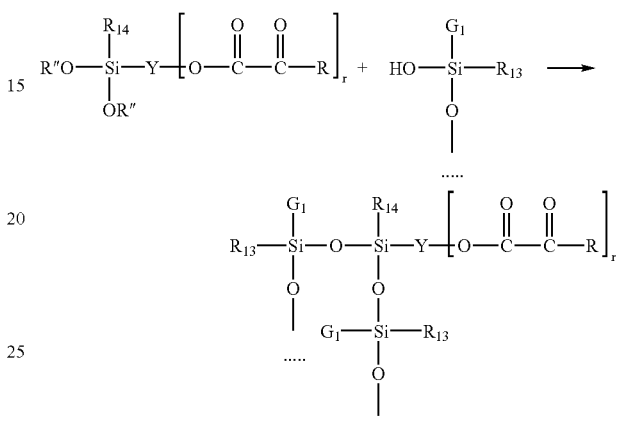

R, Y, r, $R_{13}$, $R_{14}$, and $G_1$ have the definition indicated above; R" ist alkyl, especially methyl; " . . . " means that the radical of the siloxane molecule moiety defined in formula III adjoins this site.

U.S. Pat. No. 4,477,326 and JP 9-328522-A describe the polymerization or copolymerization of polyalkoxysiloxanes in the presence of a base or of an acid catalyst. The method described is also suitable for preparing surface-active initiators:

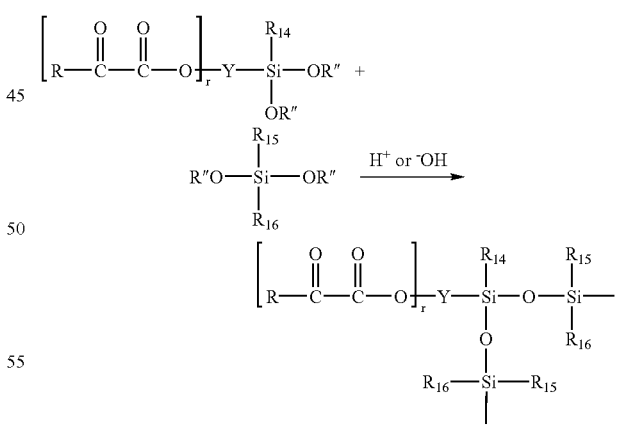

R, r, Y, $R_{14}$, $R_{16}$, $R_{15}$ have the definition indicated above; R" is alkyl. In this reaction, both polymeric and cyclic products are obtained.

Another method which can be used to prepare surface-active photoinitiators is set out, for example, in U.S. Pat. No. 4,587,276 and U.S. Pat. No. 4,477,276: the polymerization or copolymerization of siloxanes having hydrolysable groups (e.g. Si—Cl) in the presence of water:

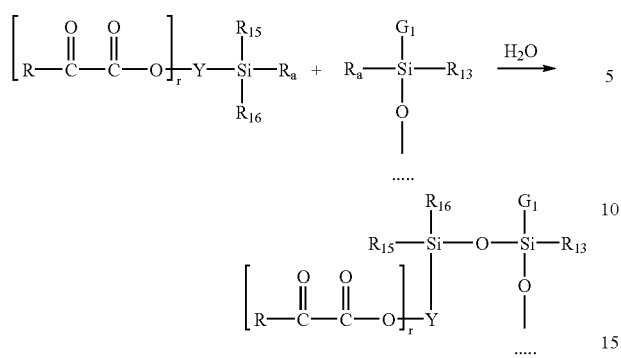

R, r, Y, $R_{15}$, $R_{16}$, $R_{13}$, and G, have the definition indicated above; $R_a$ is, for example, Cl or $OCH_3$; " . . . " means that the radical of the siloxane molecule moiety defined in formula III adjoins this site.

In J. M. S. Pure Appl. Chem. A 31(3) (1994), 305-318 A. Kolar et al. describe the preparation of photoinitiators with siloxane radicals starting from 1,4-dichlorobenzene. Grignard reaction is used to create a reactive centre which is reacted with dimethyl dichlorosilane or dimethylmonochlorosilane to the corresponding silyl-modified chlorobenzene, onto which the photoinitiator carbonyl radical is introduced by means of further reactions.

L. Pouliquen et al. in Makromol. Chem. 193 (1992) 1273-1282 published a multistage reaction of photoinitiators containing acidic groups and a siloxane containing epoxide radicals in the presence of acetic anhydride (the photoinitiator compounds in this reference are of the phenone/tert-amine type).

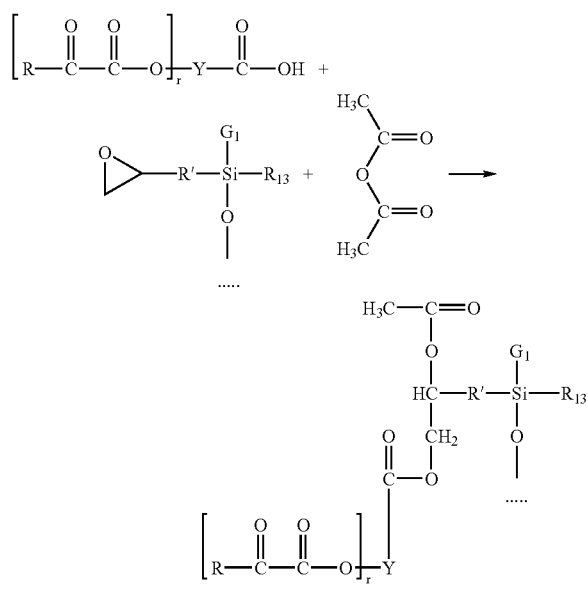

R, r, Y, $G_1$, and $R_{13}$ have the definition indicated above, R' is alkylene; " . . . " means that the radical of the siloxane molecule moiety defined in formula III adjoins this site.

The compounds of the formula I in which A is a surface-active siloxane radical of the formula III may also be prepared by reacting the corresponding glyoxalic acid with a siloxane having carbinol radicals, a siloxane having halocarbon radicals or a siloxane having epoxide radicals:

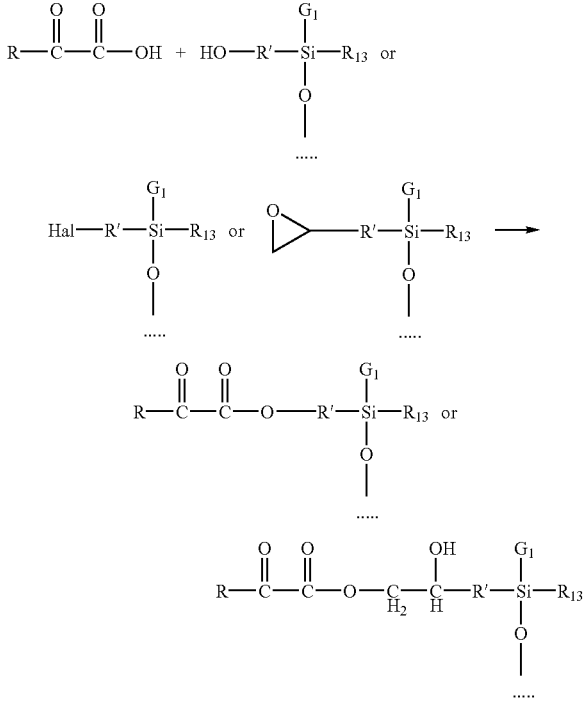

The reaction proceeds in the presence of an acid or of a base.

R, $G_1$, and $R_{13}$ have the definition indicated above.

R' is alkylene. " . . . " means that the radical of the siloxane molecule defined in formula III adjoins this site.

Photoinitiators containing isocyanate groups and siloxanes containing hydroxyl or amine groups may likewise be reacted to give surface-active photoinitiators:

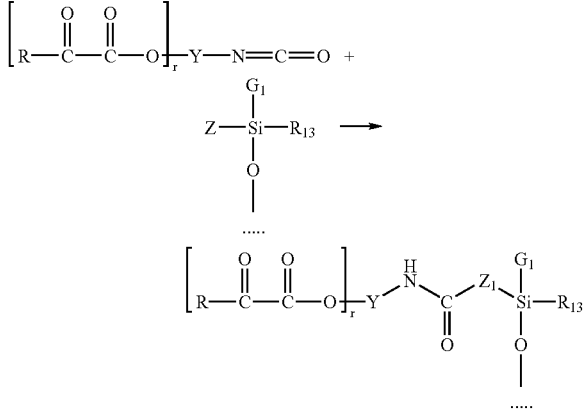

R, r, Y, $G_1$, and $R_{13}$ have the definitions indicated above; Z is $NH_2$ or OH; $Z_1$ is NH or O; " . . . " means that the radical of the siloxane molecule moiety defined in formula III adjoins this site. Such reactions are described, for example, in WO 96/20919.

The compounds of the formula I in which A is a surface-active siloxane radical of the formula III may also be prepared by reacting the corresponding glyoxaloyl chloride with a hydroxy-siloxane:

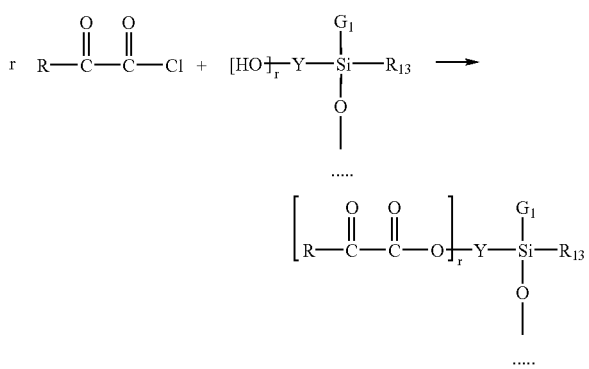

R, r, Y, $G_1$ and $R_{13}$ have the definitions indicated above; ..... means that the radical of the siloxane molecule moiety defined in formula III adjoins this site.

Photoinitiators substituted by cyclic siloxane radicals may be obtained, for example, by carrying out the reactions described above with a cyclic siloxane, for example with a siloxane of the formula

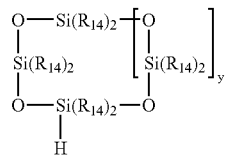

To prepare photoinitiators with cyclic siloxane radicals it is, however, also possible first to introduce linear siloxane radicals, by means for example of the methods described above, and then to cyclize these radicals by the action of a base, for example sodium hydroxide, or by the action of an acid.

The synthesis of surface-active photoinitiators containing cyclic siloxane radicals may take place, for example, as described above by reacting a cyclic siloxane with the respective initiator moiety:

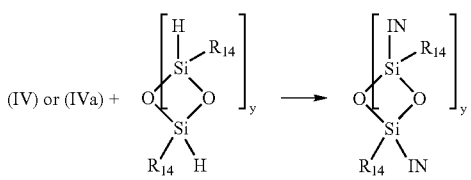

(IN and $R_{14}$ are as defined above; y defines the ring size) or by cyclizing reaction of a siloxane-modified initiator moiety containing OR groups in the presence of acid or alkali:

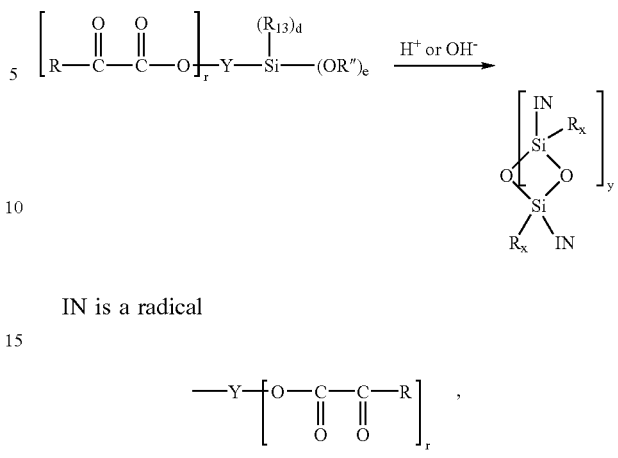

IN is a radical $R_{13}$, R, Y and r are as defined above; R" is alkyl; d=0 or 1; e=2 or 3, and the sum d+e=3; depending on the definition of d and e, $R_x$ is either $R_{13}$ or OR".

It is also conceivable to react compounds where d=2 and e=1 in this way; in that case, however, the resulting compounds are linear rather than cyclic compounds of the invention. Furthermore, cyclic compounds may be formed by reacting a siloxane-modified initiator moiety containing OR groups with a siloxane containing OR groups:

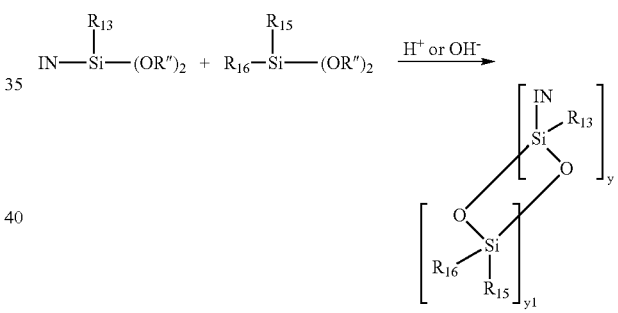

(IN, $R_{13}$, $R_{15}$, $R_{16}$ are as defined above; R" is alkyl; the sum of y and y1 defines the number of ring members)

The distribution of the Si(IN)($R_{13}$) and Si($R_{15}$)($R_{16}$) groups in this case is random or blockwise.

Of course, in the preparation of the compounds of the formula I it is also possible for mixtures to be formed. These may be separated in accordance with the customary separation methods known to the person skilled in the art, for example by distillation, crystallization or chromatographic techniques. Alternatively, the mixtures may be used as they are, without prior separation, in the process of the invention.

The alkenyl-modified photoinitiators (IV) and (IVa) may be prepared by methods known to the person skilled in the art, for example by the method described in U.S. Pat. No. 4,507,187 or in EP 161830. Appropriate methods are also published in WO 98/33761.

Some of the siloxane compounds (V) are available commercially, or they may be obtained by methods known to the person skilled in the art. For example, methods of preparation and/or literature citations for the preparation can be found in the Geleste catalogue "ABCR Geleste 2000", pages 434-447.

Compounds of the formula I in which A is a surface-active radical $A_0$ or $A_1$, i.e. those compounds of the formula I which do not contain a siloxane radical, are likewise accessible by customary methods known to the person skilled in the art.

I. For example, they may be obtained by esterifying the corresponding glyoxalic acid compound under esterification conditions common in the art, for example in the presence of an acid or of coupling reagents of the Mitsunobu type, e.g. N,N'-dicyclohexylcarbodiimide (DCC) or 1,1'-carbonyldiimidazole (CDI) (coupling reagents of the Mitsunobu type are well known to the person skilled in the art and are described, for example, in "Progress in the Mitsunobu reaction. A review. Org. Prep. Proced. Int. (1996), 28(2), 127-64" or "The Mitsunobu reaction. Org. React. (N.Y.) (1992), 42 335-656"):

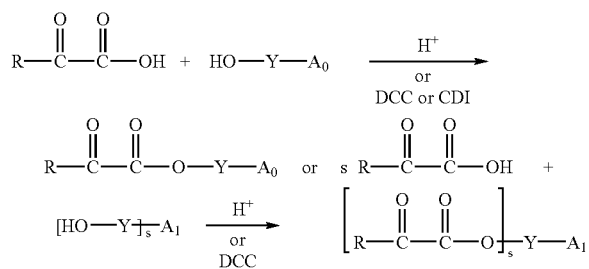

s, R, Y, $A_0$ and $A_1$ have the definition indicated above.

II. Another possibility of preparing the compounds of the formula I which contain no siloxane radical is the reaction of alcohols with glyoxalic esters, such as the corresponding methyl ester, in the presence of a catalyst:,

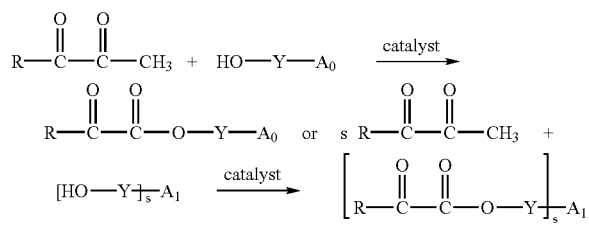

R, s, Y, $A_0$ and $A_1$ have the definition indicated above. Such compounds were described, for example, by Neckers et al in Tetrahedron 53 (21) (1997) 7165 or are part of the teaching of U.S. Pat. No. 4,024,297.

The catalysts used include, for example, the catalysts well known to the person skilled in the art for transesterification reactions, such as dibutyltin oxide or p-toluenesulfonic acid.

III. Another possibility of obtaining the compounds of the invention having a surface-active radical $A_0$ and/or $A_1$ is the base-catalyzed reaction of arylglyoxaloyl halides, preferably the chlorides, with an alcohol:

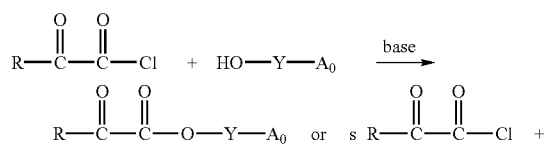

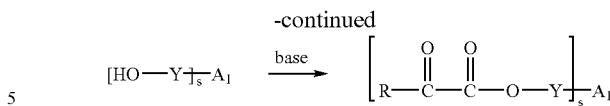

R, s, Y, $A_1$ and $A_0$ have the definitions described above.

The bases to be used for such reactions are well known to the person skilled in the art. Aqueous bases must not be used. Examples of suitable bases are carbonates, tert-amine bases, such as triethylamine, or pyridine.

IV. Furthermore, the compounds of the invention having surface-active radicals $A_0$ or $A_1$ may be obtained, for example, by reacting alcohols with corresponding arylacetic esters in the presence of a catalyst, with subsequent oxidation:

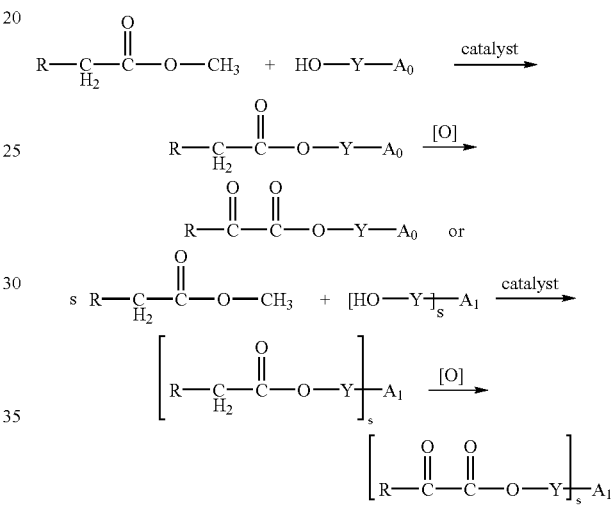

R, s, Y, $A_1$ and $A_0$ have the definitions described above.

The catalysts used are, for example, the catalysts which are well known to the person skilled in the art for transesterification reactions, such as dibutyltin oxide or p-toluenesulfonic acid. The oxidation step may take place, for example, as described in *J. Chem. Soc. Chem. Comm.* (1993), 323 or in *Synthesis* (1994), 915.

V. An example of a further suitable method of preparing the compounds of the invention of the formula I having a surface-active radical $A_0$ or $A_1$ is the reaction of corresponding hydroxy-substituted arylacetic esters with alcohols, with subsequent oxidation:

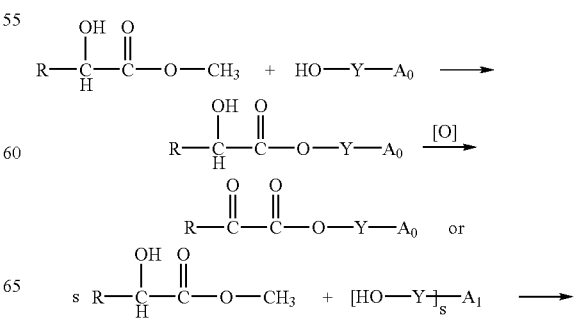

-continued

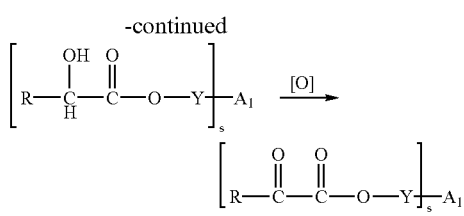

R, s, Y, $A_1$ and $A_0$ have the definitions described above.

The oxidation may be carried out, for example, in accordance with the method described in *J. Chem. Soc. Chem. Comm.* (1994), 1807.

VI. A further preparation possibility for the compounds of the formula I of the invention having a surface-active radical $A_0$ or $A_1$ is the acid-catalyzed reaction of arylcarboxylic cyanides with alcohols:

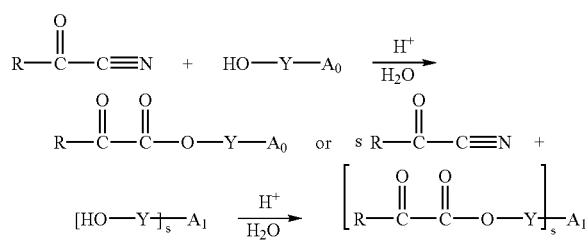

R, s, Y, $A_0$ and $A_1$ have the definitions described above.

VII. The compounds of the formula I of the invention having a surface-active radical $A_0$ or $A_1$ may also be obtained, for example, by Friedel-Crafts reaction of aryls with oxocarboxylic chlorides in the presence of aluminium chloride:

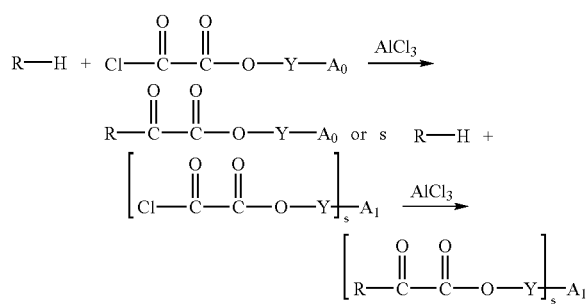

R, s, Y, $A_0$ and $A_1$ have the definitions indicated above.

Catalysts which can be used are the customary catalysts, well known to the person skilled in the art, for Friedel-Crafts reactions, examples being tin chloride, zinc chloride, aluminium chloride, titanium chloride or acidic earths.

In the preparation of asymmetric compounds of the formula I, i.e. those in which s is 2 and the two groups R and Y each have different meanings, the reaction is carried out using the corresponding different starting materials, appropriately in a ratio of 1:1.

The reactions I, II, IV and V may generally be carried out without using a solvent, with one of the liquid reaction components, for example the alcohol, serving as solvent. It is, however, also possible to conduct the reactions in an inert solvent. Suitable solvents are, for example, aliphatic or aromatic hydrocarbons such as, for example, alkanes and alkane mixtures, cyclohexane, benzene, toluene or xylene. The boiling point of these solvents should, though, be above that of the alcohol which forms during the reaction.

The other syntheses set out above are appropriately conducted in an inert solvent. Suitable examples include those indicated above. In the case of reaction I it is appropriate to ensure that the water which forms during the reaction is removed from the reaction mixture. In the case of reactions II, IV and V it is appropriate to ensure that the alcohol which forms during the reaction is removed from the reaction mixture. This is done, for example, by distillation. The reactions are conducted at different temperatures depending on the solvents and starting materials used. The temperatures and other reaction conditions required for the corresponding reactions are common knowledge and are well known to the person skilled in the art.

The reaction products may be separated and purified by customary methods, such as by crystallization, distillation or chromatography.

The preparation of the starting materials required for the synthesis of the compounds of the formula I of the invention is common knowledge and is well known to the person skilled in the art. Indeed, some of the compounds are available commercially.

For example, the arylglyoxalic esters are obtained by Friedel-Crafts reaction from the aryls and the corresponding oxocarboxylic methyl ester chloride, or by esterification of arylglyoxaloyl chlorides with alcohols.

Arylglyoxaloyl chlorides may be obtained, for example, by chlorination of the corresponding acid using, for example, $SOCl_2$. Arylcarboxylic cyanides may be obtained, for example, by reacting the corresponding acid chlorides with CuCN.

Arylacetic methyl esters are preparable, for example, by acid-catalyzed reaction of aryl-$CH_2$—CN with methanol. This reaction is described, for example, in *Org. Syn. Coll. Vol. I,* 270. The corresponding aryl-$CH_2$-cyanides may be obtained, for example, from the corresponding chlorides using NaCN, as disclosed, for example, in *Org. Syn. Coll. Vol. I,* 107 and *Org. Syn. Coll. Vol IV,* 576.

The synthesis of arylacetic ethyl esters can be found, for example, in *J. Chem. Soc. Chem. Comm.* (1969), 515, where the corresponding aryl bromide is reacted with $N_2CH_2COOC_2H_5$ in the presence of Li/diethyl ether, CuBr. Another method, the reaction of aryl bromides with ethyl acetate and NaH, is described, for example, in *J. Am. Chem. Soc.* (1959) 81, 1627 *J. Org. Chem.* (1968) 33, 1675 sets out the Grignard reaction of aryl bromides with $BrCH_2COOC_2H_5$ to give the arylacetic ethyl ester.

The preparation of the alcohols is well known to the person skilled in the art and is widely described in the literature. Many of these compounds are available commercially.

The preparation of the photoinitiator starting materials which in accordance with the invention are surface-actively modified with A or $A_0$ is known to the person skilled in the art and is performed in accordance with customary methods. The preparation of the glyoxalic ester initiators, for example, is described in U.S. Pat. No. 4,475,999, U.S. Pat. No. 4,038,164, EP 132868, GB 1534320, U.S. Pat. No. 4,279,718, U.S. Pat. No. 4,308,394, U.S. Pat. No. 3,930,868 and WO 98/33761.

The invention also provides novel compounds of the formula I.

The following novel compounds are of particular interest:
Compounds of the formula I in which R=phenyl; r=1; s=1; and A-1 A is a radical of the formula III, in which n=1; m=0; p=0; x=1; $G_1$=—O—Si—$(CH_3)_3$; $G_2$=—Si—$(CH_3)_3$.

formula I/A-1

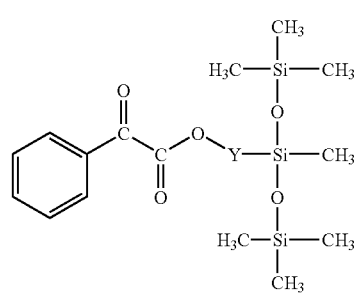

Compound A, compound of the formula I/A-1 where Y=—$(CH_2)_3$—;
Example 1, compound of the formula I/A-1 where Y=—$(CH_2)_6$—;
Example 5, compound of the formula I/A-1 where Y=—$(CH_2)_4$—;
Example 6, compound of the formula I/A-1 where Y=—$(CH_2)_2$—O—$(CH_2)_3$—;
Example 25, compound of the formula I/A-1 where Y=—$(CH_2$—$CH_2$—O$)_4$—$(CH_2)_3$—

A-2 A is a radical of the formula III, in which n=1; m=0; p=0; x>1; $G_1$=—O—Si—$(CH_3)_3$; $G_2$=—Si—$(CH_3)_3$ formula I/A-2

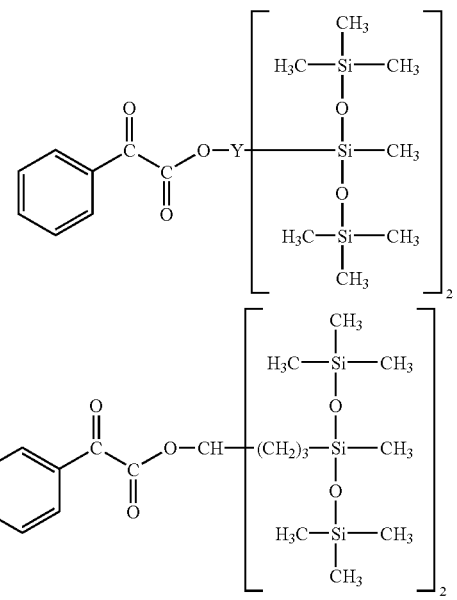

Example 10, Y=—(CH)—((CH$_2$)$_3$—)$_2$; x=2
Example 12, Y=—$CH_2$—C($C_2H_5$)—($CH_2$—O—($CH_2$)$_3$—)$_2$; x=2
Example 17, Y=—$CH_2$—C—($CH_2$—O—($CH_2$)$_3$—)$_3$; x=3
A-3 A is a Radical of the Formula III, in which n=1; m=0; p=1; x=1; $G_1$=$CH_3$; $G_2$=—Si—$(CH_3)_3$ formula I/A-3

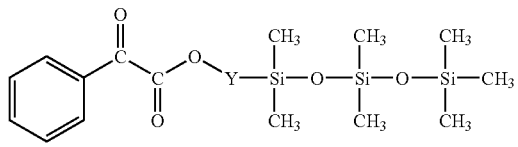

Compound B, compound of the formula I/A-3 where Y=—$(CH_2)$:$_3$—;
Compound C, compound of the formula I/A-3 where Y=—$(CH_2)_4$—;
Example 2, compound of the formula I/A-3 where Y=—$(CH_2)_6$—;
Example 7, compound of the formula I/A-3 where Y=—$(CH_2)_2$—O—$(CH_2)_3$—;
A-4 A is a radical of the formula III, in which n=1; m=0; p=1; x=2; $G_1$=$CH_3$; $G_2$=—Si—$(CH_3)_3$ formula I/A-4

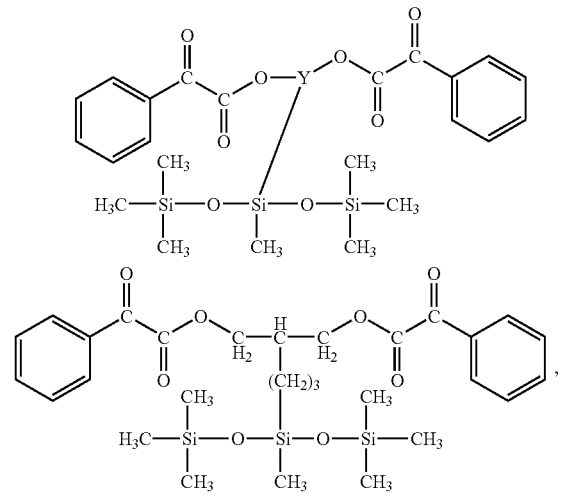

Example 11, compound of the formula I/A-4 where Y=—(CH)—((CH$_2$)$_3$—)$_2$;
Example 13, compound of the formula I/A-4 where Y=—$CH_2$—C($C_2H_5$)—($CH_2$—O—($CH_2$)$_3$—)$_2$
B. Compounds of the formula I in which R=phenyl; r=2; s=1; and
B-1. A is a radical of the formula III, in which n=1; m=0; p=0; x=1; $G_1$=—O—Si—$(CH_3)_3$; $G_2$=—Si—$(CH_3)_3$ formula I/B-1

Example 21, compound of the formula I/B-1 where Y=(—CH$_2$)(—CH$_2$)—C(H)(CH$_2$)$_3$—;
(formula Y-1, where a=1, b=1, c=3, R$_{24}$=H)
Example 14, compound of the formula I/B-1 where Y=(—CH$_2$)(—CH$_2$)C(CH$_2$—CH$_3$)(CH$_2$—(CH$_2$)$_3$—)
(formula Y-5, where a=1, b=1, c=1, d=3, R$_{24}$=C$_2$H$_5$)
Example 18, compound of the formula I/B-1 where Y=—C(H)(CH$_2$—)(CH$_2$—O—CH$_2$CH$_2$CH$_2$—)
(formula Y-5, where a=1, b=0, c=1, d=3, R$_{24}$=H,)
Compound D, compound of the formula I/B-1 where Y=(—CH$_2$)(—CH$_2$)C(H)(O—CH$_2$CH$_2$CH$_2$—),
(formula Y-2, where a=1, b=1, c=3, R$_{24}$=H)
Compound E, compound of the formula I/B-1 where Y=—C(H)(CH$_2$CH$_2$—)(CH$_2$CH$_2$CH$_2$—)
(formula Y-1, where a=2, b=0, c=3, R$_{24}$=H)
Compound F, compound of the formula I/B-1 where Y=—C(H)(CH$_2$—CH(CH$_3$)—)(CH$_2$CH$_2$CH$_2$—)
(formula Y-6, where a=0, b=1, c=3, R$_{24}$=H, R$_{25}$=CH$_3$)
B-2. A is a radical of the formula III, in which n=1; m=0; p=1; x=1; G$_1$ CH$_3$; G$_2$=—Si—(CH$_3$)$_3$ formula I/B-2

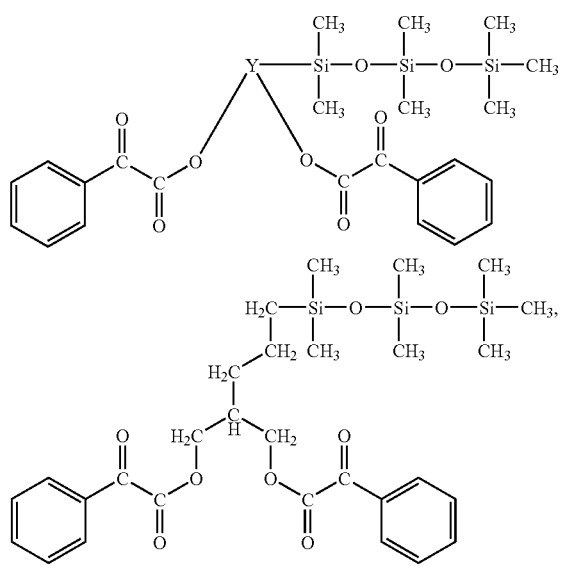

Compound G, compound of the formula I/B-2 where Y=(—CH$_2$)(—CH$_2$)C(H)(CH$_2$CH$_2$CH$_2$—)
(formula Y-1, where a=1, b=1, c=3, R$_{24}$=H)
Compound H, compound of the formula I/B-2 where Y=(—CH$_2$)(—CH$_2$)C(H)(O—CH$_2$CH$_2$CH$_2$—)
(formula Y-2, where a=1, b=1, c=3, R$_{24}$=H)
Compound I, compound of the formula I/B-2 where Y=—C(H)(CH$_2$CH$_2$—)(CH$_2$CH$_2$CH$_2$—)
(formula Y-1, where a=0, b=2, c=3, R$_{24}$=H)
Compound K, compound of the formula I/B-2 where Y=—C(H)(CH$_2$—CH(CH$_3$)—)(CH$_2$CH$_2$CH$_2$—)
(formula Y-6, where a=0, b=1, c=3, R$_{25}$=CH$_3$)
Example 15, compound of the formula I/B-2 where Y=(—CH$_2$)(—CH$_2$)C(CH$_2$—CH$_3$)(CH$_2$—O—(CH$_2$)$_3$—
(formula Y-5, where a=1, b=1, c=1, d=3, R$_{24}$=C$_2$H$_5$)
Example 19, compound of the formula I/B-2 where Y=—C(H)(CH$_2$—)(CH$_2$—O—CH$_2$CH$_2$CH$_2$—)
(formula Y-5, where a=0, b=1, c=1, d=3, R$_{24}$=H)

C. Compounds of the formula I in which R=phenyl; r=1; s=2;

C-1. A is a radical of the formula III, in which n=2; m=0; p=0; x=1; —O—Si—(CH$_3$)$_3$; G$_2$=—Si—(CH$_3$)$_3$ formula I/C-1

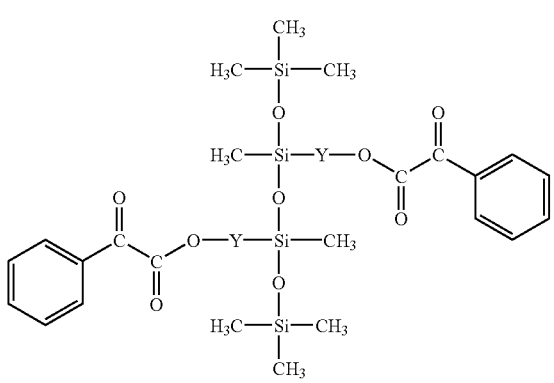

Example 3 compound of the formula I/C-1 where Y=—(CH$_2$)$_6$—;
Example 8 compound of the formula I/C-1 where Y=(CH$_2$)$_2$—O—(CH$_2$)$_3$—
Compound L compound of the formula I/C-1 where Y=—(CH$_2$)$_3$—;
Compound M compound of the formula I/C-1 where Y=—(CH$_2$)$_4$—;
C-2. A is a radical of the formula III, in which n=2; m=0;; x=1; G$_1$=—CH$_3$; G$_2$=—CH$_3$ with the proviso that the group G$_2$ is attached directly to the silicon atom without an oxygen bridge.

formula I/C-2

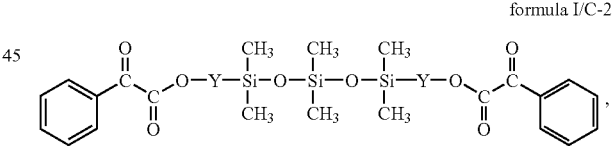

Example 4, compound of the formula I/C-2 where Y=—(CH$_2$)$_6$—; p=1
Example 9, compound of the formula I/C-2 where Y=(CH$_2$)$_2$—O—(CH$_2$)$_3$—; p=1
Example 24, compound of the formula I/C-2 where Y=—(CH$_2$)$_6$—, p=8
Compound N, compound of the formula I/C-2 where Y=—(CH$_2$)$_3$—; p=1
Compound O, compound of the formula I/C-2 where Y=—(CH$_2$)$_4$—; p=1
D. Compounds of the formula I in which R=phenyl; r=2; s=2; and
D-1. A is a radical of the formula III, in which n=2; m=0; p=0; x=1; G$_1$=—O—Si—(CH$_3$)$_3$; G$_2$=—Si—(CH$_3$)$_3$

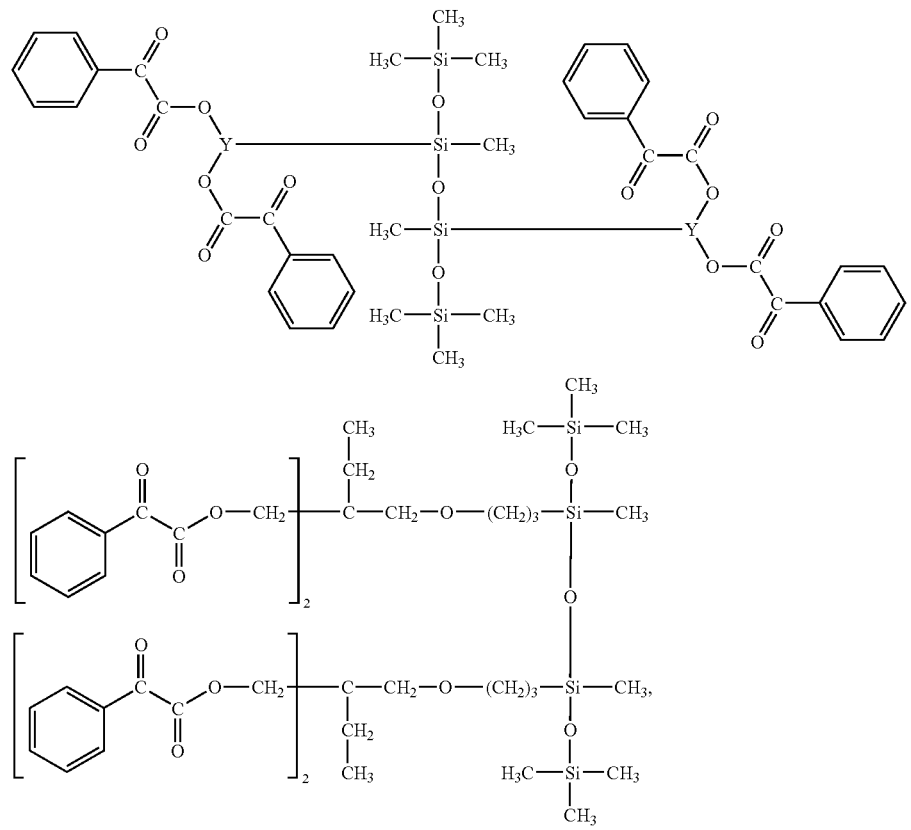

formula I/D-1

Example 16 compound of the formula I/D-1 where Y=—CH$_2$—C(—CH$_2$—)(—CH$_2$—CH$_3$)—CH$_2$—O—(CH$_2$)$_3$—, (formula Y-5, where a=1, b=1, c=1, d=3, R$_{24}$=C$_2$H$_5$)

Example 20 compound of the formula I/D-1 where Y=—CH$_2$—(CH—)—CH$_2$—O—(CH$_2$)$_3$—

(formula Y-5, where a=0, b=1, c=1, d=3, R$_{24}$=H)

Example 23 compound of the formula I/D-1 where Y=(—CH$_2$)(—CH)(CH$_2$—)((CH$_2$)$_3$—)
(formula Y-1, where a=1, b=1, c=3, R$_{24}$=H)

Compound P compound of the formula I/D-1 where Y=(—CH$_2$)C(H)(CH$_2$—)(O—CH$_2$CH$_2$CH$_2$—)
(formula Y-2, where a=1, b=1, c=3, R$_{24}$=H)

D-2. A is a radical of the formula III, in which n=2; m=0; p=1; x=1; G$_1$=CH$_3$; G$_2$=CH$_3$, with the proviso that the group G$_2$ is attached directly to the silicon atom without an oxygen bridge formula I/D-2

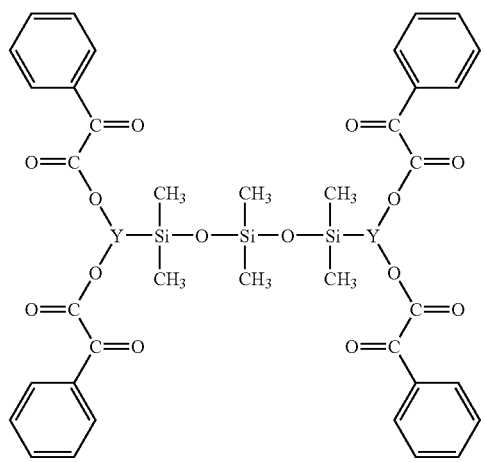

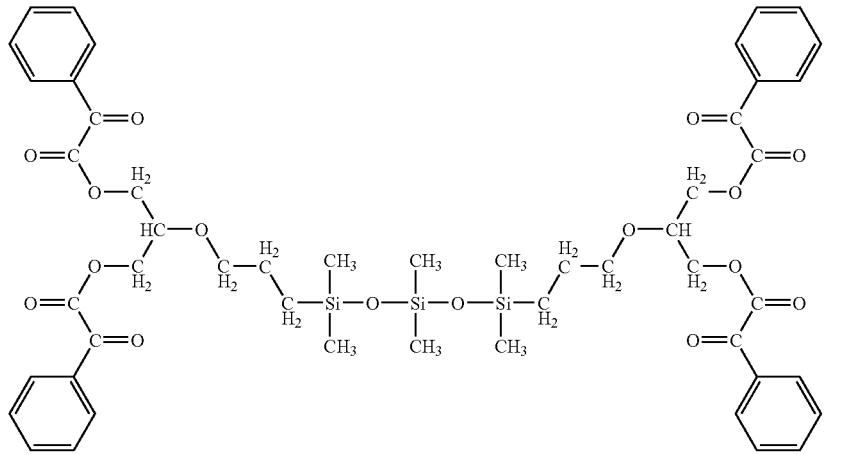

Compound R compound of the formula I/D-2 where
Y=—CH$_2$—C(H)(CH$_2$—)(O—CH$_2$CH$_2$CH$_2$—)
(formula Y-2, where a=1, b=1, c=3, R$_{24}$=H)

Example 22 compound of the formula I/D-1 where
Y=—CH$_2$—CH(—CH$_2$—)—(CH$_2$)$_3$—,
(formula Y-1, where a=1, b=1, c=3, R$_{24}$=H)

E. Compounds of the formula I in which R=phenyl; Y is a single bond; r=1; s=1; and A is a Radical Ao formula I/E

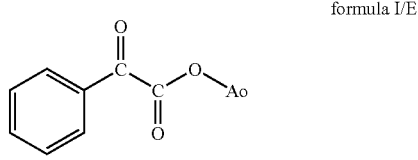

Example 26, compound of the formula I/E where Ao=C$_{18}$H$_{37}$
Example 27, compound of the formula I/E where Ao=C$_{28}$H$_{57}$
Example 30, compound of the formula I/E where Ao=—CH$_2$—CH$_2$—(CF$_2$)$_7$—CF$_3$ F. Compounds of the formula I, in which R=phenyl; Y is a single bond; r=1; s=2; and A is a radical Ao formula I/F

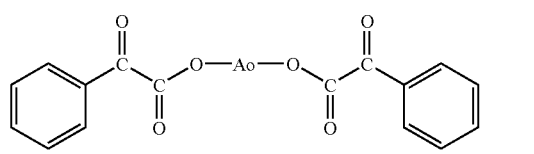

Example 28, compound of the formula i/E where Ao=C$_{16}$H$_{32}$
Example 29, compound of the formula I/E where Ao=C$_{12}$H$_{24}$
Compound U, compound of the formula I/E where Ao=C$_{10}$F$_{20}$
Compound V, compound of the formula I/E where. Ao=—CH$_2$—CH$_2$—C$_4$F$_8$
Compound W, compound of the formula I/E where. Ao=—CH$_2$—CH$_2$—C$_{18}$F$_{17}$ Preference is given to a process wherein
R is a radical of the formula II in which
R$_1$, R$_2$, R$_3$, R$_4$ and R$_5$ independently of one another are hydrogen; unsubstituted C$_1$-C$_{12}$alkyl; C$_2$-C$_{12}$alkyl which is interrupted by one or more non-successive oxygen atoms; or
are OR$_6$; SR$_7$; NR$_8$R$_9$; halogen; unsubstituted phenyl, where the substituents OR$_6$, SR$_7$, NR$_8$R$_9$ may form 5- or 6-membered rings via the radicals R$_6$, R$_7$, R$_8$ and/or R$_9$ with further substituents on the phenyl ring or one of the carbon atoms of the phenyl ring;
R$_6$ and R$_7$ independently of one another are hydrogen, unsubstituted C$_1$-C$_{12}$alkyl; OH-substituted C$_1$-C$_{12}$alkyl; unsubstituted phenyl, cyclopentyl or cyclohexyl;
R$_8$ and R$_9$ independently of one another are hydrogen, unsubstituted C$_1$-C$_{12}$alkyl; OH- or phenyl-substituted C$_1$-C$_{12}$alkyl; phenyl, —(CO)R$_{10}$; or
R$_8$ and R$_9$, together with the nitrogen atom to which they are attached, form a 5-, 6- or 7-membered ring which is uninterrupted or interrupted by —O— or —NR$_{12}$—;
R$_{10}$ is C$_1$-C$_8$alkyl or unsubstituted or C$_1$-C$_4$alkyl and/or C$_1$-C$_4$alkoxy-substituted phenyl;
R$_{12}$ is hydrogen, unsubstituted or OH- or C$_1$-C$_4$alkoxy-substituted C$_1$-C$_8$alkyl; or unsubstituted or OH-, C$_1$-C$_4$alkyl- or C$_1$-C$_4$alkoxy-substituted phenyl;
A, if s is 1,
either is a surface-active radical A$_0$,
A$_0$ being unsubstituted C$_6$-C$_{30}$alkyl or halogen-substituted C$_6$-C$_{30}$alkyl and being uninterrupted or interrupted by one or more —O—, —S— or —NR$_{12}$—;
or is a surface-active radical of the formula III in which G$_1$ and G$_2$ have the definition indicated above, and
R$_{13}$, R$_{14}$, R$_{15}$, R$_{17}$, R$_{18}$, R$_{19}$, R$_{20}$, R$_{21}$ and R$_{22}$ independently of one another are C$_1$-C$_{18}$alkyl, phenyl, C$_2$-C$_6$hydroxyalkyl, C$_2$-C$_6$aminoalkyl, cyclopentyl or cyclohexyl;
R$_{16}$ is unsubstituted C$_1$-C$_{18}$alkyl; C$_1$-C$_{18}$alkyl substituted by hydroxyl, C$_1$-C$_{12}$alkoxy, halogen, cyclohexyl, cyclopentyl and/or N(R$_8$)(R$_9$); unsubstituted phenyl; phenyl substituted by C$_1$-C$_{12}$alkyl, C$_1$-C$_{12}$alkoxy, halogen, hydroxyl and/or N(R$_8$)(R$_9$); or cyclohexyl, -pentyl A, if s is 2,
  is either a radical of the formula III or
  a radical $A_1$;
    $A_1$ being unsubstituted $C_6$-$C_{30}$alkylene or halogen-substituted $C_6$-$C_{30}$alkylene and being uninterrupted or interrupted by one or more —O—, —S— or —$NR_{12}$—;
r is as defined above,
s is a number from 1-10, especially 1 or 2, with the proviso that, if A=$A_0$ or $A_1$, s=1 or 2;
n is a number from 1 to 10 or, if the siloxane starting material is a mixture of oligomeric siloxanes, n may also be less than 1 but greater than 0;
m is a number from 0 to 10;
p is a number 0-100;
x is 1, 2 or 3;
Y is as defined above.

Particular preference is given to a process wherein
R is phenyl,
A if s is 1,
  either is a surface-active radical $A_0$,
    $A_0$ being unsubstituted or halogen-substituted $C_{12}$-$C_{30}$alkyl,
  or is a surface-active radical of the formula III in which $G_1$ and $G_2$ have the definition indicated above and $R_{13}$, $R_{14}$, $R_{15}$, $R_{16}$, $R_{17}$, $R_{18}$, $R_{19}$, $R_{20}$, $R_{21}$ and $R_{22}$ are methyl;
A, if s is 2,
  is a surface-active radical $A_1$;
    $A_1$ being unsubstituted or halogen-substituted $C_{12}$-$C_{30}$alkylene,
  or is a surface-active radical of the formula III in which $G_1$ and $G_2$ have the definition indicated above and $R_{13}$, $R_{14}$, $R_{15}$, $R_{16}$, $R_{17}$, $R_{18}$, $R_{19}$, $R_{20}$, $R_{21}$ and $R_{22}$ are methyl;
r is 1 or 2;
s is 1 or 2;
n is a number from 1 to 10, or, if the siloxane starting material is a mixture of oligomeric siloxanes, n may also be less than 1 but greater than 0;
m is a number from 0 to 10;
p is a number 0-100;
x is 1, 2 or 3;
Y, if r=1 and x=1,
  is a divalent group $C_1$-$C_{10}$alkylene, $C_2$-$C_{10}$alkenylene, $C_2$-$C_{10}$alkynylene, —$(CH_2)_a$—O—, —$[(CH_2)_a$—O—$(CH_2)_b]_c$—, —$[(CH_2)_a$—O$]_q$—$(CH_2)_b$—, —$(CH_2)_a$—O—$(CH_2)_b$—O—, —$(C_2$-$C_{10}$alkenylene)-O—$(CH_2)_a$—, —$(C_2$-$C_{10}$alkynylene)-O—$(CH_2)_a$—,
Y, if r=1 and x>1,
  is —$CR_{23}$—$[(CH_2)_b]_2$, —C—$[(CH_2)_b]_3$; $(CH_2)_a$—CH—$[(CH_2)_b]_2$; $(CH_2)_a$—C—$[(CH_2)_b]_3$; —$CR_{23}$—$[(CH_2)_a$—O—$(CH_2)_b]_2$; —C—$[(CH_2)_a$—O—$(CH_2)_b]_3$; $(CH_2)_a$—$CR_{23}$—$[(CH_2)_a$—O—$(CH_2)_b]_2$; $(CH_2)_a$—C—$[(CH_2)_a$—O—$(CH_2)_b]_3$ and
$R_{23}$, is hydrogen or $C_1$-$C_4$alkyl, Y, if r=2,
  is a trivalent group of the formulae:

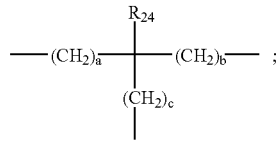

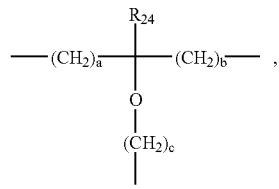

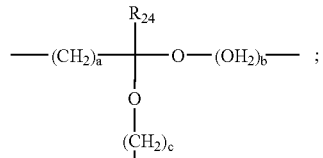

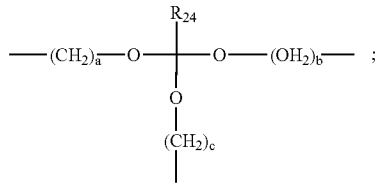

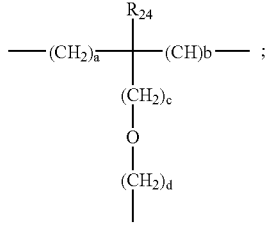

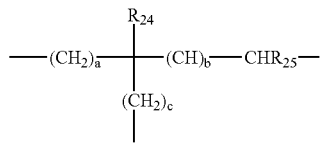

and
$R_{24}$ is hydrogen or $C_1$-$C_4$alkyl,
$R_{25}$ is $C_1$-$C_4$alkyl,
and at the site where a bond is made to the photoinitiator radical

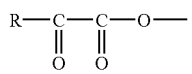

there must always be at least one methylene group; and
Y, if A has the definition $A_0$ or $A_1$, is a single bond;
a is a number from 1 to 10;
b, c and d independently of one another are a number from 0 to 10; with the proviso that they are at least 1 if the methylene group in question is between two oxygen atoms or one oxygen and one nitrogen atom, and q is a number from 1 to 10.

Very particular preference is given to a process in which a siloxane-containing surface-active photoinitiator of the formula I is used, i.e. a process wherein R is phenyl, A is a radical of the formula III in which $G_1$ and $G_2$ have the definition indicated above and $R_{13}$, $R_{14}$, $R_{15}$, $R_{16}$, $R_{17}$, $R_{18}$, $R_{19}$, $R_{20}$, $R_{21}$, and $R_{22}$ are methyl;

r is 1 or 2;

s is 1 or 2;

n is a number from 1 to 10, or, if the siloxane starting material is a mixture of oligomeric siloxanes, n may also be less than 1 but greater than 0;

m is a number from 0 to 10;

p is a number 0-100;

x is 1, 2 or 3;

Y, if r=1 and x=1, is a divalent group $C_1$-$C_{10}$alkylene, $C_2$-$C_{10}$alkenylene, $C_2$-$C_{10}$alkynylene, —$(CH_2)_a$—O—, —[$(CH_2)_a$—O—$(CH_2)_b$]$_c$—, —[$(CH_2)_a$—O]$_q$—$(CH_2)_b$—, —$(CH_2)_a$—O—$(CH_2)_b$—O—, —$(C_2$-$C_{10}$alkenylene)-O—$(CH_2)_a$—, —$(C_2$-$C_{10}$alkynylene)-O—$(CH_2)_a$—, Y, if r=1 and x>1, is —$CR_{23}$—[$(CH_2)_b$]$_2$, —C—[$(CH_2)_b$]$_3$; $(CH_2)_a$—CH—[$(CH_2)_b$]$_2$; $(CH_2)_a$—C—[$(CH_2)_b$]$_3$; —$CR_{23}$—[$(CH_2)_a$—O—$(CH_2)_b$]$_2$; —C—[$(CH_2)_a$—O—$(CH_2)_b$]$_3$; $(CH_2)_a$—$CR_{23}$—[$(CH_2)_a$—O—$(CH_2)_b$]$_2$; $(CH_2)_a$—C—[$(CH_2)_a$—O—$(CH_2)_b$]$_3$ and $R_{23}$ is hydrogen or $C_1$-$C_4$alkyl, Y, if r=2, is a trivalent group of the formulae:

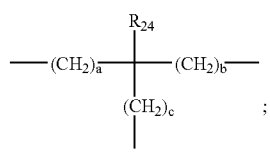
Y-1

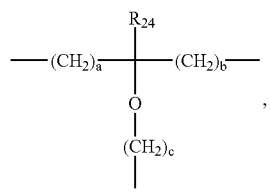
Y-2

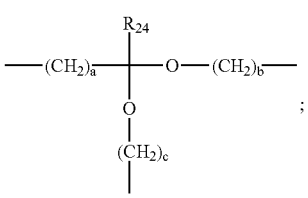
Y-3

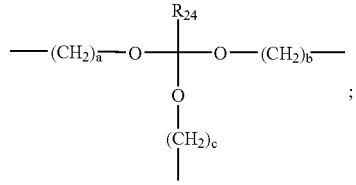
Y-4

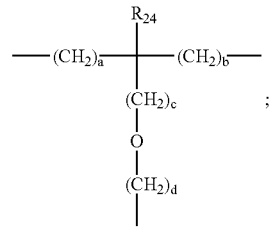
Y-5

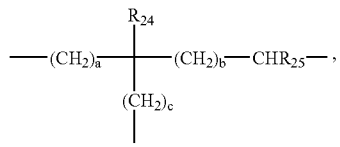
Y-6

$R_{24}$ is hydrogen or $C_1$-$C_4$alkyl, $R_{25}$ is $C_1$-$C_4$alkyl, and at the site where a bond is made to the photoinitiator radical

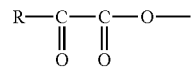

there must always be at least one methylene group; and a is a number from 1 to 10;

b, c and d independently of one another are a number from 0 to 10; with the proviso that they are at least 1 if the methylene group in question is between two oxygen atoms or one oxygen and one nitrogen atom, q is a number from 1 to 10.

The photoinitiator used may also be a mixture of siloxane-containing photoinitiator of the formula I and a photoinitiator of the formula I in which A is the radical $A_0$ or $A_1$.

In accordance with the invention, the photoinitiators are used to cure free-radically polymerizable systems, the objective being to obtain a hardened surface having outstanding properties. For this objective to be achieved it is critical that the photoinitiator accumulates at the surface of the formulation to be cured. As has already been described above, this is achieved by means of appropriate substituents on the photoinitiator. However, an improvement in the surface properties is not only achievable using such initiators just in purely photocurable systems, but is also obtained in mixed thermally/photocurable formulations. The present invention therefore provides both for the use of the photoinitiators of the formula I in purely photocurable formulations and for the use of the photoinitiators of the formula I in mixed photochemically and thermally curable formulations. Thermal curing may take place before, during or after exposure to light.

The invention accordingly also provides a process as described above in which the photocurable formulation comprises as a further component at least one thermally crosslinkable compound (C) and the formulation is cured by exposure to light whose wavelength extends from 200 nm into the IR region and by prior, simultaneous and/or subsequent exposure to heat.

In accordance with the invention, the compounds of the formula I may be used as surface-active photoinitiators for the photopolymerization of ethylenically unsaturated compounds or mixtures comprising such compounds. The compounds of the formula I undergo orientation toward the surface of the respective formulation. In accordance with the invention, the initiators of the formula (I) are not used in compositions which comprise siloxane-modified resin components, since in such compositions the accumulation at the surface is unable to occur; instead, the initiators are compatible with the formulation and are therefore readily miscible.

The invention also provides a method of causing a photoinitiator to accumulate at the surface of coatings comprising ethylenically unsaturated photopolymerizable compounds, which comprises adding a surface-active photoinitiator of the formula I to the photopolymerizable mixture comprising the ethylenically unsaturated photopolymerizable compounds.

The photoinitiators may also be used in combination with other photoinitiators (E) and/or further additives (D).

The invention accordingly also provides photopolymerizable compositions comprising
(A) at least one ethylenically unsaturated free-radically photopolymerizable compound; and
(B) at least one surface-active photoinitiator of the formula I, with the proviso that, if A in the compound of the formula I is not a radical $A_0$ or $A_1$, the composition contains no siloxane-modified resins besides the photoinitiator.

The invention further provides photopolymerizable compositions comprising
(A) at least one ethylenically unsaturated free-radically photopolymerizable compound;
(B) at least one surface-active photoinitiator of the formula I, and
(C) at least one thermally crosslinkable compound;

with the proviso that, if A in the compound of the formula I is not a radical $A_0$ or $A_1$, the composition contains no siloxane-modified resins besides the photoinitiator.

In accordance with the invention, the compositions may also comprise further, different photoinitiators (E) and/or further additives (D). The addition of thermal crosslinking catalysts is also possible. Suitable examples are set out later on below.

The unsaturated compounds (A) may contain one or more olefinic double bonds. They may be of low (monomeric) or relatively high (oligomeric) molecular mass. Examples of monomers containing a double bond are alkyl or hydroxyalkyl acrylates or methacrylates, such as methyl, ethyl, butyl, 2-ethylhexyl or 2-hydroxyethyl acrylate, isobornyl acrylate, methyl methacrylate or ethyl methacrylate. Other examples are acrylnitrile, acrylamide, methacrylamide, N-substituted (meth)acrylamides, vinyl esters such as vinyl acetate, vinyl ethers such as isobutyl vinyl ether, styrene, alkylstyrenes and halostyrenes, N-vinylpyrrolidone, vinyl chloride or vinylidene chloride.

Examples of monomers containing two or more double bonds are ethylene glycol, propylene glycol, neopentyl glycol, hexamethylene glycol and bisphenol A diacrylates, 4,4'-bis(2-acryl-oyloxyethoxy)diphenylpropane, trimethylolpropane triacrylate, pentaerythritol triacrylate or tetraacrylate, vinyl acrylate, divinylbenzene, divinyl succinate, diallyl phthalate, triallyl phosphate, triallyl isocyanurate or tris(2-acryloylethyl) isocyanurate.

Examples of relatively high molecular mass (oligomeric) polyunsaturated compounds are acrylated epoxy resin and acrylated or vinyl ether- or epoxy-functional polyesters, polyurethanes and polyethers. Further examples of unsaturated oligomers are unsaturated polyester resins, generally prepared from maleic acid, phthalic acid and one or more diols and having molecular weights of from about 500 to 3000. In addition to these it is also possible to use vinyl ether monomers and oligomers, and also maleate-terminated oligomers with polyesters, polyurethane, polyether, polyvinyl ether and epoxide main chains. Especially suitable are combinations of polymers and oligomers which carry vinyl ether groups, as described in WO 90/01512. Also suitable, however, are copolymers of monomers functionalized with maleic acid and vinyl ether.

Also suitable are compounds containing one or more free-radically polymerizable double bonds. In these compounds the free-radically polymerizable double bonds are preferably in the form of (meth)acryloyl groups. (Meth) acryloyl and, respectively, (meth)acrylic here and below means acryloyl and/or methacryloyl, and acrylic and/or methacrylic, respectively. Preferably, at least two polymerizable double bonds are present in the molecule in the form of (meth)acryloyl groups. The compounds in question may comprise, for example, (meth)acryloyl-functional oligomeric and/or polymeric compounds of poly(meth) acrylate. The number-average molecular mass of this compound may be for example from 300 to 10 000, preferably from 800 to 10 000. The compounds preferably containing free-radically polymerizable double bonds in the form of (meth)acryloyl groups may be obtained by customary methods, for example by reacting poly(meth)acrylates with (meth)acrylic acid. These and other preparation methods are described in the literature and are known to the person skilled in the art.

Unsaturated oligomers of this kind may also be referred to as prepolymers.

Functionalized acrylates are also suitable. Examples of suitable monomers which are normally used to form the backbone (the base polymer) of such functionalized acrylate and methacrylate polymers are acrylate, methyl acrylate, methyl methacrylate, ethyl acrylate, ethyl methacrylate, n-butyl acrylate, n-butyl methacrylate, isobutyl acrylate, isobutyl methacrylate, 2-ethylhexyl acrylate, 2-ethylhexyl methacrylate etc. Additionally, appropriate amounts of functional monomers are copolymerized during the polymerization in order to give the functional polymers. Acid-functionalized acrylate or methacrylate polymers are obtained using acid-functional monomers such as acrylic acid and methacrylic acid. Hydroxy-functional acrylate or methacrylate polymers are formed from hydroxy-functional monomers, such as 2-hydroxyethyl methacrylate, 2-hydroxypropyl methacrylate and 3,4-dihydroxybutyl methacrylate. Epoxy-functionalized acrylate or methacrylate polymers are obtained using epoxy-functional monomers such as glycidyl methacrylate, 2,3-epoxybutyl methacrylate, 3,4-epoxybutyl methacrylate, 2,3-epoxycyclohexyl methacrylate, 10,11-epoxyundecyl methacrylate etc. Similarly, for examle, isocyanate-functionalized polymers may be prepared from isocyanate-functionalized monomers, such as meta-isopropenyl-α,α-dimethylbenzyl isocyanate, for example.

Particularly suitable compounds are, for example, esters of ethylenically unsaturated monofunctional or polyfunctional carboxylic acids and polyols or polyepoxides, and polymers containing ethylenically unsaturated groups in the chain or in side groups, such as unsaturated polyesters, polyamides and polyurethanes and copolymers thereof, alkyd resins, polybutadiene and butadiene copolymers, polyisoprene and isoprene copolymers, polymers and copolymers containing (meth)acrylic groups in side chains, and also mixtures of one or more such polymers.

Examples of suitable monofunctional or polyfunctional unsaturated carboxylic acids are acrylic acid, methacrylic acid, crotonic acid, itaconic acid, cinnamic acid, maleic acid, fumaric acid, unsaturated fatty acids such as linolenic acid or oleic acid. Acrylic acid and methacrylic acid are preferred.

It is, however, also possible to use saturated dicarboxylic or polycarboxylic acids in a mixture with unsaturated carboxylic acids. Examples of suitable saturated dicarboxylic or polycarboxylic acids include tetrachlorophthalic acid, tetrabromophthalic acid, phthalic acid, trimellitic acid, heptanedicarboxylic acid, sebacic acid, dodecanedicarboxylic acid, hexahydrophthalic acid, etc.

Suitable polyols include aromatic and especially aliphatic and cycloaliphatic polyols. Examples of aromatic polyols are hydroquinone, 4,4'-dihydroxybiphenyl, 2,2-di(4-hydroxyphenyl)propane, and also novolaks and resols. Examples of polyepoxides are those based on the aforementioned polyols, especially the aromatic polyols, and epichlorhydrin. Further suitable polyols include polymers and copolymers containing hydroxyl groups in the polymer chain or in side groups, such as polyvinyl alcohol and copolymers thereof or polyhydroxyalkyl methacrylates or copolymers thereof, for example. Oligoesters containing hydroxyl end groups are further suitable polyols.

Examples of aliphatic and cycloaliphatic polyols are alkylenediols having preferably from 2 to 12 carbon atoms, such as ethylene glycol, 1,2- or 1,3-propanediol, 1,2-, 1,3- or 1,4-butanediol, pentanediol, hexanediol, octanediol, dodecanediol, diethylene glycol, triethylene glycol, polyethylene glycols having molecular weights of preferably from 200 to 1500, 1,3-cyclopentanediol, 1,2-, 1,3- or 1,4-cyclohexanediol, 1,4-dihydroxymethylcyclohexane, glycerol, tris(β-hydroxyethyl)amine, trimethylolethane, trimethylolpropane, pentaerythritol, dipentaerythritol and sorbitol.

The polyols may have been partly or fully esterified with one or more different unsaturated carboxylic acids, the free hydroxyl groups in partial esters possibly having been modified, e.g. etherified or esterified with other carboxylic acids.

Examples of esters are:
trimethylolpropane triacrylate, trimethylolethane triacrylate, trimethylolpropane trimethacrylate, trimethylolethane trimethacrylate, tetramethylene glycol dimethacrylate, triethylene glycol dimethacrylate, tetraethylene glycol diacrylate, pentaerythritol diacrylate, pentaerythritol triacrylate, pentaerythritol tetraacrylate, dipentaerythritol diacrylate, dipentaerythritol triacrylate, dipentaerythritol tetraacrylate, dipentaerythritol pentaacrylate, dipentaerythritol hexaacrylate, tripentaerythritol octaacrylate, pentaerythritol dimethacrylate, pentaerythritol trimethacrylate, dipentaerythritol dimethacrylate, dipentaerythritol tetramethacrylate, tripentaerythritol octamethacrylate, pentaerythritol diitaconate, dipentaerythritol trisitaconate, dipentaerythritol pentaitaconate, dipentaerythritol hexaitaconate, ethylene glycol diacrylate, 1,3-butanediol diacrylate, 1,3-butanediol dimethacrylate, 1,4-butanediol diitaconate, sorbitol triacrylate, sorbitol tetraacrylate, modified pentaerythritol triacrylate, sorbitol tetramethacrylate, sorbitol pentaacrylate, sorbitol hexaacrylate, oligoester acrylates and methacrylates, glycerol diacrylate and triacrylate, 1,4-cyclohexane diacrylate, bisacrylates and bismethacrylates of polyethylene glycol having a molecular weight from 200 to 1500, or mixtures thereof.

Suitable components (A) also include the amides of identical or different unsaturated carboxylic acids with aromatic, cycloaliphatic and aliphatic polyamines having preferably from 2 to 6, particularly from 2 to 4 amino groups. Examples of such polyamines are ethylenediamine, 1,2- or 1,3-propylenediamine, 1,2-, 1,3- or 1,4-butylenediamine, 1,5-pentylenediamine, 1,6-hexylenediamine, octylenediamine, dodecylenediamine, 1,4-diaminocyclohexane, isophoronediamine, phenylenediamine, bisphenylenediamine, di-β-aminoethyl ether, diethylenetriamine, triethylenetetramine, di(β-aminoethoxy)- or di(β-aminopropoxy)ethane. Further suitable polyamines are polymers and copolymers containing possibly additional amino groups in the side chain, and oligoamides having amino end groups. Examples of such unsaturated amides are: methylenebisacrylamide, 1,6-hexamethylenebisacrylamide, diethylenetriaminetrismethacrylamide, bis(methacrylamidopropoxy)ethane, β-methacrylamidoethyl methacrylate, and N-[(β-hydroxyethoxy)ethyl]-acrylamide.

Suitable unsaturated polyesters and polyamides are derived, for example, from maleic acid and diols or diamines. The maleic acid may have been replaced in part by other dicarboxylic acids. They may be used together with ethylenically unsaturated comonomers, e.g. styrene. The polyesters and polyamides may also be derived from dicarboxylic acids and ethylenically unsaturated diols or diamines, especially from relatively long chain ones having, for example, from 6 to 20 carbon atoms. Examples of polyurethanes are those synthesized from saturated or unsaturated diisocyanates and unsaturated or saturated diols, respectively.

Polybutadiene and polyisoprene and copolymers thereof are known. Examples of suitable comonomers are olefins such as ethylene, propene, butene, hexene, (meth)acrylates, acrylonitrile, styrene or vinyl chloride. Polymers contaig (meth)acrylate groups in the side chain are likewise known. They may comprise, for example, reaction products of novolak-based epoxy resins with (meth)acrylic acid, homopolymers or copolymers of vinyl alcohol or the hydroxyalkyl derivatives thereof that have been esterified with (meth)acrylic acid, or homopolymers and copolymers of (meth)acrylates esterified with hydroxyalkyl (meth)acrylates.

The photopolymerizable compounds (A) may be used alone or in any desired mixtures. Preference is given to using mixtures of polyol (meth)acrylates.

It is also possible to add binders to the compositions of the invention, which is especially appropriate when the photopolymerizable compounds are liquid or viscous substances. The amount of the binder can be for example 5-95, preferably 10-90 and especially 40-90% by weight, based on the overall solids. The choice of binder is made depending on the field of use and the properties required for that field, such as developability in aqueous and organic solvent systems, adhesion to substrates, and oxygen sensitivity, for example.

Examples of suitable binders are polymers having a molecular weight of approximately 5 000-2 000 000, preferably 10 000-1 000 000. Examples are: homopolymeric and copolymeric acrylates and methacrylates, e.g. copolymers of methyl methacrylate/ethyl acrylatelmethacrylic acid, poly (alkyl methacrylates), poly(alkyl acrylates); cellulose esters and cellulose ethers such as cellulose acetate, cellulose acetate butyrate, methylcellulose, ethylcellulose; polyvinylbutyral, polyvinylformal, cyclized rubber, polyethers such as polyethylene oxide, polypropylene oxide, polytetrahydrofuran; polystyrene, polycarbonate, polyurethane, chlorinated polyolefins, polyvinyl chloride, copolymers of vinyl chloride/vinylidene chloride, copolymers of vinylidene chloride with acrylonitrile, methyl methacrylate and vinyl acetate, polyvinyl acetate, copoly(ethylene/vinyl acetate), polymers such as polycaprolactam and poly(hexamethyleneadipamide), polyesters such as poly(ethylene glycol terephtalate) and poly(hexamethylene glycol succinate).

As component (A), i.e. UV-curable component, it is also possible to use the resins listed later on below under (C1). Examples of those that are of particular interest are unsaturated acrylates containing reactive functional groups. The reactive functional group may be selected, for example, from a hydroxyl, thiol, isocyanate, epoxide, anhydride, carboxyl, amino or a blocked amino group. Examples of OH-containing unsaturated acrylates are hydroxyethyl and hydroxybutyl acrylates or else glycidyl acrylates.

The unsaturated compounds may also be used in a mixture with non-photopolymerizable film-forming components. These may be, for example, physically drying polymers or their solutions in organic solvents, such as nitrocellulose or cellulose acetobutyrate, for example. They may also, however, be chemically and/or thermally curable resins, such as polyisocyanates, polyepoxides or melamine resins, for example. By melamine resins are meant not only condensates of melamine (1,3,5-triazine-2,4,6-triamine) but also those of melamine derivatives. In general, the components comprise a film-forming binder based on a thermoplastic or therrmosettable resin, predominantly on a thermosettable resin. Examples thereof are alkyd, acrylic, polyester, phenolic, melamine, epoxy and polyurethane resins and mixtures thereof. The additional use of thermally curable resins is of importance for use in what are known as hybrid systems, which may be both photopolymerized and also thermally crosslinked.

Component (A) may comprise, for example, a coating composition comprising (A1) compounds containing one or more free-radically polymerizable double bonds and further containing at least one other functional group which is reactive in the sense of an addition reaction and/or condensation reaction (examples have been given above), (A2) compounds containing one or more free-radically polymerizable double bonds and further containing at least one other functional group which is reactive in a sense of an addition reaction and/or condensation reaction, the additional reactive functional group being complementary to or reactive toward the additional reactive functional groups of component (A1), (A3) if desired, at least one monomeric, oligomeric and/or polymeric compound containing at least one functional group which is reactive in the sense of an addition reaction and/or condensation reaction toward the functional groups from component (A1) or component (A2) that are present in addition to the free-radically polymerizable double bonds.

Component (A2) carries in each case the groups which are reactive toward or complementary to component (A1). In this context it is possible in each case for different kinds of functional groups to be present in one component. In component (A3) there is a further component available containing functional groups which are reactive in the sense of addition reactions and/or condensation reactions and which are able to react with the functional groups of (A1) or (A2) that are present in addition to the free-radically polymerizable double bonds. Component (A3) contains no free-radically polymerizable double bonds. Examples of such combinations of (A1), (A2), (A3) can be found in WO 99/55785. Examples of suitable reactive functional groups are selected, for example, from hydroxyl, isocyanate, epoxide, anhydride, carboxyl or blocked amino groups. Examples have been described above.

Constituents of component (C) are, for example, thermally curable coating system constituents that are customary in the art. Accordingly, component (C) may comprise two or more constituents.

Examples of component (C) are oligomers and/or polymers derived from $\alpha,\beta$-unsaturated acids and derivatives thereof; examples are polyacrylates and polymethacrylates, and polyacrylonitriles, polyacrylamides and polymethyl methacrylates that have been impact-modified using butyl acrylate. Further examples of component (C) are urethanes, polyurethanes derived from polyethers, polyesters and polyacrylates containing free hydroxyl groups or thiol groups, on the one hand, and aliphatic or aromatic polyisocyanates, on the other, and also precursors thereof. Accordingly, component (C) also comprises, for example, crosslinkable acrylic resins derived from substituted acrylates, such as epoxy acrylates, urethane acrylates or polyester acrylates. It is also possible for alkyd resins, polyester resins and acrylic resins and their modifications, which are crosslinked with melamine resins, urea resins, isocyanates, isocyanurates, polyisocyanates, polyisocyanurates and epoxy resins, to be constituents of component (C).

Component (C) generally comprises for example, a film-forming binder based on a thermoplastic or thermosettable resin, predominantly on a thermosettable resin. Examples thereof are alkyd, acrylic, polyester, phenolic, melamine, epoxy and polyurethane resins and mixtures thereof. Examples of these are described, for example, in Ullmann's Encyclopedia of Industrial Chemistry, 5th Ed., Vol. A18, pp. 368-426, VCH, Weinheim 1991.

Component (C) may be a cold-curable or heat-curable binder, and the addition of a curing catalyst may be advantageous. Suitable catalysts that accelerate the curing of the binder are described, for example, in Ullmann's Encyclopedia of Industrial Chemistry, Vol. A18, p. 469, VCH Verlagsgesellschaft, Weinheim 1991.

Examples of specific binders suitable as component (C) are

1. Paints based on cold- or heat-crosslinkable alkyd, acrylate, polyester, epoxy or melamine resins or mixtures of such resins, with or without addition of a curing catalyst;
2. Two-component polyurethane paints based on hydroxyl-containing acrylate, polyester or polyether resins and on aliphatic or aromatic isocyanates, isocyanurates or polyisocyanates;
3. One-component polyurethane paints based on blocked isocyanates, isocyanurates or polyisocyanates that are deblocked in the course of stoving; melamine resins can also be added, if appropriate;
4. One-component polyurethane paints based on aliphatic or aromatic urethanes or polyurethanes and on hydroxyl-containing acrylate, polyester or polyether resins;
5. One-component polyurethane paints based on aliphatic or aromatic urethane acrylates or polyurethane acrylates having free amine groups in the urethane structure and on melamine resins or polyether resins, with or without addition of a curing catalyst;
6. Two-component paints based on (poly)ketimines and on aliphatic or aromatic isocyanates, isocyanurates or polyisocyanates;
7. Two-component paints based on (poly)ketimines and on an unsaturated acrylate resin or a polyacetoacetate9 resin or a methacrylamidoglycolate methyl ester;
8. Two-component paints based on carboxyl- or amino-containing polyacrylates and polyepoxides;

9. Two-component paints based on acrylate resins containing anhydride groups and on a polyhydroxy or polyamino component;
10. Two-component paints based on acrylate-containing anhydrides and polyepoxides;
11. Two-component paints based on (poly)oxazolines and on acrylate resins containing anhydride groups, or unsaturated acrylate resins or aliphatic or aromatic isocyanates, isocyanurates or polyisocyanates;
12. Two-component paints based on unsaturated polyacrylates and polymalonates;
13. Thermoplastic polyacrylate paints based on thermoplastic acrylate resins or externally crosslinking acrylate resins in combination with etherified melamine resins;
14. Paint systems based on urethane (meth)acrylate containing (meth)acryloyl groups and free isocyanate groups and on one or more isocyanate-reactive compounds, such as unesterified or esterified polyols. Such systems are published, for example, in EP 928800.

Blocked isocyanates as may be employed, inter alia, in component (C) are described, for example, in Organischer Metallschutz: Entwicklung und Anwendung von Beschichtungsstoffen [Organic Protection of Metals: Development and Application of Coating Materials], page 159-160, Vincentz Verlag, Hannover (1993). These are compounds in which the highly reactive NCO group is "blocked" by reaction with specific radicals, such as primary alcohols, phenol, acetoacetates, ε-caprolactam, phthalimide, imidazole, oxime or amine. The blocked isocyanate is stable in liquid systems and also in the presence of hydroxyl groups. On heating, the blocking agents are eliminated and the NCO group is exposed.

Both 1-component(1K) and 2-component (2K) systems may be used as component (C). Examples of such systems are described in Ullmann's Encyclopedia of Industrial Chemistry, Vol. A18, Paints and Coatings, page 404-407, VCH Verlagsgesellschaft mbH, Weinheim (1991).

The composition may be optimized by specially adapting the formulation, for example by varying the binder/crosslinker ratio. Such measures are well known to the person skilled in the art of coatings technology.

In the curing process of the invention the component (C) is preferably a mixture based on acrylate/melamine (and melamine derivatives), 2-component polyurethane, 1-component polyurethane, 2-component epoxy/carboxy or 1-component epoxy/carboxy. Mixtures of these systems are also possible, an example being the addition of melamine (or derivatives thereof) to 1-component polyurethanes.

Component (C) is preferably a binder based on a polyacrylate with melamine or on a melamine derivative. Preference is also given to a system based on a polyacrylate polyol and/or polyester polyol with an unblocked polyisocyanate or polyisocyanurate.

Component (C) may further comprise monomeric and/or oligomeric compounds containing ethylenically unsaturated bonds (prepolymers) which additionally contain at least one or more OH, NH$_2$, COOH, epoxy or NCO groups (═C1) capable of reaction with the binder and/or crosslinker substituent of component (C). Following application and thermal curing, the ethylenically unsaturated bonds are converted by UV radiation into a crosslinked, high molecular mass form. Examples of such components (C) are described, for example, in the abovementioned publication Ullmann's Encyclopedia of Industrial Chemistry, 5th Ed., Vol. A18, pages 451-453, or by S. Urano, K. Aoki, N. Tsuboniva and R. Mizuguchi in Progress in Organic Coatings, 20 (1992), 471-486, or by H. Terashima and O. Isozaki in JOCCA 1992 (6), 222.

(C1) may be, for example, an OH-containing unsaturated acrylate, e.g. hydroxyethyl or hydroxybutyl acrylate or else glycidyl acrylates. The component (C1) may be of any desired construction (e.g. polyester, polyacrylate, polyether, etc., units) provided there are an ethylenically unsaturated double bond and also free OH, COOH, NH$_2$, epoxy or NCO groups.

(C1) may also be obtained, for example, by reacting an epoxy-functional oligomer with acrylic acid or methacrylic acid. A typical example of an OH-functional oligomer containing vinylic double bonds is

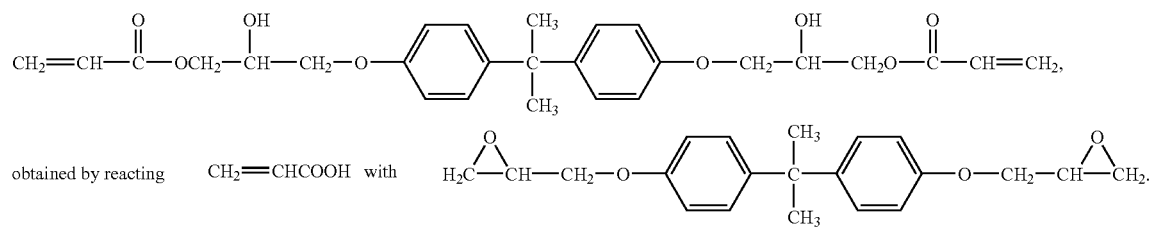

One possibility for preparing component (C1) is also, for example, the reaction of an oligomer that contains only one epoxy group and at another site in the molecule possesses a free OH group.

The ratio of components (A) to (C) in the UV-crosslinking and thermally crosslinking formulations is not critical. "Dual-cure" systems are well known to the person skilled in the art, who is therefore well aware of the optimum proportions of the UV-crosslinkable and thermally crosslinkable components for the particular desired application. For example, the compositions may comprise components (A) and (C) in a ratio of from 5:95 to 95:5, from 20:80 to 80:20 or from 30:70 to 70:30, e.g. from 40:60 to 60:40.

Examples of "dual-cure" systems, i.e. systems containing both UV-curable and thermally curable components, may be found, inter alia, in U.S. Pat. No. 5,922,473, columns 6 to 10.

To the compositions that are used in the process of the invention it is also possible to add solvents or water. Where the compositions are used without solvents, they comprise, for example, powder coating formulations. Suitable solvents are solvents which are known to the person skilled in the art and are customary particularly in coatings technology. Examples are various organic solvents, such as ketones, e.g. methyl ethyl ketone, cyclohexanone; aromatic hydrocarbons, e.g. toluene, xylene or tetramethylbenzene; glycol ethers, such as diethylene glycol monoethyl ether, dipropylene glycol diethyl ether; esters, such as ethyl acetate; aliphatic hydrocarbons, such as hexane, octane, decane; or petroleum solvents, such as petroleum ether.

The invention also provides compositions comprising as component (A) at least one ethylenically unsaturated photopolymerizable compound in emulsion or solution in water. Such radiation-curable aqueous prepolymer dispersions are available commercially in numerous variations. They are understood to comprise a dispersion of water and at least one prepolymer dispersed therein. The concentration of the water in these systems is, for example, from 5 to 80, in particular from 30 to 60% by weight. The radiation-curable pre-polymer or prepolymer mixture is present, for example, in concentrations of from 95 to 20, in particular from 70 to 40% by weight. In these compositions the sum of the percentages stated for water and prepolymers is in each case 100; the auxiliaries and additives are extra in different amounts depending on the intended use.

The radiation-curable film-forming prepolymers which are in dispersion and often also in solution in water comprise monofunctional or polyfunctional ethylenically unsaturated prepolymers which are known per se for aqueous prepolymer dispersions, may be initiated by means of free radicals, and have a polymerizable double bond content of, for example, from 0.01 to 1.0 mol per 100 g of prepolymer and also have an average molecular weight of, for example, at least 400, in particular from 500 to 10 000. Depending on the intended application, however, prepolymers with higher molecular weights may also be suitable. Use is made, for example, of polyesters containing polymerizable C—C double bonds and having an acid number of not more than 10, polyethers containing polymerizable C—C double bonds, hydroxyl-containing reaction products of a polyepoxide containing at least two epoxide groups per molecule with at least one α,β-ethylenically unsaturated carboxylic acid, polyurethane (meth)acrylates, and also acrylic copolymers containing α,β-ethylenically unsaturated acrylic radicals, as described, for example, in EP 012339. Mixtures of these prepolymers may likewise be used. Examples of further suitable prepolymers include the polymerizable prepolymers described in EP 033896, which are thioether adducts of polymerizable prepolymers having an average molecular weight of at least 600, a carboxyl group content of from 0.2 to 15% and a polymerizable C—C double bond content of from 0.01 to 0.8 mol per 100 g of prepolymer. Other suitable aqueous dispersions based on specific alkyl (meth)acrylate polymers are described in EP 041125; suitable water-dispersible, radiation-curable prepolymers comprising urethane acrylates are given, for example, in DE 2936039. As further additions, these radiation-curable aqueous prepolymer dispersions may comprise dispersing aids, emulsifiers, antioxidants, light stabilizers, dyes, pigments, fillers, e.g. talc, gypsum, silica, rutile, carbon black, zinc oxide, iron oxides, reaction accelerants, levelling agents, lubricants, wetting agents, thickeners, matting agents, defoamers, and other auxiliaries customary in coatings technology. Suitable dispersing aids include water-soluble organic compounds of high molecular mass containing polar groups, such as polyvinyl alcohols, polyvinylpyrrolidone or cellulose ethers. Emulsifiers which can be used include nonionic, and possibly also ionic, emulsifiers.

The compounds of the invention and mixtures thereof may also be used as free-radical photoinitiators or photo-initiating systems for radiation-curable powder coating materials. The powder coating materials may be based on solid resins and monomers containing reactive double bonds, such as maleates, vinyl ethers, acrylates, acrylamides and mixtures thereof. A free-radically UV-curable powder coating material may be formulated by mixing unsaturated polyester resins with solid acrylamides (e.g. methylacrylamidoglycolate methyl ester) and a free-radical photoinitiator of the invention, as described for example in the paper "Radiation Curing of Powder Coating", Conference Proceedings, Radtech Europe 1993 by M. Wittig and Th. Gohmann. Free-radically UV-curable powder coating materials may also be formulated by mixing unsaturated polyester resins with solid acrylates, methacrylates or vinyl ethers and a photoinitiator (or photoinitiator mixture) of the invention. The powder coating materials may also include binders, as described for example in DE 4228514 and EP 636669. The powder coating formulations described in EP 636669 contain, for example, a) an unsaturated resin from the group of the (semi)crystalline or amorphous unsaturated polyesters, unsaturated polyacrylates or mixtures thereof with unsaturated polyesters, particular preference being given to those derived from maleic acid or fumaric acid; b) an oligomeric or polymeric crosslinking agent containing vinyl ether-functional, vinyl ester-functional or (meth)acrylate-functional groups, particular preference being given to vinyl ether oligomers, such as divinyl ether-functionalized urethanes; c) the photoinitiator. The UV-curable powder coating materials may also comprise white or coloured pigments. For example, preferably rutile titanium dioxide may be used in concentrations of up to 50% by weight in order to give a cured powder coating possessing good hiding power. The technique normally involves applying the powder to the substrate, such as metal or wood, by electrostatic or tribostatic spraying, melting the powder by heating and, after a smooth film has formed, radiation-curing the coating with ultraviolet and/or visible light, using medium-pressure mercury lamps, metal halide lamps or xenon lamps, for example. A particular advantage of the radiation-curable powder coating materials over their thermally curable counterparts is that the flow time after melting of the powder particles may be selectively extended in order to ensure the formation of a smooth, highly glossy coating. Unlike thermally curable systems, radiation-curable powder coating materials may be formulated without the unwanted effect of a shortened lifetime in such a way that they melt at relatively low temperatures. For this reason they are also suitable as coatings for heat-sensitive substrates, such as wood or plastics.

Where the powder coating materials are not to be applied to heat-sensitive substrates, as in the case of metals (vehicle coatings), however, it is also possible to provide dual-cure powder coating formulations with the photoinitiators of the invention. The person skilled in the art knows such formulations; they are cured both thermally and by means of UV. Formulations of this kind are given, for example, in U.S. Pat. No. 5,922,473.

Besides the photoinitiators of the invention, the powder coating formulations may also comprise UV absorbers. Appropriate examples are listed later on below.

Besides the photoinitiator, the photopolymerizable mixtures may comprise various additives (D). Examples of these are thermal inhibitors, which are intended to prevent premature polymerization, such as hydroquinone, hydroquinone derivatives, p-methoxyphenol, β-naphthol or sterically hindered phenols such as 2,6-di(tert-butyl)-p-cresol. To increase the dark storage stability it is possible to use copper compounds, such as copper naphthenate, copper stearate or copper octoate, phosphorus compounds, such as triphenylphosphine, tributylphosphine, triethyl phosphite, triphenyl phosphite or tribenzyl phosphite, quaternary ammonium compounds, such as tetramethylammonium chloride or trimethylbenzyl-ammonium chloride, or hydroxylamine derivatives, such as N-diethylhydroxylamine, for example. For the purpose of excluding atmospheric oxygen in the course of the polymerization it is possible to add paraffin or similar wax-like substances, which at the beginning of polymerization migrate to the surface, on account of their poor solubility in the polymer, where they form a transparent surface layer which prevents the ingress of air. Similarly, it is possible to apply an oxygen-impermeable layer. Light stabilizers which can be added include UV absorbers, such as those of the hydroxyphenylbenzotriazole, hydroxyphenylbenzophenone, oxalmide or hydroxyphenyl-s-triazine type. These compounds may be used individually or in mixtures, with or without the use of sterically hindered amines (HALS).

Examples of such UV absorbers and light stabilizers are
1. 2-(2'-Hydroxyphenyl)benzotriazoles, for example 2-(2'-hydroxy-5'-methylphenyl)-benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chloro-benzotriazole, 2-(3'-tert-butyl-2'-hydroxy-5'-methylphenyl)-5-chloro-benzotriazole, 2-(3'-sec-butyl-5'-tert-butyl-2'-hydroxyphenyl)-benzotriazole, 2-(2'-hydroxy-4'-octyloxyphenyl)benzotriazole, 2-(3',5'-di-tert-amyl-2'-hydroxyphenyl)benzotriazole, 2-(3',5'-bis-($\alpha,\alpha$-dimethylbenzyl)-2'-hydroxyphenyl)-benzotriazole, 2-(3'-tert-butyl-2'-hydroxy-5'-(2-octyloxycarbonylethyl)phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl)phenyl)-5-chloro-benzotriazole, 2-(3'-tert-butyl-2'-hydroxy-5'-(2-methoxycarbonylethyl)phenyl)-benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl]-2'-hydroxyphenyl)benzotriazole, 2-(3'-dodecyl-2'-hydroxy-5'-methylphenyl)benzotriazole, 2-(3'-tert-butyl-2'-hydroxy-5'-(2-isooctyloxycarbonylethyl)phenylbenzotriazole, 2,2'-methylene-bis[4-(1,1,3,3-tetramethylbutyl)-6-benzotriazol-2-ylphenol]; the transesterification product of 2-[3'-tert-butyl-5'-(2-methoxycarbonylethyl)-2'-hydroxyphenyl]-2H-benzotriazole with polyethylene glycol 300; [R—$CH_2CH_2$—COO—$CH_2CH_2$]$_2$— where R=3'-tert-butyl-4'-hydroxy-5'-2H-benzotriazol-2-ylphenyl, 2-[2'-hydroxy-3'-($\alpha,\alpha$-dimethylbenzyl)-5'-(1,1,3,3-tetramethylbutyl)-phenyl]benzotriazole; 2-[2'-hydroxy-3'-(1,1,3,3-tetramethylbutyl)-5'-($\alpha,\alpha$-dimethylbenzyl)-phenyl]benzotriazole.
2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.
3. Esters of substituted and unsubstituted benzoic acids, for example 4-tert-butyl-phenyl salicylate, phenyl salicylate, octylphenyl salicylate, dibenzoyl resorcinol, bis(4-tert-butyl-benzoyl) resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.
4. Acrylates, for example ethyl $\alpha$-cyano-$\beta,\beta$-diphenylacrylate, isooctyl $\alpha$-cyano-$\beta,\beta$-diphenylacrylate, methyl $\alpha$-carbomethoxycinnamate, methyl $\alpha$-cyano-$\beta$-methyl-p-methoxycinnamate, butyl $\alpha$-cyano-$\beta$-methyl-p-methoxycinnamate, methyl $\alpha$-carbomethoxy-p-methoxycinnamate and N-($\beta$-carbomethoxy-$\beta$-cyanovinyl)-2-methylindoline.
5. Sterically hindered amines, for example bis(2,2,6,6-tetramethyl-4-piperidyl) sebacate, bis(2,2,6,6-tetramethyl-4-piperidyl) succinate, bis(1,2,2,6,6-pentamethyl-4-piperidyl) sebacate, bis(1-octyloxy-2,2,6,6-tetramethyl-4-piperidyl) sebacate, bis(1,2,2,6,6-pentamethyl-4-piperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, linear or cyclic condensates of N,N'-bis(2,2,6,6-tetramethyl-4-piperidyl)hexamethylenediamine and 4-tert-octylamino-2,6-dichloro-1,3,5-triazine, tris(2,2,6,6-tetramethyl-4-piperidyl) nitrilotriacetate, tetrakis(2,2,6,6-tetramethyl-4-piperidyl) 1,2,3,4-butane-tetracarboxylate, 1,1'-(1,2-ethanediyl)-bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl) 2-n-butyl-2-(2-hydroxy-3,5-di-tert-butylbenzyl)-malonate, 3-n-octyl-7,7,9,9-tetramethyl-1,3,8-triazaspiro[4.5]decane-2,4-dione, bis(1-octyloxy-2,2,6,6-tetramethylpiperidyl) sebacate, bis(1-octyloxy-2,2,6,6-tetramethylpiperidyl) succinate, linear or cyclic condensates of N,N'-bis-(2,2,6,6-tetramethyl-4-piperidyl)hexamethylenediamine and 4-morpholino-2,6-dichloro-1,3,5-triazine, the condensate of 2-chloro-4,6-bis(4-n-butylamino-2,2,6,6-tetramethylpiperidyl)-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis-(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidine-2,5-dione, 3-dodecyl-1-(1,2,2,6,6-pentamethyl-4-piperidyl)pyrrolidine-2,5-dione, a mixture of 4-hexadecyloxy- and 4-stearyloxy-2,2,6,6-tetramethylpiperidine, a condensation product of N,N'-bis(2,2,6,6-tetramethyl-4-piperidyl)hexamethylenediamine and 4-cyclohexylamino-2,6-dichloro-1,3,5-triazine, a condensation product of 1,2-bis(3-aminopropylamino)ethane and 2,4,6-trichloro-1,3,5-triazine as well as 4-butylamino-2,2,6,6-tetramethylpiperidine (CAS Reg. No. [136504-96-6]); N-(2,2,6,6-tetramethyl-4-piperidyl)-n-dodecylsuccinimide, N-(1,2,2,6,6-pentamethyl-4-piperidyl)-n-dodecylsuccinimide, 2-undecyl-7,7,9,9-tetramethyl-1-oxa-3,8-diaza-4-oxo-spiro[4.5]decane, a reaction product of 7,7,9,9-tetramethyl-2-cycloundecyl-1-oxa-3,8-diaza-4-oxospiro[4.5]decane und epichlorohydrin, 1,1-bis-(1,2,2,6,6-pentamethyl-4-piperidyloxycarbonyl)-2-(4-methoxyphenyl)ethene, N,N'-bis-formyl-N,N'-bis(2,2,6,6-tetramethyl-4-piperidyl)hexamethylenediamine, diester of 4-methoxy-methylene-malonic acid with 1,2,2,6,6-pentamethyl-4-hydroxypiperidine, poly[methylpropyl-3-oxy-4-(2,2,6,6-tetramethyl-4-piperidyl)]siloxane, reaction product of maleic acid anhydride-$\alpha$-olefin-copolymer with 2,2,6,6-tetramethyl-4-aminopiperidine or 1,2,2,6,6-pentamethyl-4-aminopiperidine.
6. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylamino propyl)oxamide, 2-ethoxy-5-tert-butyl-2'-ethoxanilide and its mixture with 2-ethoxy-2'-ethyl-5,4'-di-tert-butoxanilide, mixtures of o- and p-methoxy-disubstituted oxanilides and mixtures of o- and p-ethoxy-disubstituted oxanilides.
7. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxy-propoxy)phenyl]-4,6-bis(2,4-dimethyl)-1,3,5-triazine, 2-[2-hydroxy-4-(2-hydroxy-3-octyloxy-propyloxy)phenyl]-4,6-bis(2,4-dimethyl)-1,3,5-triazine, 2-[4-(dodecyloxy/tridecyloxy-2-hydroxypropoxy)-2-hydroxy-phenyl]-4,6-bis(2,4-dimethylphenyl)-1,3,5-triazine, 2-[2-hydroxy-4-(2-hydroxy-3-dodecyloxy-propoxy)phenyl]-4,6-bis(2,4-dimethylphenyl)-1,3,5-triazine, 2-(2-hydroxy-4-hexyloxy)phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxy-propoxy)phenyl]-1,3,5-triazine, 2-(2-hydroxyphenyl)-4-(4-methoxyphenyl)-6-phenyl-1,3,5-triazine, 2-{2-hydroxy-4-[3-(2-ethylhexyl-1-oxy)-2-hydroxypropyloxy]phenyl}-4,6-bis(2,4-dimethylphenyl)-1,3,5-triazine.
8. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, bis(2,6-di-tert-butyl-4-methylphenyl) pentaerythritol diphosphite, diisodecyloxypentaerythritol diphosphite, bis(2,4-di-tert-butyl-6-methylphenyl) pentaerythritol diphosphite, bis(2,4,6-tris(tert-butyl) phenyl pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-dibenzo[d,g]-1,3,2-dioxaphosphocin, bis(2,4-di-tert-butyl-6-methylphenyl) methyl phosphite, bis(2,4-di-tert-butyl-6-methylplenyl) ethyl phosphite, 6-fluoro-2,4,8,10-tetra-tert-butyl-12-methyl-dibenzo[d,g]-1,3,2-dioxaphosphocin, 2,2',2"-nitrilo [triethyl tris(3,3',5,5'-tetra-tert-butyl-1,1'-biphenyl-2,2'-diyl)phosphite], 2-ethylhexyl(3,3',5,5'-tetra-tert-butyl-1,1'-biphenyl-2,2'-diyl)phosphite, 5-butyl-5-ethyl-2-(2,4,6-tri-tert-butylphenoxy)-1,3,2-dioxaphosphirane.

Furthermore, it is possible to use additives customary in the art, such as antistatics, flow improvers and adhesion promoters.

Owing to the surface activity of the compounds of the invention it is also possible to use these compounds as flow improvers, either alone or in combination with further customary flow improvers.

The invention further provides for the use of compounds of the formula I as flow improvers, alone or in combination with further, customary flow improvers.

DIN 55945 defines levelling as "the more or less pronounced capacity of a still-liquid coating itself to compensate the unevennesses which arise in the course of its application." (cf. J. Bieleman, Lackadditive [Additives for Coatings], VCH Weinheim 1998, chapter 6). The levelling of a coating material depends greatly on its flow behaviour and on its surface tension. Flow improvers are substances which help wet coatings to become films which flow out evenly, by reducing the viscosity and/or surface tension. In the case of powder coating materials, flow improvers also lower the melt viscosity and the glass transition temperature and have an additional devolatilizing effect. Flow improvers are used to eliminate levelling defects or surface defects which detract from the overall appearance of the coating. Levelling defects or surface defects include the orange peel effect, formation of structures, cratering, fisheyes, sensitivity to draughts, substrate wetting problems, brush marks, runs, bittiness, pinholes, etc. The use of the compounds of the invention as flow improvers makes it possible to lower the surface tension. The surface tension may be calculated by determining the marginal angle of a drop of liquid on a surface (contact angle measurement).

In order to accelerate the photopolymerization it is possible to add, as further additives (D), amines, such as triethanolamine, N-methyldiethanolamine, ethyl p-dimethylaminobenzoate, or Michler's ketone. The effect of the amines may be boosted by adding aromatic ketones of the benzophenone type. Examples of amines which can be used as oxygen scavengers are substituted N,N-dialkylanilines, as described in EP-A 339841. Further accelerators, coinitiators and autoxidizers are thiols, thioethers, disulfides and phosphines, as described for example in EP 438123 and GB 2180358.

It is also possible to add chain transfer reagents customary in the art to the compositions of the invention. Examples are mercaptans, amines and benzothiazole.

The photopolymerization may further be accelerated by adding photosensitizers as further additives (D), which shift or broaden the spectral sensitivity. These photosensitizers are, in particular, aromatic carbonyl compounds such as benzophenone derivatives, thioxanthone derivatives, and also especially isopropylthioxanthone, anthraquinone derivatives and 3-acylcoumarin derivatives, terphenyls, styryl ketones, and also 3-(aroylmethylene)thiazolines, camphorquinone, and also eosine dyes, rhodamine dyes and erythrosine dyes.

The amines indicated above, for example, may also be regarded as photosensitizers.

The curing process, especially of compositions which are pigmented (with titanium dioxide for example), may also be assisted by adding an additional additive (D) which is a component which under thermal conditions forms free radicals, such as an azo compound, for instance 2,2'-azobis(4-methoxy-2,4-dimethylvaleronitrile), a triazene, diazo sulfide, pentazadiene or a peroxy compound such as hydroperoxide or peroxycarbonate, e.g. t-butyl hydroperoxide, as described for example in EP 245639.

As further additives (D), the compositions may also comprise, for example, a photoreducible dye, such as xanthene, benzoxanthene, benzothioxanthene, thiazine, pyronine, porphyrin or acridine dyes, and/or a radiation-cleavable trihalomethyl compound. Similar compositions are described, for example, in EP 445624.

Further common additives (D)—depending on the intended use—include optical brighteners, fillers, e.g. kaolin, talc, barytes, gypsum, chalk or silicatic fillers, pigments, dyes, wetting agents or flow improvers.

For the curing of thick and pigmented coatings it is appropriate to add glass microbeads or pulverized glass fibres, as described for example in U.S. Pat. No. 5,013,768.

The formulations may also comprise dyes and/or white or coloured pigments. Depending on the intended application, both organic and inorganic pigments may be used. Such additions are known to the person skilled in the art; some examples are titanium dioxide pigments, of, for example, the rutile or anatase type, carbon black, zinc oxide, such as zinc white, iron oxides, such as yellow iron oxide, red iron oxide, chrome yellow, chrome green, nickel titanium yellow, ultramarine blue, cobalt blue, bismuth vanadate, cadmium yellow or cadmium red. Examples of organic pigments are monoazo or disazo pigments, and also metal complexes thereof, phthalocyanine pigments, polycyclic pigments, such as perylene, anthraquinone, thioindigo, quinacridone or triphenylmethane pigments, and also diketopyrrolopyrrole, isoindolinone, e.g. tetrachloroisoindolinone, isoindoline, dioxazine, benzimidazolone and quinophthalone pigments.

The pigments may be used individually or else in a mixture in the formulations.

The pigments, depending on the intended use, are added to the formulations in the amounts customary in the art, for example in an amount of from 1 to 60% by weight, or from 10 to 30% by weight, based on the overall mass.

The formulations may also, for example, comprise organic dyes from a very wide variety of classes. Examples are azo dyes, methine dyes, anthraquinone dyes or metal complex dyes. Customary concentrations are, for example, from 0.1 to 20%, in particular from 1 to 5%, based on the overall mass.

The choice of additives is guided by the respective field of application and by the properties desired for this field. The above-described additives (D) are customary in the art and, accordingly, are used in the amounts that are customary in the art.

In certain cases it may be of advantage to use mixtures of two or more of the photoinitiators of the formula I; it is advantageous, for example, to use mixtures obtained directly in the preparation. It is of course also possible to use mixtures with known photoinitiators (E), examples being mixtures with camphorquinone, benzophenone, benzophenone derivatives, acetophenone, acetophenone derivatives, such as α-hydroxycycloalkyl phenyl ketones or 2-hydroxy-2-methyl-1-phenylpropanone, dialkoxyacetophenones, α-hydroxy- or α-aminoacetophenones, such as (4-methylthiobenzoyl)-1-methyl-1-morpholinoethane, (4-morpholinobenzoyl)-1-benzyl-1-dimethylaminopropane, 4-aroyl-1, 3-dioxolanes, benzoin alkyl ethers and benzil ketals, such as benzil dimethyl ketal, phenylglyoxalates and derivatives thereof, dimeric phenylglyoxalates, peresters, for example benzophenone-tetracarboxylic peresters as described for example in EP 126541, monoacylphosphine oxides, such as (2,4,6-trimethylbenzoyl)phenylphosphine oxide, bisacylphosphine oxides, such as bis(2,6-dimethoxybenzoyl)(2, 4,4-trimethylpent-1-yl)phosphine oxide, bis(2,4,6-trimethylbenzoyl)phenylphosphine oxide or bis(2,4,6-trimethylbenzoyl)(2,4-dipentoxyphenyl)-phosphine oxide, trisacylphosphine oxides, halomethyltriazines, e.g. 2-[2-(4-methoxyphenyl)-vinyl]-4,6-bistrichloromethyl[1,3,5]triazine, 2-(4-methoxyphenyl)-4,6-bistrichloromethyl-[1,3,5]triazine, 2-(3,4-dimethoxyphenyl)-4,6-bistrichloromethyl[1,3, 5]triazine, 2-methyl-4,6-bistrichloromethyl[1,3,5]triazine, hexaarylbisimidazole/coinitiator systems, e.g. ortho-chlorohexaphenylbisimidazole together with 2-mercaptobenzothiazole, ferrocenium compounds or titanocenes, such as dicyclopentadienylbis(2,6-difluoro-3-pyrrolophenyl)titanium or borate photoinitiators.

Where the photoinitiators of the invention are employed in hybrid systems, i.e. systems which can be cured both free-radically and cationically, use is made, in addition to the free-radical curing agents of the formula I and any further free-radical curing agents, of cationic photoinitiators such as benzoyl peroxide (other suitable peroxides are described in U.S. Pat. No. 4,950,581, column 19, lines 17-25), aromatic sulfonium, phosphonium or iodonium salts, as described for example in U.S. Pat. No. 4,950,581, column 18, line 60 to column 19, line 10.

The photopolymerizable compositions contain the photoinitiator appropriately in an amount of from 0.05 to 15% by weight, preferably from 0.1 to 5% by weight, based on the composition. The stated amount of photoinitiator is based on the sum of all of the added photoinitiators, if mixtures thereof are used, i.e. both on the photoinitiator (B) and on the photoinitiators (B)+(E).

The photopolymerizable compositions may be used for a variety of purposes: for example, as a printing ink, as a clearcoat material, as a white paint, as a chromatically pigmented paint, for wood or metal, for example, as powder coating materials, as coating material for, inter alia, paper, wood, metal or plastic, as a daylight-curable coating for the marking of buildings and roads, for photographic reproduction techniques, for holographic recording materials, for image recording techniques or for producing printing plates which can be developed with organic solvents or using aqueous alkalis, for producing masks for screen printing, as dental filling compounds, as adhesives, including pressure-sensitive adhesives, as laminating resins, as etch resists or permanent resists, both liquid and in the form of dry films, as photostructurable dielectrics, and as solder resists for electronic circuits, as resists for producing colour filters for any type of screen, or for producing structures in the production process of plasma displays and eletroluminescent displays, for the production of optical switches, optical lattices (interference grids), for the production of three-dimensional articles by mass curing (UV curing in transparent moulds) or by the stereolithography process, as described for example in U.S. Pat. No. 4,575,330, for producing composite materials (e.g. styrenic polyesters which may where appropriate contain glass fibres and/or other fibres and other auxiliaries), and of gel coats and high-film-build compositions, for the coating or sealing of electronic components, or as coatings for optical fibres. The compositions are suitable, furthermore, for the production of optical lenses, e.g. contact lenses or Fresnel lenses, and also for producing medical instruments, aids or implants.

The compositions may also be used to produce gels having thermotropic properties, as described for example in DE 19700064 and EP 678534.

The compounds of the formula I may additionally be used as initiators for emulsion, bead or suspension polymerizations or as initiators in a polymerization for the fixing of states of order of liquid-crystalline monomers and oligomers, or as initiators for the fixing of dyes on organic materials.

The photocurable compositions of the invention are suitable, for example, as coating materials for substrates of all kinds, e.g. wood, textiles, paper, ceramic, glass, plastics such as polyesters, polyethylene terephthalate, polyolefins or cellulose acetate, especially in the form of films, and also metals such as Al, Cu, Ni, Fe, Zn, Mg or Co and GaAs, Si or $SiO_2$, to which a protective coat or—by imagewise exposure—an image is to be applied.

The substrates may be coated by applying a liquid composition, a solution or suspension to the substrate. The choice of solvent and the concentration are guided primarily by the nature of the composition and by the coating technique. The solvent should be inert, i.e. it should not enter into any chemical reaction with the components and it should be able to be removed again in the course of drying after coating. Examples of suitable solvents are ketones, ethers and esters, such as methyl ethyl ketone, isobutyl methyl ketone, cyclopentanone, cyclohexanone, N-methylpyrrolidone, dioxane, tetrahydrofuran, 2-methoxyethanol, 2-ethoxyethanol, 1-methoxy-2-propanol, 1,2-dimethoxyethane, ethyl acetate, n-butyl acetate and ethyl 3-ethoxypropionate The formulation is applied uniformly to a substrate by means of known coating techniques, for example by spin-coating, dipping, knife coating, curtain coating techniques, brush application, spraying, especially by electrostatic spraying, and reverse roll coating, and also by electrophoretic deposition. It is also possible to apply the photosensitive layer to a temporary flexible support and then, by layer transfer via lamination, to the final substrate.

The application (coat thickness) and nature of the substrate (coat support) are dependent on the desired field of application. The dry film thickness range generally embraces values from about 0.1 μm to more than 100 μm, preferably from 0.02 to 2 cm.

A further field of use of photocuring is that of metal coating, as in the coating of metal sheets and tubes, cans or bottle closures, for example, and also photocuring on polymer coatings, for example PVC-based wall or floor coverings.

Examples of the photocuring of paper coatings are the colourless varnishing of labels, record sleeves or book covers.

The photosensitivity of the compositions of the invention generally ranges from about 200 nm to about 600 nm (UV region). Suitable radiation is present, for example, in sunlight or light from artificial sources. Light sources employed therefore include a large number of a very wide variety of types. Both point sources and arrays (lamp carpets) are suitable. Examples are carbon arc lamps, xenon arc lamps, medium-, high- and low-pressure mercury lamps, possibly doped with metal halides (metal-halogen lamps), microwave-excited metal vapour lamps, excimer lamps, superactinic fluorescent tubes, fluorescent lamps, argon incandescent lamps, flashlights, photographic floodlamps, light-emitting diodes (LEDs), electron beams and X-rays. The distance between the lamp and the substrate to be exposed may vary depending on the intended application and the type and output of the lamps, for example between 2 cm and 150 cm.

As already mentioned, curing in the process of the invention may take place solely by exposure to electromagnetic radiation. Depending on the composition of the formulation to be cured, however, thermal curing before, during or after radiation exposure is appropriate.

Thermal curing takes place in accordance with methods known to the person skilled in the art. Curing is generally carried out in an oven, e.g. a forced-air oven, on a hotplate, or by irradiation using IR lamps. Curing without auxiliaries at room temperature is likewise possible, depending on the binder system used. The curing temperatures are generally between room temperature and 150° C., e.g. 25-150° C. or 50-150° C. In the case of powder coating materials or coil coating materials, the curing temperatures may also be higher, e.g. up to 350° C.

Where the formulation includes thermally curable components (C), it is additionally possible in accordance with the invention to add thermal drying catalysts or curing catalysts to the formulation as additional additives (D). Examples of possible drying catalysts, or thermal curing catalysts, are organometallic compounds, amines and/or phosphines. Organometallic compounds are, for example, metal carboxylates, especially those of the metals Pb, Mn, Co, Zn, Hf, Zr or Cu, or metal chelates, especially those of metals Al, Ti, Hf or Zr, or organometallic compounds such as organotin compounds. Examples of metal carboxylates are the stearates of Pb, Mn or Zn, the octoates of Co, Zn or Cu, the naphthenates of Mn and Co or the corresponding linoleates or tallates. Examples of metal chelates are the aluminium, titanium or zirconium chelates of acetylacetone, ethyl acetylacetate, salicylaldehyde, salicylaldoxime, o-hydroxyacetophenone or ethyl trifluoroacetylacetate and the alkoxides of these metals. Examples of organotin compounds are dibutyltin oxide, dibutyltin dilaurate and dibutyltin dioctoate. Examples of amines are, in particular, tertiary amines, such as tributylamine, triethanolamine, N-methyldiethanolamine, N-dimethylethanolamine, N-ethylmorpholine, N-methylmorpholine or diazabicyclooctane (triethylenediamine) and also the salts thereof. Further examples are quaternary ammonium salts, such as trimethylbenzylammonium chloride; As curing catalysts it is also possible to use phosphines, such as triphenylphosphine. Suitable catalysts are described, for example, as well in J. Bieleman, Lackadditive [Additives for Coatings], Wiley-VCH Verlag GmbH, Weinheim, 1998, page 244-247. Examples are sulfonic acids, such as p-toluenesulfonic acid, dodecylbenzenesulfonic acid, dinonyinaphthalenesulfonic acid or dinonylnaphthalenedisulfonic acid. For example, it is also possible to use latent or blocked sulfonic acids, where the blocking of the acid may be ionogenic or non-ionogenic.

Such catalysts are used in the concentrations known to the person skilled in the art and customary in that art.

The invention also provides a process for photopolymerizing non-volatile monomeric, oligomeric or polymeric compounds containing at least one ethylenically unsaturated double bond, which comprises exposing a composition as described above to electromagnetic radiation in the range from 200 to 600 nm.

The invention additionally provides for the use of the above-described composition and to a process for producing pigmented and unpigmented paints and varnishes, powder coating materials, gel coats, composite materials or glass fibre cable coatings.

The invention likewise provides a coated substrate coated on at least one surface with a composition as described above.

The examples which follow illustrate the invention, but do not indicate any intention that the invention be restricted to the examples. As in the remainder of the description and in the claims, parts and percentages are by weight unless indicated otherwise. References to alkyl radicals containing more than three carbon atoms without indication of the isomer should be understood in each case as referring to the n-isomers

EXAMPLES

Preparation of the Starting Compounds:

A.1: Preparation of hex-5-enyl glyoxalate

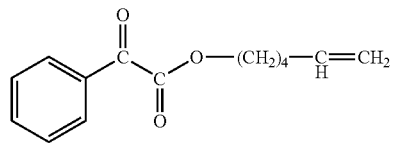

A mixture of 25 g of methyl benzoylformate (methyl glyoxalate), 15.25 g of 5-hexen-1-ol and 1.02 g of p-toluenesulfonic acid is heated at 120° C. for 18 hours. The methanol formed is removed by distillation. The mixture is poured into water (70 ml) and extracted with ethyl acetate. The organic phases are washed with water and dried over magnesium sulfate. Filtration, evaporation of the solvent, chromatography (eluent: 3:1 hexanethyl acetate) and distillation (b.p.=115° C. at 0.006 mbar) give hex-5-enyl glyoxalate (22.8 g, 64%) as a pale yellowish liquid.

$^1$H-NMR (CDCl$_3$) δ [ppm]: 7.99(m, 2 H arom.); 7.65 (m, 1 H arom.); 7.50 (m, 2 H arom.); 5.82 (m, 1 H, —CH=CH$_2$); 4.98 (m, 2 H, —CH=CH$_2$); 4.40 (m, 2 H, CH$_2$—O—C(O)—); 2.14 (m, 2 H, —CH$_2$—); 1.81 (m, 2 H, —CH$_2$—); 1.53 (m, 2 H, —CH$_2$—).

A.2: Preparation of but-3-enyl glyoxalate

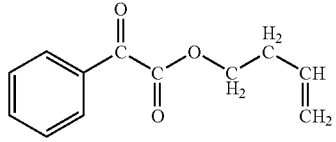

In a flask with a water separator, a mixture of 11.02 g of benzoylformic acid (glyoxalic acid), 6.62 g of 3-buten-1-ol and 0.42 g of p-toluenesulfonic acid in 130 ml of toluene is heated at 110° C. for 22 hours. The solution is washed with saturated NaHCO$_3$ solution and water. The organic phases are dried over sodium sulfate. Filtration, evaporation of the solvent and distillation (b.p.=85° C. at 0.035 mbar) give but-3-enyl glyoxalate (8.08 g, 54%) as a pale yellowish liquid.

$^1$H-NMR (CDCl$_3$) δ [ppm]: 7.97 (m, 2 H arom.); 7.47 (m, 1 H arom.); 7.30 (m, 2 H arom.); 5.79 (m, 1 H, —CH=CH$_2$); 5.14 (m, 2 H, —CH=CH$_2$); 4.43 (t, J=6.6, 2 H, CH$_2$—O); 2.51 (dt, J=6.9, J=13.5, 2 H, —CH$_2$—CH$_2$—O).

A.3: Preparation of 2-allyloxyethyl glyoxalate

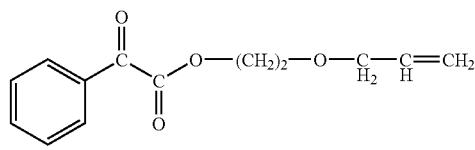

A solution of 16 g of methyl benzoylformate (methyl glyoxalate), 13.6 g of 2-(allyloxy)ethanol and 0.6 g of p-toluenesulfonic acid in 200 ml of toluene is heated at reflux for 4.5 hours. The mixture is poured into saturated NaHCO$_3$ solution and the phases are separated. The organic phases are washed with water and dried over sodium sulfate. Filtration, evaporation of the solvent and distillation (b.p.=121° C. at 0.05 mbar) give 2-allyloxyethyl glyoxalate (18.7 g, 75%) as a pale yellowish liquid.

$^1$H-NMR (CDCl$_3$) δ [ppm]: 7.93 (m, 2 H arom.); 7.55 (m, 1 H arom.); 7.40 (m, 2 H arom.); 5.80 (m, 1 H, —CH=CH$_2$); 5.16 (m, 2 H, —CH=CH$_2$); 4.45 (t, J=4.8, 2 H, CH$_2$—O—C(O)—); 3.95 (d, J=5.7, 2 H, —CH$_2$—CH=CH$_2$); 3.67 (t, J=2 H, —C(O)—O—CH$_2$—CH$_2$—O—).

A.4: Preparation of 1-allylbut-3-enyl glyoxalate

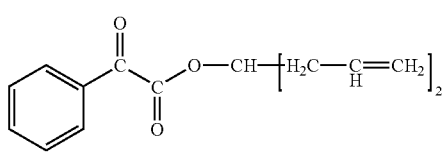

The compound of Example A.4 is prepared by the method described in Example A.3 using 1.1 mole equivalents of 1,6-heptadien-4-ol as the alcohol.

$^1$H-NMR (CDCl$_3$) δ [ppm]: 7.76 (m, 2 H arom.); 7.43(m, 1 H arom.); 7.26 (m, 2 H arom.); 5.60 (m, 2 H, 2 —CH=CH$_2$); 5.10 (m, 1 H, —C(O)—O—CH—); 4.97 (m, 4 H, 2 —CH=CH$_2$); 2.26 (m, 4 H, 2 —CH$_2$—CH=CH$_2$).

A.5: Preparation of 2,2-bisallyloxymethylbutyl glyoxalate

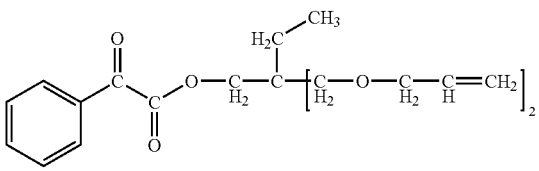

The compound of Example A.5 is prepared by the method described in Example A.3 using 1.5 mole equivalents of trimethylolpropane diallyl ether as the alcohol.

$^1$H-NMR (CDCl$_3$) δ [ppm]: 7.97 (m, 2 H arom.); 7.63 (m, 1 H arom.); 7.48 (m, 2 H arom.); 5.87 (m, 2 H, 2 —CH=CH$_2$); 5.18 (m, 4 H, 2 —CH=CH$_2$); 4.38 (m, 2 H, —C(O)—O—CH$_2$); 3.87 (m, 4 H, 2 —O—CH$_2$—CH=CH$_2$); 3.36 (m, 4 H, 2 —CH$_2$—O—CH$_2$—CH=CH$_2$); 1.50 (q, 2H, J=7.5, —CH$_2$—CH$_3$); 0.90 (t, 3 H, J=7.5, —CH$_2$—CH$_3$).

A.6: Preparation of 3-allyloxy-2,2-bisallyloxymethylpropyl Glyoxalate

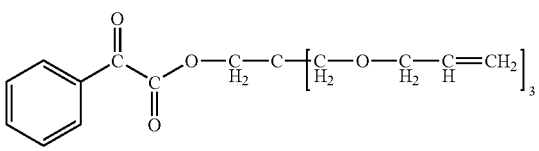

The compound of Example A.6 is prepared by the method described in Example A.3 using 1.5 mole equivalents of pentaerythritol triallyl ether as the alcohol.

$^1$H-NMR (CDCl$_3$) δ [ppm]: 8.0-17.23 (m, 5 H arom.); 5.84 (m, 3 H, 3 —CH=CH$_2$); 5.17 (m, 6 H, 3 —CH=CH$_2$); 4.48 (s, 2 H, —C(O)—O—CH$_2$); 3.94 (m, 6 H, 3 —O—CH$_2$—CH=CH$_2$); 3.49 (s, 6 H, 3 —CH$_2$—O—CH$_2$—CH=CH$_2$).

A.7: Preparation of 2-allyloxymethyl-2-(2-oxo-2-phenylacetoxymethyl)butyl oxophenylacetate

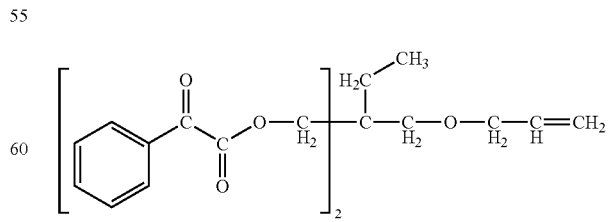

A solution of 15 g of benzoylformic acid (glyoxalic acid), 7.95 g of trimethylolpropane monoallyl ether and 1.11 g of 4-dimethylaminopyridine in 750 ml of methylene chloride is cooled to 0° C. A solution of 18.8 g of N,N'-dicyclohexyl-carbodiimide in 80 ml of methylene chloride is added dropwise over the course of 30 minutes. The mixture is warmed to room temperature and stirred overnight. Filtration, evaporation of the solvent and chromatography (eluent 6:1 methylene chloride/ethyl acetate) give 2-allyloxymethyl-2-(2-oxo-2-phenylacetoxymethyl)butyl oxophenylacetate (9.43 g, 47%) as a yellow liquid.

$^1$H-NMR (CDCl$_3$) δ [ppm]: 7.98 (m, 4 H arom.); 7.62 (m, 2 H arom.); 7.50 (m, 4 H arom.); 5.86 (m, 1 H, —C$\underline{H}$=CH$_2$); 5.20 (m, 2 H, —CH=C$\underline{H}_2$); 4.40 (s, 4 H, 2 —C(O)—O—C$\underline{H}_2$); 3.95 (m, 2 H, —O—C$\underline{H}_2$—CH=CH$_2$); 3.41 (s, 2 H, —C$\underline{H}_2$—O—CH$_2$—CH=CH$_2$); 1.58 (q, J=7.5, 2 H, —C$\underline{H}_2$—CH$_3$); 0.94 (t, J=7.5, 3 H, —CH$_2$—C$\underline{H}_3$).

A.8: Preparation of 1-allyloxymethyl-2-(2-oxo-2-phenylacetoxy)ethyl Oxophenylacetate

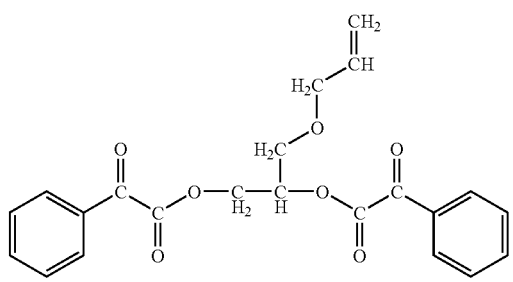

The compound of Example A.8 is prepared by the method described in Example A.7 using 2.2 mole equivalents of benzoylformic acid (glyoxalic acid) and 1 mole equivalent of 3-allyloxy-1,2-propanediol.

$^1$H-NMR (CDCl$_3$) δ [ppm]: 7.99 (m, 4 H arom.); 7.61 (m, 2 H arom.); 7.45 (m, 4 H arom.); 5.86 (m, 1 H, —C$\underline{H}$=CH$_2$); 5.71 (m, 1 H, —C(O)—O—CH—); 5.24 (m, 2 H, —CH=C$\underline{H}_2$); 4.82 (dd, J=3, J=12, 1 H, —C(O)—O—C$\underline{H}_2$); 4.82 (dd, J=9, J=12, 1 H, —C(O)—O—C$\underline{H}_2$); 4.04 (m, 2 H, —O—C$\underline{H}_2$—CH=CH$_2$); 3.77 (d, J=6, 2 H, —C$\underline{H}_2$—O—CH$_2$—CH=CH$_2$).

A.9: Preparation of 2-(2-oxo-2-phenylacetoxymethyl)pent-4-enyl oxophenylacetate

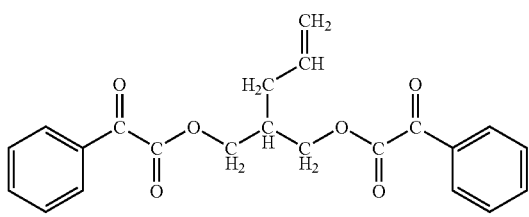

The compound of Example A.9 is prepared by the method described in Example A.7 using 2.2 mole equivalents of benzoylformic acid and 1 mole equivalent of 2-allylpropane-1,3-diol.

$^1$H-NMR (CDCl$_3$) δ [ppm]: 7.99 (m, 4 H arom.); 7.64 (m, 2 H arom.); 7.49 (m, 4 H arom.); 5.80 (m, 1 H, —C$\underline{H}$=CH$_2$); 5.15 (m, 2 H, —CH=C$\underline{H}_2$); 4.44 (m, 4 H, 2 —C(O)—O—C$\underline{H}_2$); 2.41 (m, 1 H, (—C(O)—O—C$\underline{H}_2$)$_2$—C$\underline{H}$—); 2.27 (m, 2 H, —C$\underline{H}_2$—CH=CH$_2$).

INVENTIVE EXAMPLES

Example 1

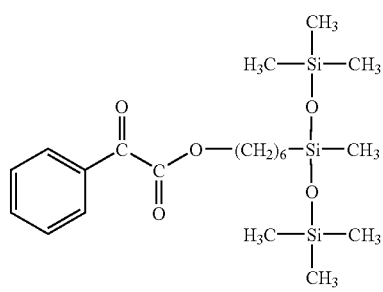

(R=radical of the formula II, R$_1$, R$_2$, R$_3$, R$_4$, R$_5$=H, r=s=1, Y=—(CH$_2$)$_6$—, A=radical of the formula III, R$_{13}$, R$_{17}$, R$_{18}$, R$_{19}$, R$_{20}$, R$_{21}$, R$_{22}$=CH$_3$, n=1, m=p=0, x=1)

A mixture of one equivalent of the compound prepared as described in A.1 and one equivalent of 1,1,1,3,5,5,5-heptamethyltrisiloxane in toluene is heated in the presence of 0.004 equivalent (120 ppm, based on the Pt content) of a carbon-supported Pt catalyst at 100° C. for 20 hours. The mixture is then filtered through silica gel. Filtration and evaporation of the solvent give the compound quantitatively as an oil.

U.V. (CH$_3$CN) max. at 254 nm (ε 12 751). $^1$H NMR (CDCl$_3$) δ [ppm]: 7.89 (m, 2 H arom.); 7.52 (m, 1 H arom.); 7.41 (m, 2 H arom.); 4.30 (m, 2 H, —CH$_2$—O—C(O)); 1.66 (m, 2 H, —C$\underline{H}_2$—CH$_2$—O—C(O)); 1.25 (m, 6 H, —(C$\underline{H}_2$)$_3$—CH$_2$—CH$_2$—O—C(O)); 0.37 (m, 2 H, —CH$_2$—Si—); 0.01 (m, 21 H, 7 Si—CH$_3$). m/z (Cl) 455 (MH$^+$); according to the mass spectrum there is also a further compound present in a small amount: 235 (MH$^+$).

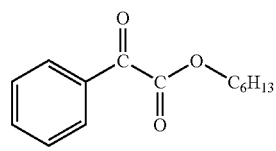

M = 234

Example 2

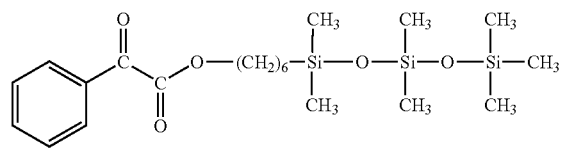

(R=radical of the formula II, $R_1$, $R_2$, $R_3$, $R_4$, $R_5$=H, r=s=1, Y=—$(CH_2)_6$—, A=radical of the formula III, $R_{13}$, $R_{15}$, $R_{16}$, $R_{20}$, $R_{21}$, $R_{22}$, $G_1$=$CH_3$, n=p=1, m=0, x=1)

The compound of Example 2 is prepared by the method described in Example 1 using 1 mole equivalent of the compound prepared as described in A.1 and 1 mole equivalent of 1,1,1,3,3,5,5-heptamethyltrisiloxane.

U.V. ($CH_3CN$) max. at 254 nm ($\epsilon$ 12 550). $^1$H NMR ($CDCl_3$) δ [ppm]: 7.89 (m, 2 H arom.); 7.56 (m, 1 H arom.); 7.41 (m, 2 H arom.); 4.30 (m, 2 H, —$CH_2$—O—C(O)); 1.66 (m, 2 H, —$C\underline{H}_2$—$CH_2$—O—C(O)); 1.28 (m, 6 H, —($C\underline{H}_2)_3$—$CH_2$—$CH_2$—O—C(O)); 0.45 (m, 2 H, —$CH_2$—Si—); 0.01 (m, 21 H, 7 Si—$CH_3$). m/z (Cl) 455 ($MH^+$); according to the mass spectrum there are also further compounds present in a small amount: 529 ($MH^+$); 235 ($MH^+$).

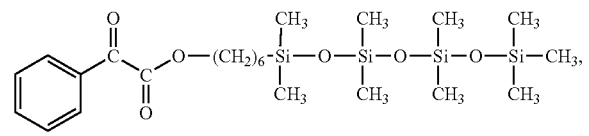

M = 528

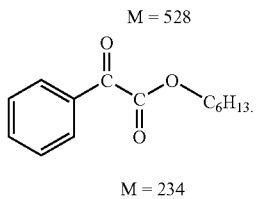

M = 234

Example 3

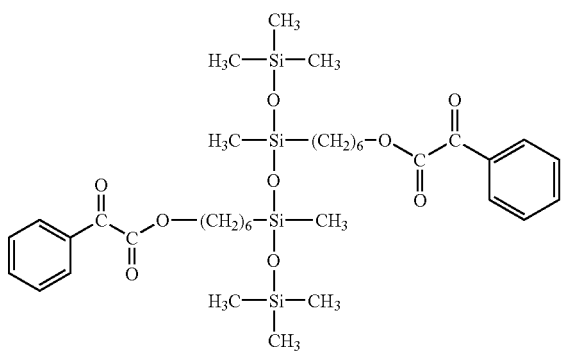

(R=radical of the formula II, $R_1$, $R_2$, $R_3$, $R_4$, $R_5$=H, r=1, s=2, Y=—$(CH_2)_6$—, A=radical of the formula III, $R_{13}$, $R_{17}$, $R_{18}$, $R_{19}$, $R_{20}$, $R_{21}$, $R_{22}$=$CH_3$, n=2, m=p=0, x=1)

The compound of Example 3 is prepared by the method described in Example 1 using 2 mole equivalents of the compound prepared as described in A.1 and 1 mole equivalent of 1,1,1,3,5,7,7,7-octamethyltetrasiloxane.

U.V. ($CH_3CN$) max. at 254 nm ($\epsilon$ 23 079). $^1$H NMR ($CDCl_3$) δ [ppm]: 8.16 (m, 4 H arom.); 7.88 (m, 2 H arom.); 7.36 (m, 4 H arom.); 4.28 (m, 4 H, 2 —$CH_2$—O—C(O)); 1.53 (m, 4 H, 2 —$C\underline{H}_2$—$CH_2$—O—C(O)); 1.21 (m, 12 H, 2 —($C\underline{H}_2)_3$—$CH_2$—$CH_2$—O—C(O)); 0.77 (m, 4 H, 2 —$CH_2$—Si—); 0.01 (m, 24 H, 8 Si—$CH_3$). m/z (Cl) 746 ($M^+$).

Example 4

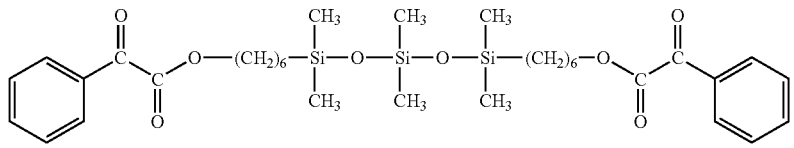

(R=radical of the formula II, $R_1$, $R_2$, $R_3$, $R_4$, $R_5$=H, r=1, s=2, Y=—$(CH_2)_6$—, A=radical of the formula III, $R_{13}$, $R_{15}$, $R_{16}$, $G_1$, $G_2$=$CH_3$, n=2, m=0, p=1, x=1)

The compound of Example 4 is prepared by the method described in Example 1 using 2 mole equivalents of the compound prepared as described in A.1 and 1 mole equivalent of 1,1,3,3,5,5-hexamethyltrisiloxane.

U.V. ($CH_3CN$) max. at 254 nm ($\epsilon$ 24 552). $^1$H NMR ($CDCl_3$) δ [ppm]: 7.95 (m, 4 H arom.); 7.63 (m, 2 H arom.); 7.45 (m, 4 H arom.); 4.33 (m, 4 H, 2 —$CH_2$—O—C(O)); 1.55 (m, 4 H, 2 —$C\underline{H}_2$—$CH_2$—O—C(O)); 1.26 (m, 12 H, 2 —($C\underline{H}_2)_3$—$CH_2$—$CH_2$—O—C(O)); 0.47 (m, 4 H, 2 —$CH_2$—Si—); 0.01 (m, 18 H, 6 Si—$CH_3$). m/z (Cl) 672 ($M^+$); according to the mass spectrum there are also further compounds present in a small amount: 968 ($M^+$); 894 ($M^+$); 820 ($M^+$); 746 ($M^+$); 598 ($M^+$).

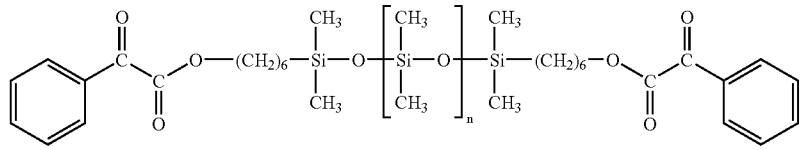

```
n = 5    M = 968    n = 2    M = 746
n = 4    M = 894    n = 0    M = 598
n = 3    M = 820
```

Example 5

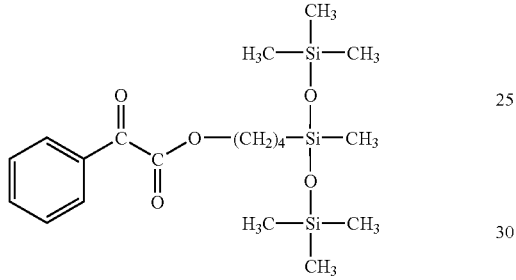

(R=radical of the formula II, $R_1$, $R_2$, $R_3$, $R_4$, $R_5$=H, r=s=1, Y=—(CH$_2$)$_4$—, A=radical of the formula III, $R_{13}$, $R_{17}$, $R_{18}$, $R_{19}$, $R_{20}$, $R_{21}$, $R_{22}$=CH$_3$, n=1, m=p=0, x=1)

The compound of Example 5 is prepared by the method described in Example 1 using 1 mole equivalent of the compound prepared as described in A.2 and 1 mole equivalent of 1,1,1,3,5,5,5-heptamethyltrisiloxane.

U.V. (CH$_3$CN) max. at 254 nm ($\epsilon$ 24 552). $^1$H NMR (CDCl$_3$) δ [ppm]: 7.93 (m, 2 H arom.); 7.57 (m, 1 H arom.); 7.41 (m, 2 H arom.); 4.35 (m, 2 H, —CH$_2$—O—C(O)); 1.74 (m, 2 H, —CH$_2$—CH$_2$—O—C(O)); 1.38 (m, 2 H, —CH$_2$—CH$_2$—CH$_2$—O—C(O)); 0.44 (m, 2 H, —CH$_2$—Si—); 0.01 (m, 21 H, 7 Si—CH$_3$). m/z (CI) 426 (M$^+$); according to the mass spectrum there are also further compounds present in a small amount: 426 (M$^+$; isomer); 206 (M$^+$); 204 (M$^+$).

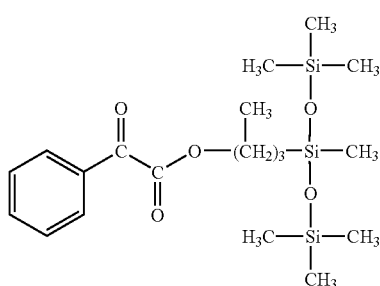

M = 426

-continued

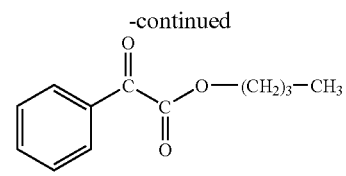

M = 206

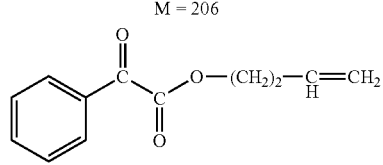

M = 204

Example 6

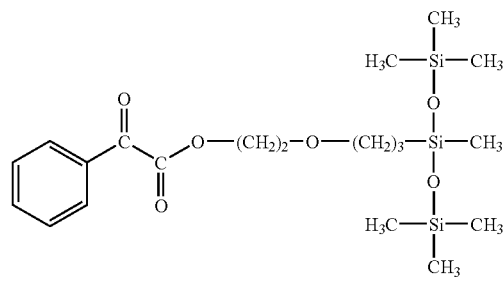

(R=radical of the formula II, $R_1$, $R_2$, $R_3$, $R_4$, $R_5$=H, r=s=1, Y=—(CH$_2$)$_2$—O—(CH$_2$)$_3$—, A=radical of the formula III, $R_{13}$, $R_{17}$, $R_{18}$, $R_{19}$, $R_{20}$, $R_{21}$, $R_{22}$=CH$_3$, n=1, m=p=0, x=1)

The compound of Example 6 is prepared by the method described in Example 1 using 1 mole equivalent of the compound prepared as described in A.3 and 1 mole equivalent of 1,1,1,3,5,5,5-heptamethyltrisiloxane.

U.V. (CH$_3$CN) max. at 254 nm ($\epsilon$ 12 600). $^1$H NMR (CDCl$_3$) δ [ppm]: 7.93 (m, 2H arom.); 7.54 (m, 1 H arom.); 7.39 (m, 2 H arom.); 4.43 (m, 2 H, —CH$_2$—O—C(O)); 3.66 (t, J=6, 2 H, —CH$_2$—CH$_2$—O—C(O)); 3.37 (t, J=6, 2 H, —CH$_2$—O—CH$_2$—CH$_2$—O—C(O)); 1.49 (m, 2 H, —CH$_2$—CH$_2$—Si—); 0.39 (m, 2 H, —CH$_2$—Si—); 0.01 (m, 21 H, 7 Si—CH$_3$). m/z (CI) 457 (MH$^+$); according to the mass spectrum there are also further compounds present in a small amount: 237 (MH$^+$); 195 (MH$^+$).

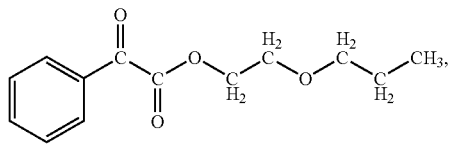

M = 236

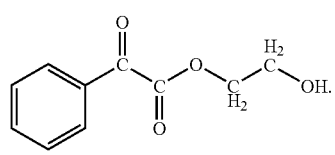

M = 194

Example 7

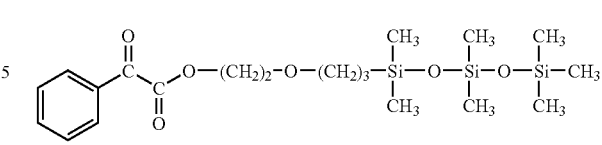

(R=radical of the formula II, $R_1$, $R_2$, $R_3$, $R_4$, $R_5$=H, r=s=1, Y=—$(CH_2)_2$—O—$(CH_2)_3$—, A=radical of the formula III, $R_{13}$, $R_{15}$, $R_{16}$, $R_{20}$, $R_{21}$, $R_{22}$, $G_1$=$CH_3$, n=p=1, m=0, x=1)

The compound of Example 7 is prepared by the method described in Example 1 using 1 mole equivalent of the compound prepared as described in A.3 and 1 mole equivalent of 1,1,1,3,3,5,5-heptamethyltrisiloxane.

U.V. ($CH_3CN$) max. at 254 nm ($\epsilon$ 12 600). $^1$H NMR ($CDCl_3$) δ [ppm]: 7.90 (m, 2 H arom.); 7.53 (m, 1 H arom.); 7.40 (m, 2 H arom.); 4.43 (m, 2 H, —$CH_2$—O—C(O)); 3.65 (m, 2 H, —$CH_2$—$CH_2$—O—C(O)); 3.37 (m, 2 H, —$CH_2$—O—$CH_2$—$CH_2$—O—C(O)); 1.54 (m, 2 H, —$CH_2$—$CH_2$—Si—); 0.44 (m, 2 H, —$CH_2$—Si—); 0.01 (m, 21 H, 7 Si—$CH_3$). m/z (CI) 457 (MH$^+$); according to the mass spectrum there are also further compounds present in a small amount: 531 (MH$^+$); 237 (MH$^+$); 195 (MH$^+$).

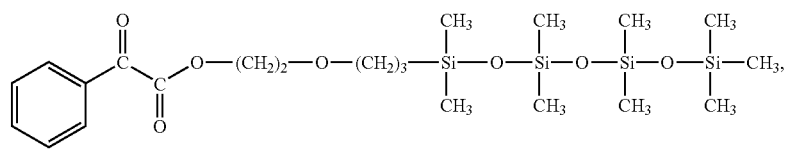

M = 530

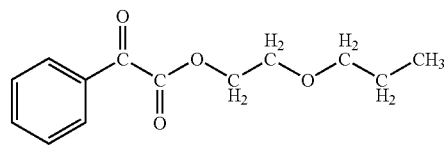

M = 236

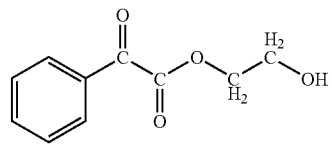

M = 194

Example 8

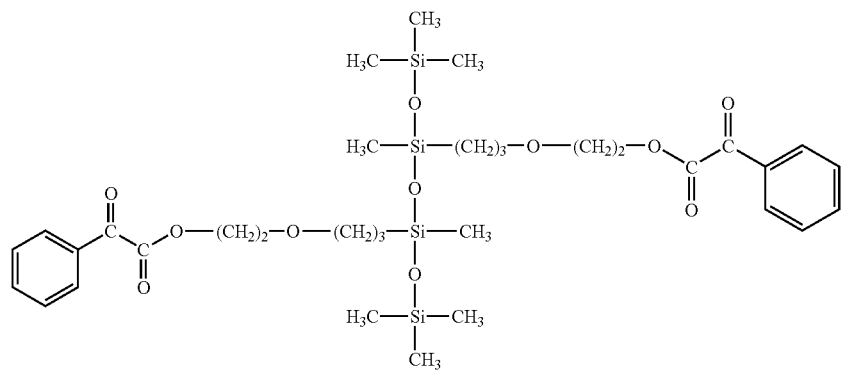

(R=radical of the formula II, $R_1$, $R_2$, $R_3$, $R_4$, $R_5$=H, r=1, s=2, Y=—(CH$_2$)$_2$—O—(CH$_2$)$_3$—, A=radical of the formula III, $R_{13}$, $R_{17}$, $R_{18}$, $R_{19}$, $R_{20}$, $R_{21}$, $R_{22}$=CH$_3$, n=2, m=p=0, x=1)

The compound of Example 8 is prepared by the method described in Example 1 using 2 mole equivalents of the compound prepared as described in A.3 and 1 mole equivalent of 1,1,1,3,5,7,7,7-octamethyltetrasiloxane.

U.V. (CH$_3$CN) max. at 254 nm ($\epsilon$ 21 731). $^1$H NMR (CDCl$_3$) $\delta$ [ppm]: 7.93 (m, 4 H arom.); 7.56 (m, 2 H arom.); 7.41 (m, 4 H arom.); 4.43 (m, 4 H, 2 —CH$_2$—O—C(O)); 3.65 (m, 4 H, 2 —CH$_2$—O—CH$_2$—CH$_2$—O—C(O)); 3.37 (m, 4 H, 2 —CH$_2$—CH$_2$—O—C(O)); 1.54 (m, 4 H, 2 —CH$_2$—CH$_2$—Si—); 0.42 (m, 4 H, 2 —CH$_2$—Si—); 0.01 (m, 24 H, 8 Si—CH$_3$). m/z (Cl) 750 (M$^+$); according to the mass spectrum there are also further compounds present in a small amount: 898 (M$^+$); 1046 (M$^+$).

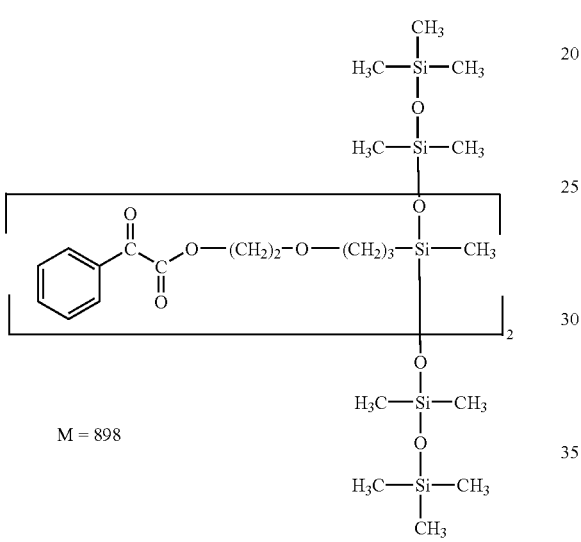

M = 898

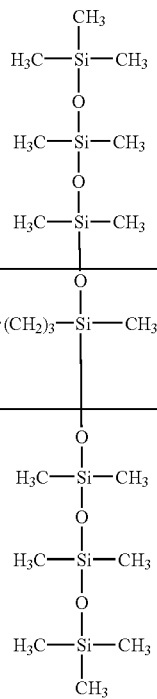

M = 1046

Example 9

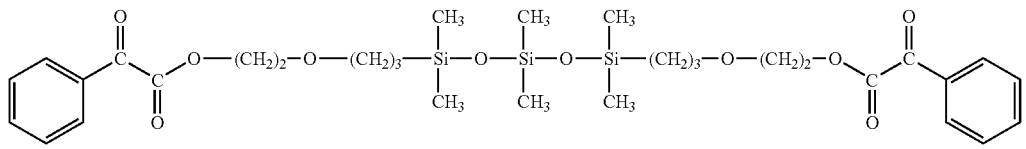

(R=radical of the formula II, $R_1$, $R_2$, $R_3$, $R_4$, $R_5$=H, r=1, s=2, Y=—(CH$_2$)$_2$—O—(CH$_2$)$_3$—, A=radical the formula III, $R_{13}$, $R_{15}$, $R_{16}$, $G_1$, $G_2$=CH$_3$, n=2, m=0, p=1, x=1)

The compound of Example 9 is prepared by the method described in Example 1 using 2 mole equivalents of the compound prepared as described in A.3 and 1 mole equivalent of 1,1,3,3,5,5-hexamethyltrisiloxane.

U.V. (CH$_3$CN) max. at 254 nm ($\epsilon$ 23 844). $^1$H NMR (CDCl$_3$) $\delta$ [ppm]: 7.95 (m, 4 H arom.); 7.57 (m, 2 H arom.); 7.44 (m, 4 H arom.); 4.48 (m, 4 H, 2 —CH$_2$—O—C(O)); 3.69 (m, 4 H, 2 —CH—O—CH$_2$—CH$_2$—O—C(O)); 3.40 (m, 4 H, 2 —CH$_2$—CH$_2$—O—C(O)); 1.55 (m, 4 H, 2 —CH$_2$—CH$_2$—Si—); 0.47 (m, 4 H, 2 —CH$_2$—Si—); 0.01 (m, 18 H, 6 Si—CH$_3$). m/z (Cl) 676 (M$^+$); according to the mass spectrum there are also further compounds present in a small amount: 1120 (M$^+$); 1046 (M$^+$); 972 (M$^+$); 898 (M$^+$); 824 (M$^+$); 750 (M$^+$); 602 (M$^+$); 528 (M$^+$).

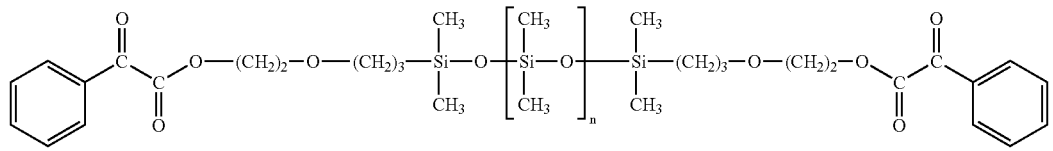

n = 7   M = 1120   n = 3   M = 824
n = 6   M = 1046   n = 2   M = 750
n = 5   M = 972    n = 0   M = 602
n = 4   M = 898

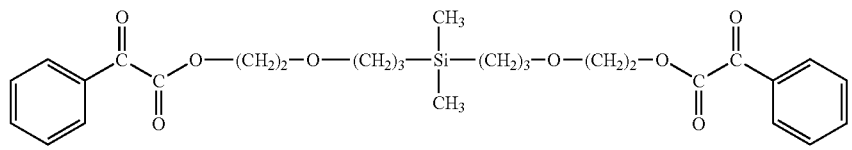

M = 528

Example 10

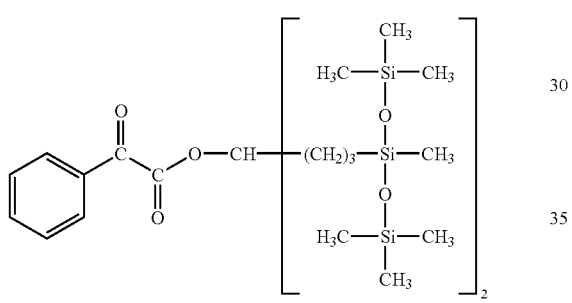

(R=radical of the formula II, $R_1$, $R_2$, $R_3$, $R_4$, $R_5$=H, r=s=1, Y=—CH—$((CH_2)_3)_2$—, A=radical of the formula III, $R_{13}$, $R_{17}$, $R_{18}$, $R_{19}$, $R_{20}$, $R_{21}$, $R_{22}$=$CH_3$, n=1, m=p=0, x=2)

The compound of Example 10 is prepared by the method described in Example 1 using 1 mole equivalent of the compound prepared as described in A.4 and 2 mole equivalents of 1,1,1,3,5,5,5-heptamethyltrisiloxane.

U.V. ($CH_3CN$) max. at 254 nm ($\epsilon$ 13 006). $^1$H NMR ($CDCl_3$) δ [ppm]: 7.92 (m, 2 H arom.); 7.44 (m, 1 H arom.); 7.27 (m, 2 H arom.); 5.14 (m, 1 H, —CH—O—C(O)); 1.60 (m, 4 H, 2 —C$\underline{H}_2$—$CH_2$—$CH_2$—Si—); 1.35 (m, 4 H, 2 —C$\underline{H}_2$—$CH_2$—Si—); 0.42 (m, 4 H, 2 —$CH_2$—Si—); 0.01 (m, 42 H, 14 Si—$CH_3$). m/z (CI) 689 ($MH^+$); according to the mass spectrum there are also further compounds present in a small amount: 469 ($MH^+$); 249 ($MH^+$).

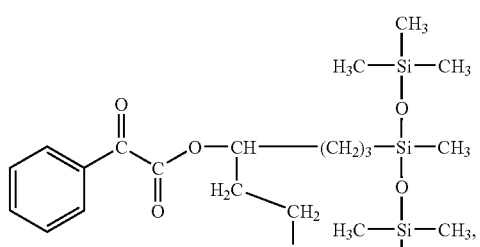

M = 468

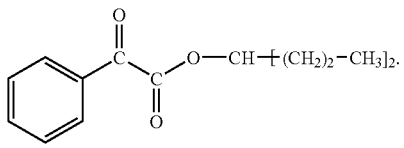

M = 248

Example 11

(R=radical of the formula II, $R_1$, $R_2$, $R_3$, $R_4$, $R_5$=H, r=s=1, Y=—CH—$((CH_2)_3)_2$—, A=radical of the formula III, $R_{13}$, $R_{15}$, $R_{16}$, $R_{20}$, $R_{21}$, $R_{22}$, $G_1$=$CH_3$, n=p=1, m=0, x=2)

The compound of Example 11 is prepared by the method described in Example 1 using 1 mole equivalent of the compound prepared as described in A.4 and 2 mole equivalents of 1,1,1,3,3,5,5-heptamethyltrisiloxane.

U.V. ($CH_3CN$) max. at 254 nm ($\epsilon$ 8 161). $^1$H NMR ($CDCl_3$) δ [ppm]: 7.92 (m, 2 H arom.); (m, 1 H arom.); 7.32 (m, 2 H arom.); 5.14 (m, 1 H, —CH—O—C(O)); 1.58 (m, 4 H, 2 —C$\underline{H}_2$—$CH_2$—$CH_2$—Si—); 1.33 (m, 4 H, 2 —C$\underline{H}_2$—$CH_2$—Si—); 0.48 (m, 4 H, 2 —$CH_2$—Si—); 0.01 (m, 42 H, 14 Si—$CH_3$). m/z (CI) 689 ($MH^+$); according to the mass spectrum there are also further compounds present in a small amount: 469 ($MH^+$); 249 ($MH^+$).

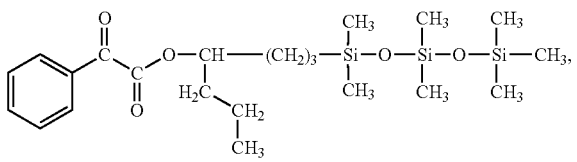

M = 468

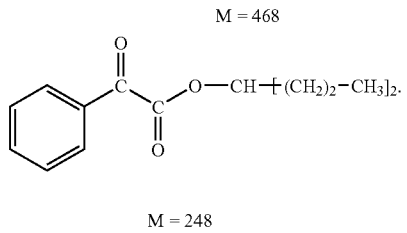

M = 248

Example 12

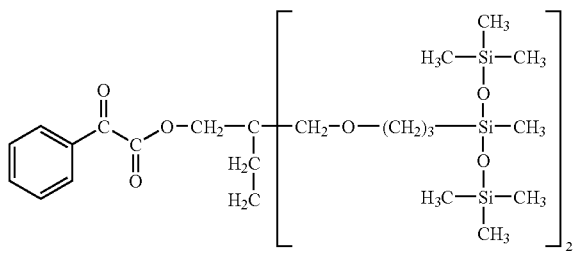

(R=radical of the formula II, $R_1$, $R_2$, $R_3$, $R_4$, $R_5$=H, r=s=1, Y=—$CH_2$—C(—$CH_2$—$CH_3$)(—$CH_2$—O—($CH_2$)$_3$)$_2$—, A=radical of the formula III, $R_{13}$, $R_{17}$, $R_{18}$, $R_{19}$, $R_{20}$, $R_{21}$, $R_{22}$=$CH_3$, n=1, m=p=0, x=2)

The compound of Example 12 is prepared by the method described in Example 1 using 1 mole equivalent of the compound prepared as described in A.5 and 2 mole equivalents of 1,1,1,3,5,5,5-heptamethyltrisiloxane.

U.V. ($CH_3CN$) max. at 254 nm ($\epsilon$ 13 646). $^1$H NMR (CDCl$_3$) δ [ppm]: 7.92 (m, 2 H arom.); 7.56 (m, 1 H arom.); 7.42 (m, 2 H arom.); 4.27 (s, 2 H, —$CH_2$—O—C(O)); 3.20 (m, 8 H, 2 —$CH_2$—O—$CH_2$—$CH_2$—$CH_2$—Si—); 1.47 (m, 6 H, 2 —$CH_2$—$CH_2$—Si— and $CH_2$—$CH_3$); 0.72 (m, 3 H, —$CH_2$—$CH_3$); 0.37 (m, 4 H, 2 —$CH_2$—Si—); 0.01 (m, 42 H, 14 Si—$CH_3$). m/z (CI) 791 (MH$^+$); according to the mass spectrum there are also further compounds present in a small amount: 529 (MH$^+$); 309 (MH$^+$); 307 (MH$^+$).

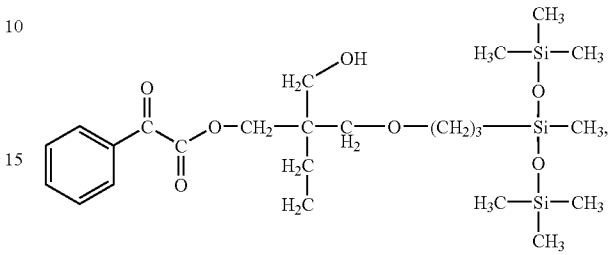

M = 528

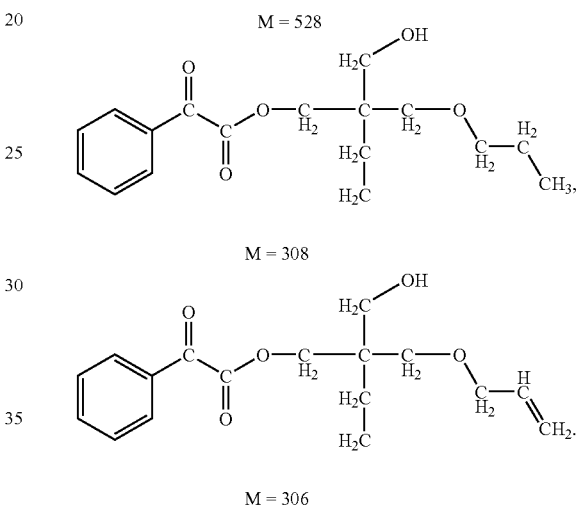

M = 308

M = 306

Example 13

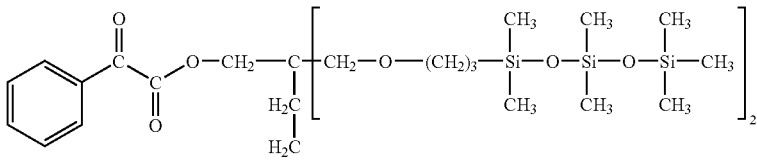

(R=radical of the formula II, $R_1$, $R_2$, $R_3$, $R_4$, $R_5$=H, r=s=1, Y=—$CH_2$—C(—$CH_2$—$CH_3$)(—$CH_2$—O—($CH_2$)$_3$)$_2$—, A=radical of the formula III, $R_{13}$, $R_{15}$, $R_{16}$, $R_{20}$, $R_{21}$, $R_{22}$, $G_1$=$CH_3$, n=p=1, m=0, x=2)

The compound of Example 13 is prepared by the method described in Example 1 using 1 mole equivalent of the compound prepared as described in A.5 and 2 mole equivalents of 1,1,1,3,3,5,5-heptamethyltrisiloxane.

U.V. ($CH_3CN$) max. at 254 nm ($\epsilon$ 12 736). $^1$H NMR (CDCl$_3$) δ [ppm]: 7.92 (m, 2 H arom.); 7.56 (m, 1 H arom.); 7.42 (m, 2 H arom.); 4.26 (s, 2 H, —$CH_2$—O—C(O)); 3.23 (m, 8 H, 2 —$CH_2$—O—$CH_2$—$CH_2$—$CH_2$—Si—); 1.50 (m., 6 H, 2 —$CH_2$—$CH_2$—Si— und $CH_2$—$CH_3$); 0.81 (m, 3 H —$CH_2$—$CH_3$); 0.43 (m, 4 H, 2 —$CH_2$—Si—); 0.01 (m, 42 H, 14 Si—$CH_3$). m/z (CI) 791 (MH$^+$); according to the mass spectrum there are also further compounds present in a small amount: 529 (MH$^+$); 309 (MH$^+$); 307 (MH$^+$).

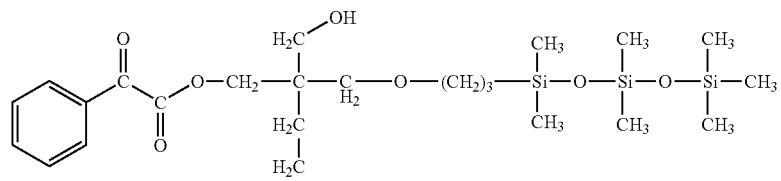

M = 528

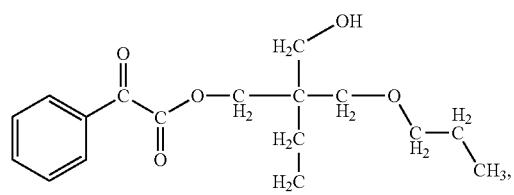

M = 308

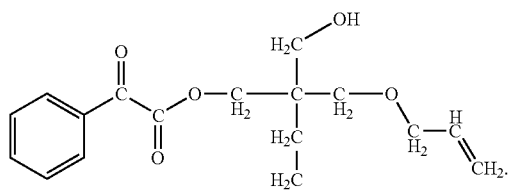

M = 306

Example 14

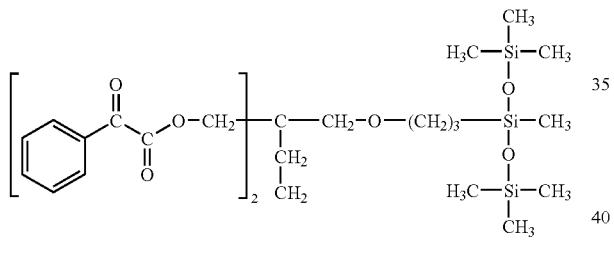

(R=radical of the formula II, $R_1$, $R_2$, $R_3$, $R_4$, $R_5$=H, r=2, s=1, Y=—$CH_2$—C(—$CH_2$—)(—$CH_2$—$CH_3$)—$CH_2$—O—($CH_2$)$_3$—, A=radical of the formula III, $R_{13}$, $R_{17}$, $R_{18}$, $R_{19}$, $R_{20}$, $R_{21}$, $R_{22}$=$CH_3$, n=1, m=p=0, x=1)

The compound of Example 14 is prepared by the method described in Example 1 using 1 mole equivalent of the compound prepared as described in A.7 and 1 mole equivalent of 1,1,1,3,5,5,5-heptamethyltrisiloxane.

U.V. ($CH_3CN$) max. at 254 nm ($\epsilon$ 22 582). $^1$H NMR ($CDCl_3$) δ [ppm]: 7.90 (m, 4 H arom.); 7.56 (m, 2 H arom.); 7.41 (m, 4 H arom.); 4.30 (s, 4 H, 2 —$CH_2$—O—C(O)); 3.27 (m, 4 H, —$C\underline{H}_2$—O—$C\underline{H}_2$—$CH_2$—$CH_2$—Si—); 1.44 (m, 4 H, —$C\underline{H}_2$—$CH_2$—Si— and $C\underline{H}_2$—$CH_3$); 0.84 (m, 3 H, —$CH_2$—$C\underline{H}_3$); 0.37 (m, 2 H, —$CH_2$—Si—); 0.01 (m, 21 H, 7 Si—$CH_3$). m/z (CI) 660 ($MH^+$); according to the mass spectrum there are also further compounds present in a small amount: 528 ($M_+$); 238 ($M_+$).

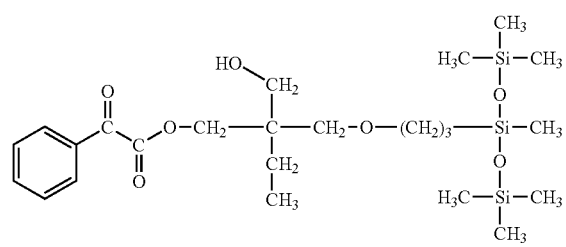

M = 528

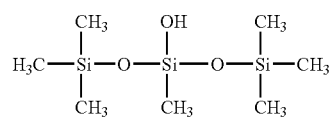

M = 238

Example 15

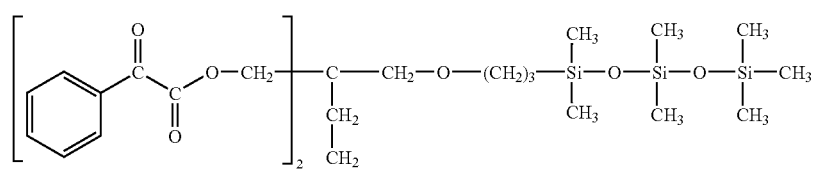

(R=radical of the formula II, $R_1$, $R_2$, $R_3$, $R_4$, $R_5$=H, r=2, s=1, Y=—$CH_2$—C(—$CH_2$—)(—$CH_2$—$CH_3$)—$CH_2$—O—($CH_2$)$_3$—, A=radical of the formula III, $R_{13}$, $R_{15}$, $R_{16}$, $R_{20}$, $R_{21}$, $R_{22}$, $G_1$=$CH_3$, n=p=1, m=0, x=1)

The compound of Example 15 is prepared by the method described in Example 1 using 1 mole equivalent of the compound prepared as described in A.7 and 1 mole equivalent of 1,1,1,3,3,5,5-heptamethyltrisiloxane.

$^1$H NMR (CDCl$_3$) δ [ppm]: 7.89 (m, 4 H arom.); 7.56 (m, 2 H arom.); 7.41 (m, 4 H arom.); 4.27 (s, 4 H, 2 —$CH_2$—O—C(O)); 3.25 (m, 4 H, —C$\underline{H}_2$—O—C$\underline{H}_2$—$CH_2$—$CH_2$—Si—); 1.50 (m, 4 H, —C$\underline{H}_2$—$CH_2$—Si— and C$\underline{H}_2$—$CH_3$); 0.81 (m, 3 H, —$CH_2$—C$\underline{H}_3$); 0.42 (m, 2H, —$CH_2$—Si—); 0.01 (m, 21 H, 7 Si—$CH_3$).

Example 16

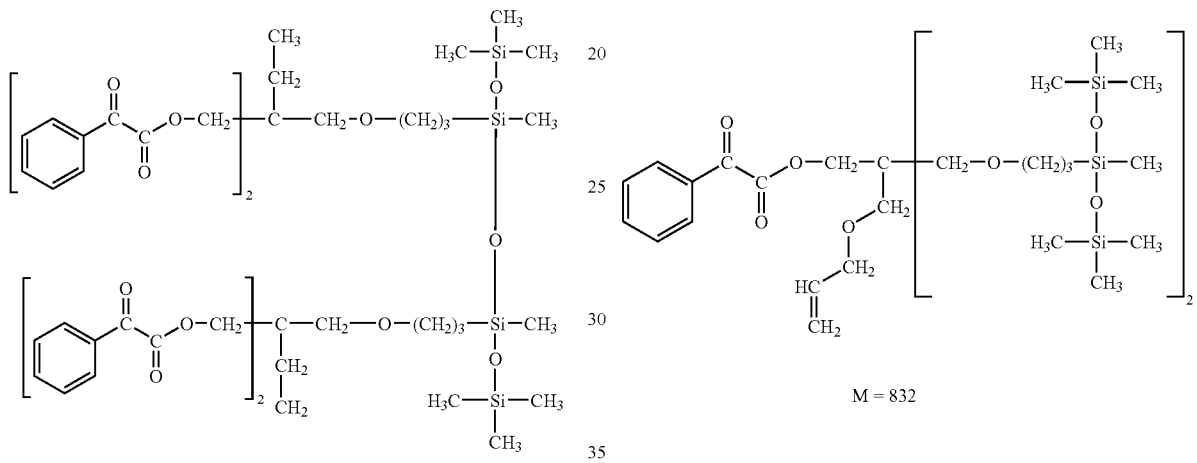

(R=radical of the formula II, $R_1$, $R_2$, $R_3$, $R_4$, $R_5$=H, r=2, s=2, Y=—$CH_2$—C(—$CH_2$—)(—$CH_2$—$CH_3$)—$CH_2$—O—($CH_2$)$_3$—, A=radical of the formula III, $R_{13}$, $R_{17}$, $R_{18}$, $R_{19}$, $R_{20}$, $R_{21}$, $R_{22}$=$CH_3$, n=2, p=m=0, x=1)

The compound of Example 16 is prepared by the method described in Example 1 using 2 mole equivalents of the compound prepared as described in A.7 and 1 mole equivalent of 1,1,1,3,5,7,7,7-octamethyltetrasiloxane.

$^1$H NMR (CDCl$_3$) δ [ppm]: 7.91 (m, 8 H arom.); 7.55 (m, 4 H arom.); 7.41 (m, 8 H arom.); 4.29 (m, 8 H, 4 —$CH_2$—O—C(O)—); 3.51 (s, 4 H, 2 —C(C$\underline{H}_2$—$CH_3$)—C$\underline{H}_2$—O—($CH_2$)$_3$—); 3.27 (m, 4 H, 2 —O—C$\underline{H}_2$—$CH_2$—$CH_2$—Si—); 1.44 (m, 8 H, 2 —C$\underline{H}_2$—$CH_2$—Si— and 2 —C$\underline{H}_2$—$CH_3$); 0.84 (m, 10 H, 2 —$CH_2$—Si— and 2 —$CH_2$—$CH_3$); 0.01 (m, 24 H, 8 Si—$CH_3$).

Example 17

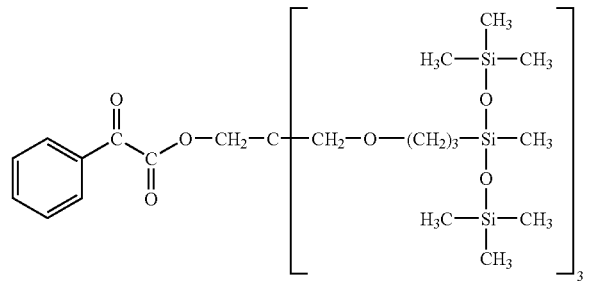

(R=radical of the formula II, $R_1$, $R_2$, $R_3$, $R_4$, $R_5$=H, r=s=1, Y=—$CH_2$—C—($CH_2$—O—($CH_2$)$_3$)$_3$—, A=radical of the formula III, $R_{13}$, $R_{17}$, $R_{18}$, $R_{19}$, $R_{20}$, $R_{21}$, $R_{22}$=$CH_3$, n=1, m=p=0, x=3)

The compound of Example 17 is prepared by the method described in Example 1 using 1 mole equivalent of the compound prepared as described in A.6 and 3 mole equivalents of 1,1,1,3,5,5,5-heptamethyltrisiloxane.

U.V. (CH$_3$CN) max. at 255 nm (ε 12 593). $^1$H NMR (CDCl$_3$) δ [ppm]: 7.92 (m, 2 H arom.); 7.56 (m, 1 H arom.); 7.41 (m, 2 H arom.); 4.36 (s, 2 H, —$CH_2$—O—C(O)); 3.36 (m, 6 H, 3 —C$\underline{H}_2$—O—$CH_2$—$CH_2$—$CH_2$—Si—); 3.25 (m, 6 H, 3 —O—C$\underline{H}_2$—$CH_2$—$CH_2$—Si—); 1.48 (m, 6 H, 3 —C$\underline{H}_2$—$CH_2$—Si); 0.36 (m, 6 H, 3 —$CH_2$—Si—); 0.01 (m, 63 H, 21 Si—$CH_3$). m/z (ESI-MS) 1077 ([M+Na]$^+$); according to the mass spectrum there is also a further compound present in a small amount: 855 ([M+Na]$^+$).

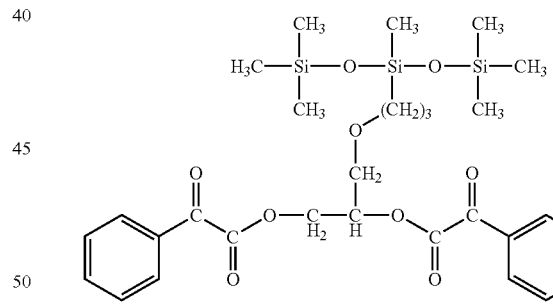

M = 832

Example 18

(R=radical of the formula II, $R_1$, $R_2$, $R_3$, $R_4$, $R_5$=H, r 2, s=1, Y=—$CH_2$—(CH—)—$CH_2$—O—($CH_2$)$_3$—, A=radical of the formula III, $R_{13}$, $R_{17}$, $R_{18}$, $R_{19}$, $R_{20}$, $R_{21}$, $R_{22}$=$CH_3$, n=1, m=p=0, x=1)

The compound of Example 18 is prepared by the method described in Example 1 using 1 mole equivalent of the compound prepared as described in A.8 and 1 mole equivalent of 1,1,1,3,5,5,5-heptamethyltrisiloxane.

U.V. (CH$_3$CN) max. at 255 nm (ε 22 800). $^1$H NMR (CDCl$_3$) δ [ppm]: 7.94 (m, 4 H arom.); 7.56 (m, 2 H arom.); 7.39 (m, 4 H arom.); 5.57 (m, 1 H, —CH—O—C(O)); 4.65 (m, 2 H, —$CH_2$—O—C(O)); 3.66 (d, J=6, 2 H, —C$\underline{H}_2$—O—$CH_2$—$CH_2$—$CH_2$—Si—); 3.36 (m, 2 H, —O—C$\underline{H}_2$—$CH_2$—$CH_2$—Si—); 1.53 (m, 2 H, —C$\underline{H}_2$—$CH_2$—Si—); 0.37 (m, 2 H, —$CH_2$—Si—); 0.01 (m, 21

H, 7 Si—CH$_3$). m/z (CI) 618 (M$^+$); according to the mass spectrum there is also a further compound present in a small amount: 486 (M$^+$).

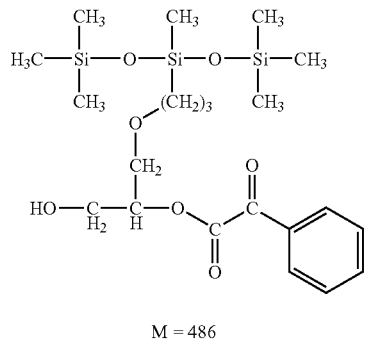

M = 486

Example 19

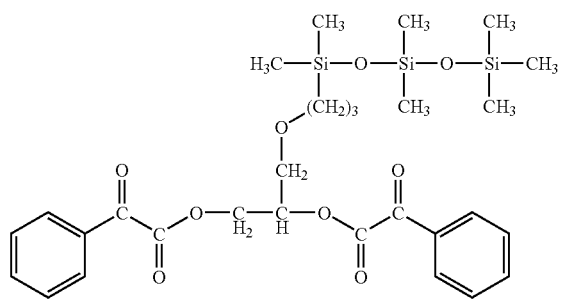

(R=radical of the formula II, R$_1$, R$_2$, R$_3$, R$_4$, R$_5$=H, r=2, s=1, Y=—CH$_2$—(CH—)—CH$_2$—O—(CH$_2$)$_3$—, A=radical of the formula III, R$_{13}$, R$_{15}$, R$_{16}$, R$_{20}$, R$_{21}$, R$_{22}$, G$_1$=CH$_3$, n=p=1, m=0, x=1)

The compound of Example 19 is prepared by the method described in Example 1 using 1 mole equivalent of the compound prepared as described in A.8 and 1 mole equivalent of 1,1,1,3,3,5,5-heptamethyltrisiloxane.

U.V. (CH$_3$CN) max. at 256 nm ($\epsilon$ 22 721). $^1$H NMR (CDCl$_3$) $\delta$ [ppm]: 7.91 (m, 4 H arom.); 7.53 (m, 2 H arom.); 7.37 (m, 4 H arom.); 5.58 (m, 1 H, —CH—O—C(O)); 4.73 (dd, J=3, J=12, 1 H, —CH$_2$—O—C(O)); 4.51 (dd, J=9, J=12, 1 H, —CH$_2$—O—C(O)); 3.67 (d, J=6, 2 H, —C$\underline{H}_2$13 O—CH$_2$—CH$_2$—CH$_2$—Si—); 3.37 (m, 2 H, —O—C $\underline{H}_2$—CH$_2$—CH$_2$—Si—); 1.52 (m, 2 H, —C $\underline{H}_2$—CH$_2$—Si—); 0.46 (m, 2 H, —CH$_2$—Si—); 0.01 (m, 21 H, 7 Si—CH$_3$). m/z (EI) 660 (M$^+$); according to the mass spectrum there are also further compounds present in a small amount: 398 (M$^+$); 238 (M$^+$).

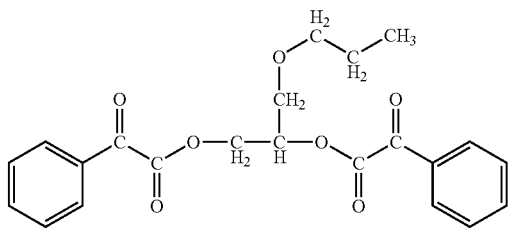

M = 398

-continued

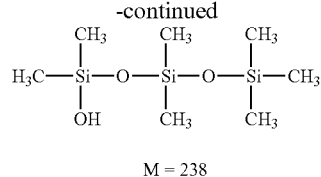

M = 238

Example 20

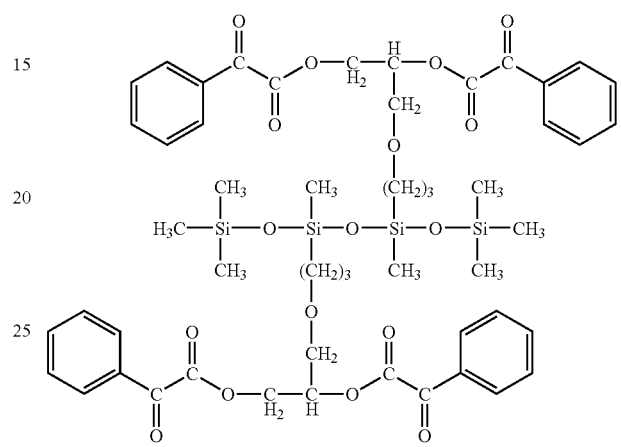

(R=radical of the formula II, R$_1$, R$_2$, R$_3$, R$_4$, R$_5$=H, r=2, s=2, Y=—CH$_2$—(CH—)—CH$_2$—O—(CH$_2$)$_3$—, A=radical of the formula III, R$_{13}$, R$_{17}$, R$_{18}$, R$_{19}$, R$_{20}$, R$_{21}$, R$_{22}$=CH$_3$, n=2, p=m=0, x=1)

The compound of Example 20 is prepared by the method described in Example 1 using 2 mole equivalents of the compound prepared as described in A.8 and 1 mole equivalent of 1,1,1,3,5,7,7,7-octamethyltetrasiloxane.

U.V. (CH$_3$CN) max. at 256 nm ($\epsilon$ 41 935). $^1$H NMR (CDCl$_3$) $\delta$ [ppm]: 7.91 (m, 8 H arom.); 7.53 (m, 4 H arom.); 7.37 (m, 8 H arom.); 5.57 (m, 2 H. —CH—O—C(O)); 4.74 (m, 2 H, 2 —CH$_2$—O—C(O)); 4.50 (m, 2 H, 2 —CH$_2$—O—C(O)); 3.65 (d, J=6, 4 H, 2 —C $\underline{H}_2$—O—CH$_2$—CH$_2$—CH$_2$—Si—); 3.39 (m, 4 H, 2 —O—C$\underline{H}_2$—CH$_2$—CH$_2$—Si—); 1.51 (m, 4 H, 2 —C $\underline{H}_2$—CH$_2$—Si—); 0.41 (m, 4 H, 2 —CH$_2$—Si—); 0.01 (m, 24 H, 8 Si—CH$_3$).

Example 21

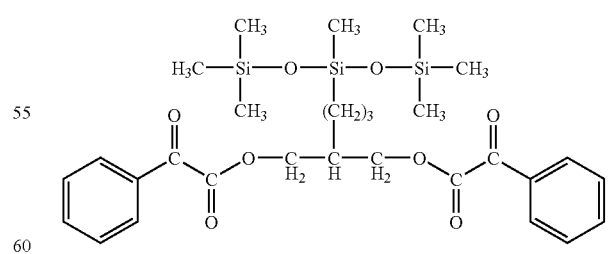

(R=radical of the formula II, R$_1$, R$_2$, R$_3$, R$_4$, R$_5$=H, r=2, s=1, Y=—CH$_2$—CH(—CH$_2$—)—(CH$_2$)$_3$—, A=radical of the formula III, R$_{13}$, R$_{17}$, R$_{18}$, R$_{19}$, R$_{20}$, R$_{21}$, R$_{22}$=CH$_3$, n=1, m=p=0, x=1)

The compound of Example 21 is prepared by the method described in Example 1 using 1 mole equivalent of the compound prepared as described in A.9 and 1 mole equivalent of 1,1,1,3,5,5,5-heptamethyltrisiloxane.

U.V. (CH$_3$CN) max. at 255 nm ($\epsilon$ 37 687). $^1$H NMR (CDCl$_3$) δ [ppm]: 7.89 (m, 4 H arom.); 7.53 (m, 2 H arom.); 7.39 (m, 4 H arom.); 4.34 (m, 4 H, 2 —CH$_2$—O—C(O)); 2.20 (m, 1 H, —CH—CH$_2$—CH$_2$—CH$_2$—Si—); 1.37 (m, 4 H, —CH—CH$_2$—CH$_2$—CH$_2$—Si—); 0.40 (m, 2 H, —CH$_2$—Si—); 0.01 (m, 21 H, 7 Si—CH$_3$). m/z (EI) 602 (M$^+$); according to the mass spectrum there are also further compounds present in a small amount: 514 (M$^+$); 459 (MH$^+$); 380 (M$^+$).

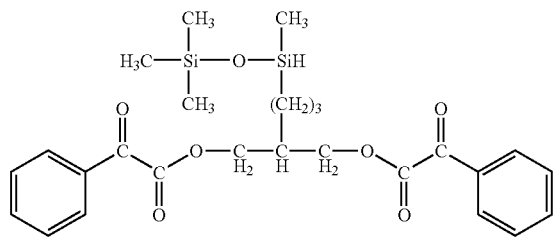

M = 514

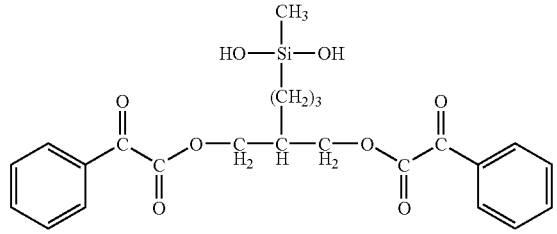

M = 458

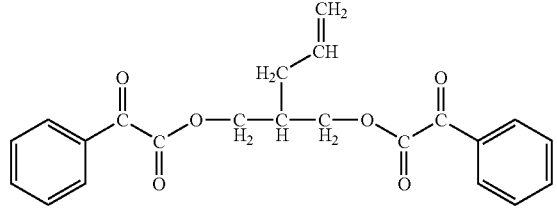

M = 380

Example 22

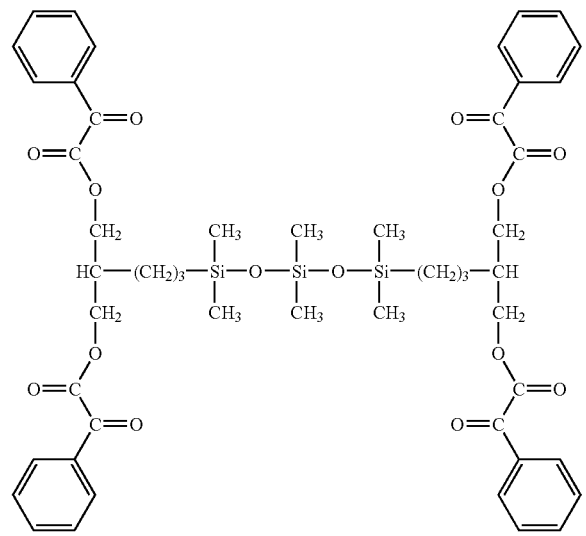

(R=radical of the formula II, R$_1$, R$_2$, R$_3$, R$_4$, R$_5$=H, r=2, s=2, Y=—CH$_2$—CH(—CH$_2$—)—(CH$_2$)$_3$—, A=radical of the formula III, R$_{13}$, R$_{15}$, R$_{16}$, G$_1$, G$_2$=CH$_3$, n=2, m=0, p=1, x=1)

The compound of Example 22 is prepared by the method described in Example 1 using 2 mole equivalents of the compound prepared as described in A.9 and 1 mole equivalent of 1,1,3,3,5,5-hexamethyltrisiloxane.

U.V. (CH$_3$CN) max. at 255 nm ($\epsilon$ 44 341). $^1$H NMR (CDCl$_3$) δ [ppm]: 7.90 (m, 8 H arom.); 7.60 (m, 4 H arom.); 7.39 (m, 8 H arom.); 4.36 (m, 8 H, 4 —CH$_2$—O—C(O)); 2.23 (m, 2 H, 2 —CH—CH$_2$—CH$_2$—CH$_2$—Si—); 1.39 (m, 8 H, 2 —CH—CH$_2$—CH$_2$—CH$_2$—Si—); 0.49 (m, 4 H, 2 —CH$_2$—Si—); 0.01 (m, 18 H, 6 Si—CH$_3$). m/z (ESI-MS) 992 ([M+Na]$^+$).

Example 23

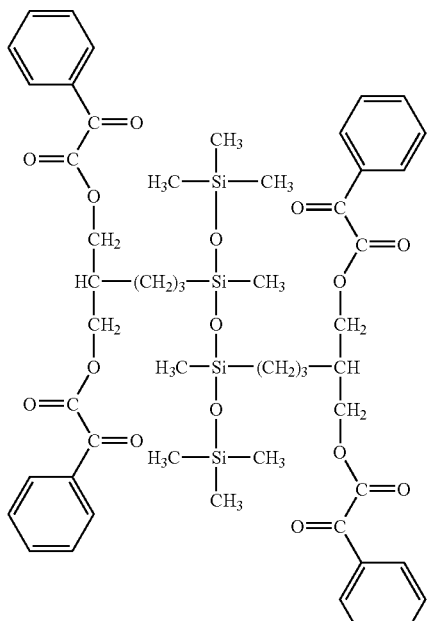

(R=radical of the formula II, R$_1$, R$_2$, R$_3$, R$_4$, R$_5$=H, r=2, s=2, Y=—Y=—CH$_2$—(CH—)—CH$_2$—O—(CH$_2$)$_3$—$_3$—, A=radical of the formula III, R$_{13}$, R$_{17}$, R$_{18}$, R$_{19}$, R$_{20}$, R$_{21}$, R$_{22}$=CH$_3$, n=2, m=p=0, x=1)

The compound of Example 23 is prepared by the method described in Example 1 using 2 mole equivalents of the compound prepared as described in A.9 and 1 mole equivalent of 1,1,1,3,5,7,7,7-octamethyltetrasiloxane.

$^1$H NMR (CDCl$_3$) δ [ppm]: 7.90 (m, 8 H arom.); 7.61 (m, 4 H arom.); 7.42 (m, 8 H arom.); 4.37 (m, 8 H, 4 —CH$_2$—O—C(O)); 2.24 (m, 2 H, 2 —CH—CH$_2$—CH$_2$—CH$_2$—Si—); 1.40 (m, 8 H, 2 —CH—CH$_2$—CH$_2$—CH$_2$—Si—); 0.44 (m, 4 H, 2 —CH$_2$—Si—); 0.01 (m, 24 H, 8 Si—CH$_3$).

Example 24

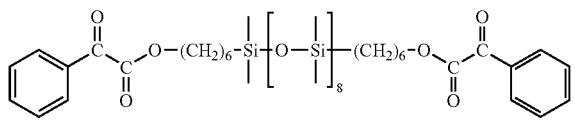

(R=radical of the formula II, $R_1$, $R_2$, $R_3$, $R_4$, $R_5$=H, r=1, s=2, Y=—$(CH_2)_6$—, A=radical of the formula III, $R_{13}$, $R_{15}$, $R_{16}$, $G_1$, $G_2$=$CH_3$, n=2, m=0, p=8, x=1)

A solution of 10 g of benzoylformic acid (glyoxalic acid), 27.06 g of Dicarbinol Siloxane Tegomer H-Si 2111 (from Goldschmidt), and 0.74 g of 4-dimethylaminopyridine in 500 ml of methylene chloride is cooled to 0° C. A solution of 12.24 g of N,N'-dicyclohexylcarbodiimide in 50 ml of methylene chloride is added dropwise over the course of 30 minutes. The mixture is warmed to room temperature and stirred for 17 hours. The mixture is filtered and the solvent is evaporated. The product is taken up in 150 ml of hexane and filtered. Chromatography (eluent: 3:1 hexane/ethyl acetate) gives the product (25.19 g, 70%) as a slightly yellow liquid.

U.V. ($CH_3CN$) max. at 254 nm ($\epsilon$ 11 804). $^1$H NMR ($CDCl_3$) $\delta$ [ppm]: 7.92 (m, 2 H arom.); 7.55 (m, 1 H arom.); 7.42 (m, 2 H arom.); 4.30 (t, J=6, 2×2 H, —C(O)—O—$CH_2$—); 1.68 (tt, J=9, J=9, 2×2 H, —C(O)—O—$CH_2$—$CH_2$—); 1.27 (m, 12 H, 2×3 —$CH_2$—); 0.45 (m, 4 H, 2 —$CH_2$—Si—); 0.01 (m, 60 H, 20 —Si—$CH_3$). m/z (EIS) 1116 ($M^+$); according to the mass spectrum there are also further compounds present in a small amount: 1042 ($M^+$); 968 ($M^+$); 894 ($M^+$); 820 ($M^+$); 746 ($M^+$); 672 ($M^+$).

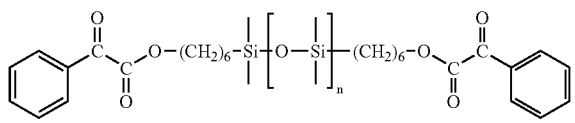

| M = 1042 | n = 7 |
| M = 968 | n = 6 |
| M = 894 | n = 5 |
| M = 820 | n = 4 |
| M = 746 | n = 3 |
| M = 672 | n = 2 |

Example 25

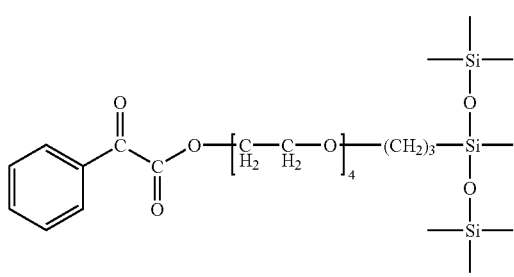

(R=radical of the formula II, $R_1$, $R_2$, $R_3$, $R_4$, $R_5$=H, r=s=1, Y=—$(CH_2$—$CH_2$—O$)_4$—$(CH_2)_3$—, A=radical of the formula III, $R_{13}$, $R_{17}$, $R_{18}$, $R_{19}$, $R_{20}$, $R_{21}$, $R_{22}$=$CH_3$, n=1, m=p=0, x=1)

6.22 g of 1,1'-carbonyldiimidazole are added in portions to a solution of 5 g of benzoylformic acid (glyoxalic acid) in 470 ml of tetrahydrofuran. This mixture is stirred for 30 minutes and added dropwise to a solution of 6.37 g of Carbinol Siloxane Q2-5211 (from Dow Corning) in 470 ml of tetrahydrofuran. The mixture is heated to 70° C. and stirred at 70° C. for 20 hours and at room temperature for 16 hours. Following the evaporation of the solvent, the product is dissolved in toluene and the solution is washed using an NaCl solution and water. The organic phases are dried over magnesium sulfate. Filtration, evaporation of the solvent and chromatography (eluent: 3:1 hexane/ethyl acetate) give the product as a yellow oil.

U.V. ($CH_3CN$) max. at 254 nm ($\epsilon$ 11 804). $^1$H NMR ($CDCl_3$) $\delta$ [ppm]: 7.93 (m, 2 H arom.); 7.57 (m, 1 H arom.); 7.43 (m, 2 H arom.); 4.46 (m, 2 H, —C(O)—O—$CH_2$—); 3.75 (m, 2 H, —C(O)—O—$CH_2$—$CH_2$); 3.58 (m, 12 H, 3 —$CH_2$—$CH_2$—O—); 3.23 (t, J=6, 2 H, —O—C$H_2$—$CH_2$—$CH_2$—Si—); 1.51 (m, 2 H, —$CH_2$—C$H_2$—$CH_2$—Si—); 0.34 (m, 2 H, —$CH_2$—$CH_2$—C$H_2$—Si—); 0.01 (m, 21 H, 7 —Si—$CH_3$). m/z (EI) 1190 ($M^+$).

Example 26

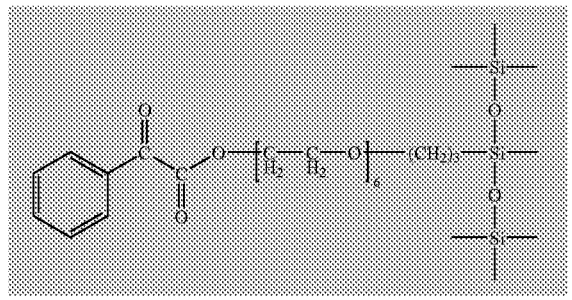

(R=radical of the formula II, $R_1$, $R_2$, $R_3$, $R_4$, $R_5$=H, r=s=1, Y=—$(CH_2$—$CH_2$—O$)_6$—$(CH_2)_3$—, A=radical of the formula III, $R_{13}$, $R_{17}$, $R_{18}$, $R_{19}$, $R_{20}$, $R_{21}$, $R_{22}$=$CH_3$, n=1, m=p=0, x=1)

The compound of Example 26 is prepared by the method described in Example 25 using 2 mole equivalent of benzoylformic acid (glyoxalic acid), 2.3 mole equivalent 1,1'-carbonyl-diimidazole and 1 mole equivalent carbinol siloxane L 7608 (Witco).

U.V. ($CH_3CN$) max. bei 255 nm ($\epsilon$ 20'470). $^1$H NMR ($CDCl_3$) $\delta$ [ppm]: 7.93 (m, 2 H arom.); 7.57 (m, 1 H arom.); 7.43 (m, 2 H arom.); 4.46 (m, 2 H, —C(O)—O—$CH_2$—); 3.75 (m, 2 H, —C(O)—O—$CH_2$—$CH_2$—); 3.58 (m, 20 H, 5 —$CH_2$—$CH_2$—O—); 3.23 (m, J=6, 2 H, —O—C$H_2$—$CH_2$—$CH_2$—Si—); 1.49 (m, 2 H, —$CH_2$—C$H_2$—$CH_2$—Si—); 0.34 (m, 2 H, —$CH_2$—$CH_2$—C$H_2$—Si—); 0.01 (m, 21 H, 7 —Si—$CH_3$).

Example 27

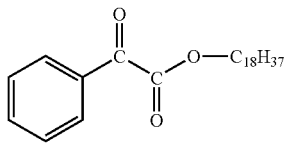

(R=radical of the formula II, $R_1$, $R_2$, $R_3$, $R_4$, $R_5$=H, r=s=1, Y=a single bond, A=—$(CH_2)_{17}$—$CH_3$)

A solution of 5 g of benzoylformic acid (glyoxalic acid), 11.3 g of octadecanol and 0.19 g of p-toluenesulfonic acid in 60 ml of toluene is heated at reflux for 22 hours. The mixture is poured into saturated $NaHCO_3$ solution and the phases are separated. The organic phases are washed with water and dried over sodium sulfate. Filtration and evaporation of the solvent give octadecyl glyoxalate (17.7 g) as a yellow solid. The product is recrystallized from methanol to give slightly yellowish crystals (11.29 g, 84%).

U.V. ($CH_3CN$) max. at 254 nm ($\epsilon$ 11 804). $^1$H NMR ($CDCl_3$) δ [ppm]: 7.80 (m, 2 H arom.); 7.47 (m, 1 H arom.); 7.32 (m, 2 H arom.); 4.19 (t, J=6.7, 2 H, —C(O)—O—$CH_2$—); 1.56 (m, 2 H, —C(O)—O—$CH_2$—$CH_2$—); 1.06 (m, 30 H, 15 —$CH_2$—); 0.68 (t, J=6.3, 3 H, —$CH_3$). m/z (EI) 403 ($MH^+$).

Example 28

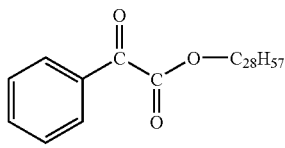

(R=radical of the formula II, $R_1$, $R_2$, $R_3$, $R_4$, $R_5$=H, r=s=1, Y=a single bond, A=—$(CH_2)_{27}$—$CH_3$)

The compound of Example 27 is prepared by the method described in Example 27 using 1 mole equivalent of benzoylformic acid (glyoxalic acid) and 1.25 mole equivalents of 1-octacosanol.

U.V. ($CH_3CN$) max. at 256 nm ($\epsilon$ 11 816). $^1$H NMR ($CDCl_3$), δ [ppm]: 7.92 (m, 2 H arom.); 7.58 (m, 1 H arom.); 7.44 (m, 2 H arom.); 4.31 (t, J=6.6, 2 H, —C(O)—O—$CH_2$—); 1.71 (m, 2 H, —C(O)—O—$CH_2$—$CH_2$—); 1.18 (m, 50 H, 25 —$CH_2$—); 0.81 (t, J=6.3, 3 H, —$CH_3$). m/z (EI) 542 ($M^+$).

Example 29

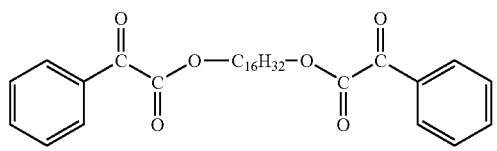

(R=radical of the formula II, $R_1$, $R_2$, $R_3$, $R_4$, $R_5$=H, r=1, s=2, Y=a single bond, A=—$(CH_2)_{16}$—)

A solution of 1.27 g of benzoylformic acid (glyoxalic acid), 1 g of 1,16-hexadecanediol and 0.09 g of 4-dimethylaminopyridine in 50 ml of methylene chloride is cooled to 0° C. A solution of 1.59 g of N,N'-dicyclohexylcarbodiimide in 20 ml of methylene chloride is added dropwise over the course of 20 minutes. The mixture is heated to room temperature and stirred overnight. Filtration through silica gel and evaporation of the solvent gives the product (1.17 g, 58%) as a white solid.

U.V. ($CH_3CN$) max. at 254 nm ($\epsilon$ 23 654). $^1$H NMR ($CDCl_3$) δ [ppm]: 7.93 (m, 4 H arom.); 7.59 (m, 2 H arom.); 7.49 (m, 4 H arom.); 4.31 (t, J=6.9, 4 H, 2 —C(O)—O—$CH_2$—); 1.72 (m, 4 H, 2 —C(O)—O—$CH_2$—$CH_2$—); 1.20 (m, 24 H, 12 —$CH_2$—). m/z (EI) 522 ($M^+$).

Example 30

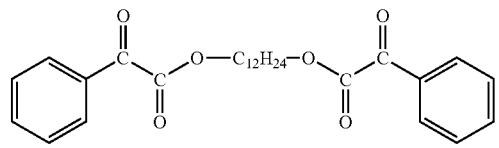

(R=radical of the formula II, $R_1$, $R_2$, $R_3$, $R_4$, $R_5$=H, r=1, s=2, Y=a single bond, A=—$(CH_2)_{12}$—)

The compound of Example 29 is prepared by the method described in Example 28 using 2.2 mole equivalents of benzoylformic acid (glyoxalic acid) and 1 mole equivalent of 1,12-dodecanediol.

U.V. ($CH_3CN$) max. at 254 nm ($\epsilon$ 23 869). $^1$H NMR ($CDCl_3$) δ [ppm]: 8.00 (m, 4 H arom.); 7.66 (m, 2 H arom.); 7.52 (m, 4 H arom.); 4.39 (t, J=6.6, 4 H, 2 —C(O)—O—$CH_2$—); 1.77 (m, 4 H, 2 —C(O)—O—$CH_2$—$CH_2$—); 1.28 (m, 16 H, 8 —$CH_2$—). m/z (CI) 466 ($M^+$).

Example 31

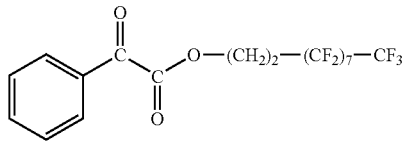

(R=radical of the formula II, $R_1$, $R_2$, $R_3$, $R_4$, $R_5$=H, r=s=1, Y=a single bond, A=—$(CH_2)_2$—$(CF_2)_7$—$CF_3$)

The compound of Example 30 is prepared by the method described in Example 27 using 1 mole equivalent of benzoylformic acid (glyoxalic acid) and 1.25 mole equivalents of 1H,1H,2H,2H-perfluorodecan-1-ol.

U.V. ($CH_3CN$) max. at 256 nm ($\epsilon$ 12 618). $^1$H NMR ($CDCl_3$) δ [ppm]: 7.90 (m, 2 H arom.); 7.58 (m, 1 H arom.); 7.40 (m, 2 H arom.); 4.57 (t, J=7.5, 2 H, —C(O)—O—$CH_2$—); 2.49 (m, 2 H, —C(O)—O—$CH_2$—$CH_2$—). m/z (CI) 596 ($M^+$).

Example 32

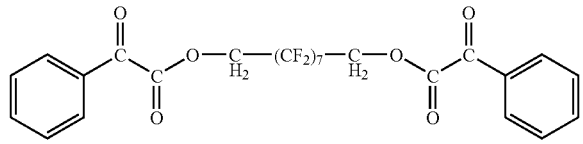

(R=radical of the formula II; $R_1, R_2, R_3, R_4, R_5$=H, r=1, s=2, Y is a bond, A=—$CH_2$—$(CF_2)_7$—$CH_2$—)

The compound of Example 32 is prepared by the method described in Example 27 using 2.2 mole equivalent of benzoylformic acid (glyoxalic acid) and 1.0 mole equivalents of 1H, 1H,9H,9H-perfluoro-1,9-nonadiol.

$^1$H NMR (CDCl$_3$) δ [ppm]: 8.00 (m, 2×2 H arom.); 7.70 (m, 2×1 H arom.); 7.52 (m, 2×2 H arom.); 4.87 (AB Syst., 2×2 H, —C(O)—O—CH$_2$—). m/z (EI+Cl) 677 (MH$^+$); according to the mass spectrum there are also further compounds present in a small amount: 627 (MH$^+$); 545 (MH$^+$).

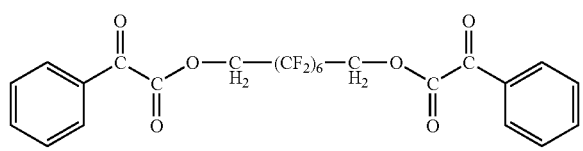

M = 626

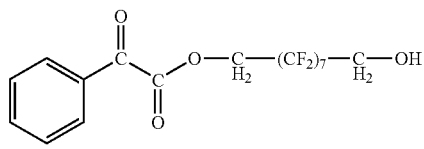

M = 544

APPLICATION EXAMPLES

Curing of a UV-Curable Clearcoat

A clear UV-curable system based on polyurethane acrylate is prepared by mixing:
50.0 parts of a bifunctional urethane acrylate (Actilan® 200, Akcros)
25.0 parts of tripropylene glycol diacrylate (SR 306, Cray Valley)
15.0 parts of trimethylolpropane triacrylate (TMPTA) (UCB)
10.0 parts of dipentaerythrol pentaacrylate (SR 399, Cray Valley)

The samples were prepared by adding 2% of the photoinitiator.

The mixtures were applied to a white chipboard panel and irradiated using a UV processor (2×80 W/cm) at a belt speed of 3 m/min. A tack-free dry film with a thickness of approximately 50 μm is obtained.

30 min. after cure, the pendulum hardness according to Koenig (DIN 53157) is measured. Surface energy of the coating is determined by measuring static water contact angle θ using a contact angle system G10 from Krüss. The higher the value of the pendulum hardness measurement, the harder the cured surface. The higher the contact angle, the better the moisture resistance and scratch resistance.

| Initiator | pendulum hardness (sec) | water contact angle θ |
|---|---|---|
| Nuvopol (Methyloxobenzene acetate) | 132 | 68 |
| Nuvopol Dimer | 127 | 64 |
| Ex. 3 | 127 | 85 |
| Ex. 4 | 130 | 92 |
| Ex. 5 | 141 | 95 |
| Ex. 6 | 118 | 83 |
| Ex. 7 | 118 | 81 |
| Ex. 8 | 129 | 89 |
| Ex. 9 | 129 | 86 |
| Ex. 10 | 132 | 83 |
| Ex. 11 | 130 | 81 |
| Ex. 12 | 123 | 89 |
| Ex. 13 | 129 | 85 |
| Ex. 14 | 144 | 82 |
| Ex. 18 | 134 | 89 |
| Ex. 19 | 144 | 83 |
| Ex. 20 | 130 | 84 |
| Ex. 21 | 144 | 88 |
| Ex. 22 | 138 | 79 |
| Ex. 24 | 126 | 89 |
| Ex. 26 | 120 | 88 |
| Ex. 27 | 88 | 85 |
| Ex. 31 | 143 | 94 |

A clear dual-cure system based on polyurethanes is prepared by mixing:
21.1 parts of Desmophen® LS 2009/1, hydroxy functional polyacrylate (Bayer AG)
32.3 parts of Roskydal® FWO 2518C, isocyanurate based urethane acrylate 80% in butyl acetate (Bayer AG)
0.3 parts of Baysilone® OL 17, flow improver, 10% in xylene (Bayer AG)
0.3 parts of Modaflow® flow improver, (Monsanto)
26.0 parts of 1-Methoxy-2-propanol (Fluka Chemicals)
0.5 parts of Byk® 306, flow improver (Byk-Chemie)
11.2 parts of Roskydal® FWO 2545 E urethane acrylate with isocyanata groups (Bayer AG)

The samples were prepared by adding 2-3% of the photoinitiator, and to some extent light stabilizer and HALS (hindered amine light stabilizer) is used.

The mixtures were applied to a white coil-coated aluminium panel, air-dried for 5 min. at room temperature and heated on a hotplate at 80° C. for 10 min. Irradiation is then carried out using 20 flashes (Flash light lamp from Visit) at a distance of 20 cm. A tack-free dry film with a thickness of approximately 40 μm is obtained.

45 min. after cure, the pendulum hardness according to Koenig (DIN 53157) is measured. Surface energy of the coating is determined by measuring static water contact angle θ using a contact angle system G10 from Krüss. The higher the value of the pendulum hardness measurement, the harder the cured surface. The higher the contact angle, the better the moisture resistance and scratch resistance.

| Initiator | pendulum hardness (sec) | water contact angle θ |
|---|---|---|
| Nuvopol (Methyloxobenzene acetate) | | |
| Nuvopol Dimer | | |
| Ex. 3 | 50 | 100 |
| Ex. 4 | 39 | 94 |
| Ex. 5 | 28 | 95 |
| Ex. 6 | 62 | 91 |

-continued

| Initiator | pendulum hardness (sec) | water contact angle θ |
|---|---|---|
| Ex. 8 | 45 | 95 |
| Ex. 9 | 53 | 92 |
| Ex. 19 | 63 | 90 |
| Ex. 20 | 88 | 93 |
| Ex. 21 | 41 | 94 |
| Ex. 24 | 48 | 97 |
| Ex. 26 | 45 | 94 |
| Ex. 27 | 38 | 90 |
| Ex. 31 | 55 | 108 |

The invention claimed is:

1. A process for producing coatings having scratch-resistant surfaces, in which
   (1) a photocurable formulation comprising
      (A) an ethylenically unsaturated polymerizable compound; and
      (B) a photoinitiator; is prepared;
   (2) this formulation is applied to a substrate; and
   (3) the formulation is cured either only by exposure to electromagnetic radiation with a wavelength ranging from 200 nm into the IR region, or by exposure to electromagnetic radiation with a wavelength ranging from 200 nm into the IR region and prior, simultaneous and/or subsequent exposure to heat;
   wherein
   the formulation comprises as photoinitiator (B) at least one surface-active photoinitiator of the formula I which accumulates at the surface of the formulation

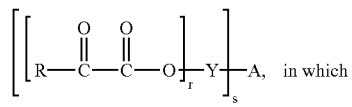

R is a radical of the formula II

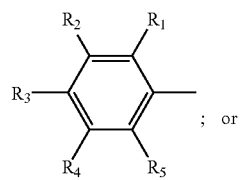

R is naphthyl, anthracyl, phenanthryl or a heterocyclic radical, the radicals naphthyl, anthracyl, phenanthryl and/or the heterocycle being unsubstituted or substituted by $C_1$-$C_8$alkyl, phenyl, $OR_6$, $SR_7$ and/or $NR_8R_9$, where the substituents $OR_6$, $SR_7$, $NR_8R_9$ may form 5- or 6-membered rings via the radicals $R_6$, $R_7$, $R_8$ and/or $R_9$ with further substituents on the naphthyl, anthracyl or phenanthryl ring or on the heterocycle or with one of the carbon atoms of the naphthyl, anthracyl or phenanthryl ring or with one of the carbon atoms of the heterocycle; and $R_1$, $R_2$, $R_3$, $R_4$ and $R_5$ independently of one another are hydrogen; unsubstituted $C_1$-$C_{12}$alkyl or $C_1$-$C_{12}$alkyl substituted by OH, $C_1$-$C_4$alkoxy, phenyl, naphthyl, halogen, CN and/or —O(CO)$R_{10}$; or are $C_2$-$C_{12}$alkyl interrupted by one or more non-successive oxygen atoms; or are $OR_6$; $SR_7$; $NR_8R_9$; halogen; unsubstituted or $C_1$-$C_4$alkyl- and/or $C_1$-$C_4$alkoxy-substituted phenyl, where the substituents $OR_6$, $SR_7$, NR8R$_9$ may form 5- or 6-membered rings via the radicals $R_6$, $R_7$, $R_8$ and/or $R_9$ with further substituents on the phenyl ring or one of the carbon atoms of the phenyl ring;

$R_6$ and $R_7$ independently of one another are hydrogen; unsubstituted $C_1$-$C_{12}$alkyl or $C_1$-$C_{12}$alkyl substituted by OH, $C_1$-$C_4$alkoxy, phenyl, phenoxy and/or —O(CO)$R_{10}$; or are $C_2$-$C_{12}$alkyl interrupted by one or more non-successive oxygen atoms; or are unsubstituted phenyl, $C_3$-$C_6$alkenyl, cyclopentyl, cyclohexyl or naphthyl; or are $C_1$-$C_4$alkoxy-, phenyl- and/or $C_1$-$C_4$alkyl-substituted phenyl, $C_3$-$C_6$alkenyl, cyclopentyl, cyclohexyl or naphthyl;

$R_8$ and $R_9$ independently of one another are hydrogen; unsubstituted $C_1$-$C_{12}$alkyl or $C_1$-$C_{12}$alkyl substituted by OH, $C_1$-$C_4$alkoxy and/or phenyl; or are $C_2$-$C_{12}$alkyl interrupted by one or more non-successive oxygen atoms; or are phenyl, —(CO)$R_{10}$ or $SO_2R_{11}$; or $R_8$ and $R_9$, together with the nitrogen atom to which they are attached, form a 5-, 6- or 7-membered ring which is uninterrupted or interrupted by —O— or —$NR_{12}$—;

$R_{10}$ is $C_1$-$C_8$alkyl; unsubstituted phenyl; or phenyl substituted by $C_1$-$C_4$alkyl and/or $C_1$-$C_4$alkoxy;

$R_{11}$ is $C_1$-$C_{12}$alkyl, unsubstituted phenyl or phenyl substituted by $C_1$-$C_4$alkyl;

$R_{12}$ is hydrogen; unsubstituted $C_1$-$C_8$alkyl; $C_1$-$C_8$alkyl substituted by OH or $C_1$-$C_4$alkoxy; unsubstituted phenyl; phenyl substituted by OH, $C_1$-$C_4$alkyl and/or $C_1$-$C_4$alkoxy; and

A, is a surface-active radical of the formula III

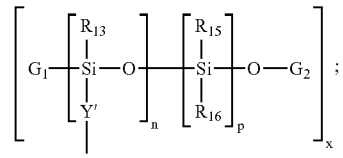

in which the units IIIa, IIIb and/or IIIc

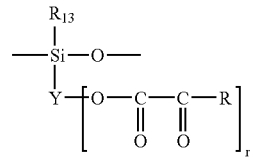

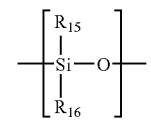

are distributed randomly or in blocks in which Y' indicates the position where A is connected to Y; and $G_1$ is $C_1$-$C_{18}$alkyl or a radical of the formula

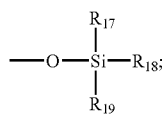

$G_2$ is a radical of the formula

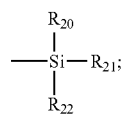

$R_{13}$, $R_{15}$, $R_{17}$, $R_{18}$, $R_{19}$, $R_{20}$, $R_{21}$ and $R_{22}$ independently of one another are $C_1$-$C_{18}$alkyl, phenyl, $C_2$-$C_6$hydroxyalkyl, $C_2$-$C_6$aminoalkyl or $C_5$-$C_8$cycloalkyl;

$R_{16}$ is unsubstituted $C_1$-$C_{18}$alkyl; $C_1$-$C_{18}$alkyl substituted by hydroxyl, $C_1$-$C_{12}$alkoxy, halogen, $C_3$-$C_8$cycloalkyl and/or $N(R_8)(R_9)$; unsubstituted phenyl; phenyl substituted by $C_1$-$C_{12}$alkyl, $C_1$-$C_{12}$alkoxy, halogen, hydroxyl and/or $N(R_8)(R_9)$; or $C_5$-$C_8$cycloalkyl;

r is 1 or 2; and, if r is 2, the compound of the formula I contains two radicals R which may be identical or different;

s is a number from 1 to 20;

n is a number from 1 to 20;

p is a number 0-25;

x is 1;

Y if r=1, is a divalent group $C_1$-$C_{10}$alkylene, $C_2$-$C_{10}$alkenylene, $C_2$-$C_{10}$alkynylene, —$(CH_2)_a$—O—, —$[(CH_2)_a$—O—$(CH_2)_b]_c$—, —$[(CH_2)_a$—O$]_q$—$(CH_2)_b$—, —$(CH_2)_a$—O—$(CH_2)_b$—O—, —$(CH_2)_a$—$NR_8$—$(CH_2)_b$—, —$(CH_2)_a$—O—$(CH_2)_b$—$NR_8$—$(CH_2)_c$—, —$(C_2$-$C_{10}$alkenylene)—O—$(CH_2)_a$—, —$(C_2$-$C_{10}$alkynylene)—O—$(CH_2)_a$—, Y, if r=2, is a trivalent group of the formulae:

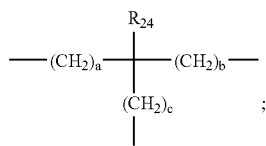

Y-1

Y-2

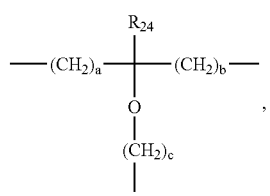

Y-3

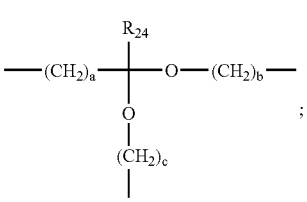

-continued

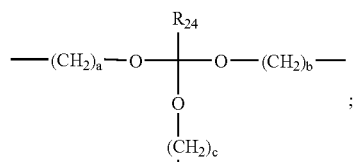

Y-4

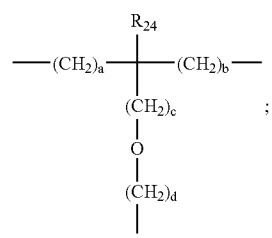

Y-5

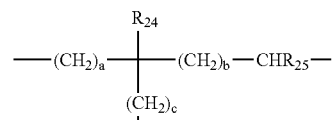

Y-6

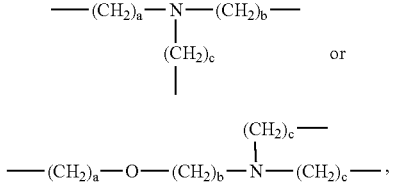

Y-7 or

Y-8

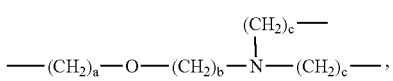

$R_{24}$ is hydrogen or $C_1$-$C_4$alkyl, $R_{25}$ is $C_1$-$C_4$alkyl;

and at the site of a bond to the photoinitiator radical

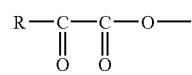

there must always be at least one methylene group; and a is a number from 1 to 10;

b, c and d independently of one another are a number from 0 to 10; with the proviso that they are, however, at least 1 if the methylene group in question is between two oxygen atoms or one oxygen and one nitrogen atom, and q is a number from 1 to 10.

2. A process according to claim 1, wherein the formulation comprises as photoinitiator (B) at least one surface-active photoinitiator of the formula I which accumulates at the surface of the formulation, and in formula I R is a radical of the formula II in which $R_1$, $R_2$, $R_3$, $R_4$ and $R_5$ independently of one another are hydrogen; unsubstituted $C_1$-$C_{12}$alkyl; $C_2$-$C_{12}$alkyl which is interrupted by one or more non-successive oxygen atoms; or are $OR_6$; $SR_7$; $NR_8R_9$; halogen; unsubstituted phenyl, where the substituents $OR_6$, $SR_7$, $NR_8R_9$ may form 5- or 6-membered rings via the radicals $R_6$, $R_7$, $R_8$ and/or $R_9$ with further substituents on the phenyl ring or one of the carbon atoms of the phenyl ring;

$R_6$ and $R_7$ independently of one another are hydrogen, unsubstituted $C_1$-$C_{12}$alkyl; OH-substituted $C_1$-$C_{12}$alkyl; unsubstituted phenyl, cyclopentyl or cyclohexyl;

$R_8$ and $R_9$ independently of one another are hydrogen, unsubstituted $C_1$-$C_{12}$alkyl; OH— or phenyl-substituted $C_1$-$C_{12}$alkyl; phenyl, —(CO)$R_{10}$; or $R_8$ and $R_9$, together with the nitrogen atom to which they are attached, form a 5-, 6- or 7-membered ring which is uninterrupted or interrupted by —O— or —$NR_{12}$—;

$R_{10}$ is $C_1$-$C_8$alkyl or unsubstituted or $C_1$-$C_4$alkyl- and/or $C_1$-$C_4$alkoxy-substituted phenyl;

$R_{12}$ is hydrogen, unsubstituted or OH— or $C_1$-$C_4$alkoxy-substituted $C_1$-$C_8$alkyl; or unsubstituted or OH—, $C_1$-$C_4$alkyl- or $C_1$-$C_4$alkoxy-substituted phenyl;

A, is a surface-active radical of the formula III in which $R_{13}$, $R_{15}$, $R_{17}$, $R_{18}$, $R_{19}$, $R_{20}$, $R_{21}$ and $R_{22}$ independently of one another are $C_1$-$C_{18}$alkyl, phenyl, $C_2$-$C_6$hydroxyalkyl, $C_2$-$C_6$aminoalkyl, cyclopentyl or cyclohexyl;

$R_{16}$ is unsubstituted $C_1$-$C_{18}$alkyl; $C_1$-$C_{18}$alkyl substituted by hydroxyl, $C_1$-$C_{12}$alkoxy, halogen, cyclohexyl, cyclopentyl and/or $N(R_8)(R_9)$; unsubstituted phenyl; phenyl substituted by $C_1$-$C_{12}$alkyl, $C_1$-$C_{12}$alkoxy, halogen, hydroxyl and/or $N(R_8)(R_9)$; or cyclohexyl, cyclopentyl;

s is a number from 1 to 10; and n is a number from 1 to 10.

3. A process according to claim 2, wherein the formulation comprises as photoinitiator (B) at least one surface-active photoinitiator of the formula I which accumulates at the surface of the formulation and in formula I R is phenyl, A is a radical of the formula III in which $R_{13}$, $R_{15}$, $R_{16}$, $R_{17}$, $R_{18}$, $R_{19}$, $R_{20}$, $R_{21}$ and $R_{22}$ are methyl;

s is 1 or 2; and when r=2, Y is a trivalent group of the formulae:

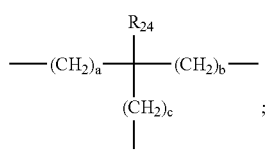

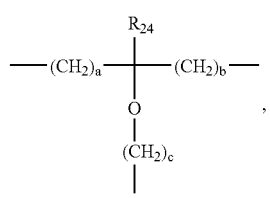

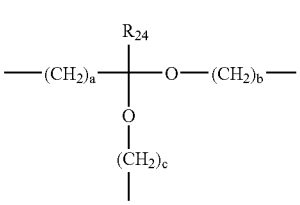

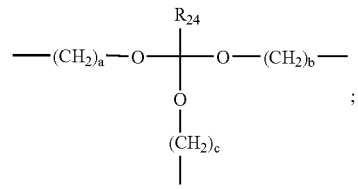

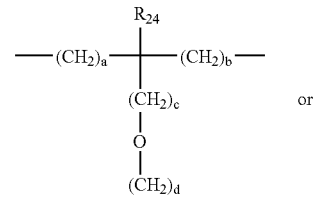

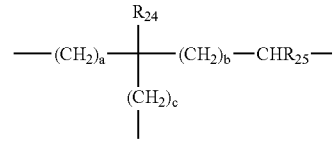

4. A surface-active photoinitiator of the formula I as defined in claim 3.

5. A process according to claim 1, wherein the photocurable formulation comprises as a further component at least one thermally crosslinkable compound (C) and is cured by exposure to electromagnetic radiation with a wavelength ranging from 200 nm into the IR region and prior, simultaneous and/or subsequent exposure to heat.

6. A process according to claim 5, wherein the thermally crosslinkable compound (C) is a binder based on a polyacrylate with melamine or melamine derivative, or a system based on a polyacrylate polyol and/or polyester polyol with an unblocked polyisocyanate or polyisocyanurate.

7. A surface-active photoinitiator of the formula I as defined in claim 1.

8. A composition comprising
(A) at least one ethylenically unsaturated free-radically photopolymerizable compound; and
(B) at least one surface-active photoinitiator of the formula I, according to claim 1 ; with the proviso that the composition contains no siloxane-modified resins besides the photoinitiator.

9. A composition according to claim 8, comprising in addition to components (A) and (B), further additives (D) and/or additional photoinitiators (E).

10. A coated substrate coated on at least one surface with a composition according to claim 8.

11. A composition comprising
(A) at least one ethylenically unsaturated free-radically photopolymerizable compound;
(B) at least one surface-active photoinitiator of the formula I according to claim 1, and
(C) at least one thermally crosslinkable compound; with the proviso that the composition contains no siloxane-modified resins besides the photoinitiator.

12. A composition according to claim 11, comprising in addition to components (A), (B) and (C), further additives (D) and/or additional photoinitiators(E).

13. A coated substrate coated on at least one surface with a composition according to claim 11.

14. A process according to claim 1 for preparing pigmented and unpigmented paints and varnishes, powder coating materials, gel coats, composite materials or glass fibre cable coatings.

15. A method of causing a photoinitiator to accumulate at the surface of coatings comprising ethylenically unsaturated photopolymerizable compounds, which comprises adding a surface-active photoinitiator of the formula I to the photopolymerizable mixture comprising the ethylenically unsaturated photopolymerizable compounds.

* * * * *